United States Patent
DaSilva-Jardine et al.

(10) Patent No.: US 11,248,042 B2
(45) Date of Patent: Feb. 15, 2022

(54) POLYNUCLEOTIDES ENCODING ANTI-APOC3 ANTIBODIES

(71) Applicant: STATEN BIOTECHNOLOGY B.V., Nijmegen (NL)

(72) Inventors: Paul DaSilva-Jardine, Guilford, CT (US); Hans de Haard, Oudelande (NL)

(73) Assignee: STATEN BIOTECHNOLOGY B.V., Nijmegen (NL)

( * ) Notice: Subject to any disclaimer, the term of this patent is extended or adjusted under 35 U.S.C. 154(b) by 0 days.

(21) Appl. No.: 16/714,294

(22) Filed: Dec. 13, 2019

(65) Prior Publication Data
US 2020/0239555 A1 Jul. 30, 2020

Related U.S. Application Data

(60) Division of application No. 16/248,507, filed on Jan. 15, 2019, now Pat. No. 10,538,583, which is a continuation of application No. PCT/IB2018/058564, filed on Oct. 31, 2018.

(60) Provisional application No. 62/579,449, filed on Oct. 31, 2017.

(51) Int. Cl.
| | |
|---|---|
| *C07K 16/18* | (2006.01) |
| *C12N 15/11* | (2006.01) |
| *C12N 15/63* | (2006.01) |
| *C12N 5/00* | (2006.01) |
| *A61K 39/395* | (2006.01) |
| *C07K 14/445* | (2006.01) |
| *A61P 3/06* | (2006.01) |
| *A61K 39/00* | (2006.01) |
| *C07K 14/775* | (2006.01) |

(52) U.S. Cl.
CPC .......... *C07K 16/18* (2013.01); *A61K 39/3955* (2013.01); *C12N 5/00* (2013.01); *C12N 15/11* (2013.01); *C12N 15/63* (2013.01); *A61K 2039/505* (2013.01); *A61P 3/06* (2018.01); *C07K 14/775* (2013.01); *C07K 2317/21* (2013.01); *C07K 2317/24* (2013.01); *C07K 2317/52* (2013.01); *C07K 2317/565* (2013.01); *C07K 2317/622* (2013.01); *C07K 2317/64* (2013.01); *C07K 2317/92* (2013.01); *C07K 2317/94* (2013.01); *C07K 2319/00* (2013.01)

(58) Field of Classification Search
CPC ... C07K 16/18; C07K 14/755; A61K 39/3955
See application file for complete search history.

(56) References Cited

U.S. PATENT DOCUMENTS

| | | | |
|---|---|---|---|
| 4,970,144 A | 11/1990 | Fareed et al. | |
| 6,737,056 B1 | 5/2004 | Presta | |
| 6,821,505 B2 | 11/2004 | Ward | |
| 7,083,784 B2 | 8/2006 | Dall'Acqua | |
| 7,098,036 B2 | 8/2006 | Koren et al. | |
| 7,217,797 B2 | 5/2007 | Hinton et al. | |
| 7,217,798 B2 | 5/2007 | Hinton et al. | |
| 7,662,925 B2 | 2/2010 | Lazar et al. | |
| 7,767,401 B2 | 8/2010 | Lescuyer et al. | |
| 8,030,288 B2 | 10/2011 | Berggren et al. | |
| 8,088,376 B2 | 1/2012 | Chamberlain et al. | |
| 8,163,881 B2 | 4/2012 | Ober | |
| 8,444,976 B2 | 5/2013 | Dreier et al. | |
| 8,524,231 B2 | 9/2013 | Dreier et al. | |
| 8,629,245 B2 | 1/2014 | Georgiou et al. | |
| 8,679,493 B2 | 3/2014 | Georgiou et al. | |
| 8,835,607 B2 | 9/2014 | Dreier et al. | |
| 9,221,918 B2 | 12/2015 | Dreier et al. | |
| 9,301,510 B2 | 4/2016 | McWhirter et al. | |
| 9,315,576 B2 | 4/2016 | Dreier et al. | |
| 9,346,891 B2 | 5/2016 | Dreier et al. | |
| 9,428,580 B2 | 8/2016 | Dreier et al. | |
| 9,540,437 B2 | 1/2017 | Dreier et al. | |
| 9,593,333 B2 | 3/2017 | Alexander et al. | |
| 9,868,948 B2 | 1/2018 | Igawa et al. | |
| 9,926,364 B2 | 3/2018 | De Haard | |
| 10,040,870 B2 | 8/2018 | De Haard | |
| 2004/0052809 A1 | 3/2004 | Mettens et al. | |
| 2008/0095762 A1 | 4/2008 | Presta | |
| 2009/0324589 A1 | 12/2009 | Igawa et al. | |
| 2010/0323376 A1 | 12/2010 | Contois | |
| 2011/0229489 A1 | 9/2011 | Pons et al. | |
| 2013/0131319 A1 | 5/2013 | Igawa et al. | |
| 2014/0093496 A1 | 4/2014 | Mimoto et al. | |
| 2014/0105889 A1 | 4/2014 | Igawa et al. | |

(Continued)

FOREIGN PATENT DOCUMENTS

| | | |
|---|---|---|
| EP | 2767548 A2 | 8/2014 |
| WO | WO-1997034631 A1 | 9/1997 |

(Continued)

OTHER PUBLICATIONS

Castellana et al, 2011. Proteomics. 11(3): 395-405.*
US20200216523A1, Jul. 9, 2020, Paul DaSilva-Jardine.
US20190135906A1, May 9, 2019, Paul DaSilva-Jardine.
WO2019087115A1, May 9, 2019, Paul DaSilva-Jardine.
Benjamini et al., "Immunology: A Short Course," Second Edition, Wiley-Liss Publisher (1991) p. 40.
Casset et al., "A peptide mimetic of an anti-CD4 monoclonal antibody by rational design," Biochem Biophys Res Commun. (2003) 307(1):198-205.
Chen et al., "Selection and analysis of an optimized anti-VEGF antibody: crystal structure of an affinity-matured Fab in complex with antigen," J Mol Biol. (1999) 293(4):865-81.

(Continued)

*Primary Examiner* — Zachary C Howard
(74) *Attorney, Agent, or Firm* — Dechert LLP; Andrew T. Wilkins; Elizabeth A. Browning

(57) ABSTRACT

The instant disclosure provides antibodies that specifically bind to ApoC3 (e.g., human ApoC3) and antagonize ApoC3 function. Also provided are pharmaceutical compositions comprising these antibodies, nucleic acids encoding these antibodies, expression vectors and host cells for making these antibodies, and methods of treating a subject using these antibodies.

15 Claims, 16 Drawing Sheets

Specification includes a Sequence Listing.

(56) References Cited

U.S. PATENT DOCUMENTS

| | | |
|---|---|---|
| 2014/0212435 A1 | 7/2014 | Moore et al. |
| 2014/0234340 A1 | 8/2014 | Igawa et al. |
| 2014/0255398 A1 | 9/2014 | Igawa et al. |
| 2014/0294812 A1 | 10/2014 | Lazar et al. |
| 2015/0056182 A1 | 2/2015 | Igawa et al. |
| 2015/0152183 A1 | 6/2015 | Chamberlain et al. |
| 2015/0166654 A1 | 6/2015 | Igawa et al. |
| 2015/0218239 A1 | 8/2015 | Ulrichts et al. |
| 2016/0009792 A1 | 1/2016 | Kiernan et al. |
| 2016/0046693 A1 | 2/2016 | Igawa et al. |
| 2016/0068613 A1 | 3/2016 | Regula et al. |
| 2016/0207996 A1 | 7/2016 | Ulrichts et al. |
| 2016/0264669 A1 | 9/2016 | Ultrichs et al. |
| 2017/0037118 A1 | 2/2017 | Berggren et al. |
| 2017/0037124 A1 | 2/2017 | Gusarova et al. |
| 2017/0342166 A1 | 11/2017 | Blanchetot et al. |
| 2018/0142027 A1 | 5/2018 | Igawa et al. |
| 2019/0135906 A1 | 5/2019 | DaSilva-Jardine et al. |
| 2019/0241648 A1 | 8/2019 | DaSilva-Jardine et al. |
| 2020/0148755 A1 | 5/2020 | DaSilva-Jardine et al. |
| 2020/0216523 A1 | 7/2020 | DaSilva-Jardine et al. |
| 2020/0239555 A1 | 7/2020 | DaSilva-Jardine et al. |

FOREIGN PATENT DOCUMENTS

| | | | |
|---|---|---|---|
| WO | WO-2001064008 | A2 | 9/2001 |
| WO | WO-2003020765 | A2 | 3/2003 |
| WO | WO-2003023407 | A1 | 3/2003 |
| WO | WO-2004080375 | A2 | 9/2004 |
| WO | WO-2004081045 | A2 | 9/2004 |
| WO | WO-2004081046 | A2 | 9/2004 |
| WO | WO-2004097429 | A2 | 11/2004 |
| WO | WO-2005047327 | A2 | 5/2005 |
| WO | WO-2006053301 | A2 | 5/2006 |
| WO | WO-2006130834 | A2 | 12/2006 |
| WO | WO-2009058492 | A2 | 5/2009 |
| WO | WO-2009086320 | A1 | 7/2009 |
| WO | WO-2010001251 | A2 | 1/2010 |
| WO | WO-2010045193 | A1 | 4/2010 |
| WO | WO-2010106180 | A2 | 9/2010 |
| WO | WO-2011005718 | A1 | 1/2011 |
| WO | WO-2011080350 | A1 | 7/2011 |
| WO | WO-2011111007 | A2 | 9/2011 |
| WO | WO-2013000920 | A2 | 1/2013 |
| WO | WO-2013064700 | A2 | 5/2013 |
| WO | WO-2013074598 | A1 | 5/2013 |
| WO | WO-2013100702 | A1 | 7/2013 |
| WO | WO-2014033252 | A1 | 3/2014 |
| WO | WO-2014033304 | A2 | 3/2014 |
| WO | WO-2014131008 | A1 | 8/2014 |
| WO | WO-2015032916 | A1 | 3/2015 |
| WO | WO-2016026943 | A1 | 2/2016 |
| WO | WO-2017055627 | A1 | 4/2017 |
| WO | WO-2017079748 | A1 | 5/2017 |
| WO | WO-2018007999 | A1 | 1/2018 |
| WO | WO-2018069416 | A1 | 4/2018 |
| WO | WO-2018193427 | A1 | 10/2018 |
| WO | WO-2018206748 | A1 | 11/2018 |
| WO | WO-2019087115 | A1 | 5/2019 |
| WO | WO-2020070678 | A2 | 4/2020 |

OTHER PUBLICATIONS

Cobaugh et al., "Synthetic antibody libraries focused towards peptide ligands," J Mol Biol. (2008) 378(3):622-33.

Ferrara et al., "Recombinant renewable polyclonal antibodies," MAbs. (2015) 7(1):32-41.

Holm et al., "Functional mapping and single chain construction of the anti-cytokeratin 8 monoclonal antibody TS1," Mol Immunol. (2007) 44(6):1075-84.

International Search Report and Written Opinion from PCT/IB2017/054125 dated Nov. 13, 2017.

International Search Report and Written Opinion from PCT/IB2018/052780 dated Jul. 31, 2018.

International Search Report and Written Opinion from PCT/IB2018/058564 dated Feb. 15, 2019.

International Search Report and Written Opinion from PCT/IB2019/058403 dated Mar. 25, 2020.

Khetarpal et al., "A human ApoC3 missense variant and monoclonal antibody accelerate apoC-III clearance and lower triglyceride-rich lipoprotein levels," Nat Med. (2017) 23(9):1086-1094.

MacCallum et al., "Antibody-antigen interactions: contact analysis and binding site topography," J Mol Biol. (1996) 262(5):732-45.

Pascalis et al., "Grafting of "abbreviated" complementarity-determining regions containing specificity-determining residues essential for ligand contact to engineer a less immunogenic humanized monoclonal antibody," J Immunol. (2002) 169(6):3076-84.

Rudikoff et al., "Single amino acid substitution altering antigen-binding specificity," Proc Natl Acad Sci U S A. (1982) 79(6):1979-83.

Unverdorben et al., "Pharmacokinetic properties of IgG and various Fc fusion proteins in mice," MAbs. (2016) 8(1):120-8.

Vajdos et al., "Comprehensive functional maps of the antigen-binding site of an anti-ErbB2 antibody obtained with shotgun scanning mutagenesis," J Mol Biol. (2002) 320(2):415-28.

Wu et al., "Humanization of a murine monoclonal antibody by simultaneous optimization of framework and CDR residues," J Mol Biol. (1999) 294(1):151-62.

Brown, et al., "Tolerance of single, but not multiple, amino acid replacements in antibody VH CDR 2: a means of minimizing B cell wastage from somatic hypermutation?," J Immunol. 1996; 156(9):3285-91.

Winkler, et al., "Changing the antigen binding specificity by single point mutations of an anti-p24 (HIV-1) antibody," J Immunol. 2000; 165(8):4504-14.

\* cited by examiner

POLYNUCLEOTIDES ENCODING ANTI-APOC3 ANTIBODIES

RELATED APPLICATIONS

This application is a division of U.S. patent application Ser. No. 16/248,507, filed Jan. 15, 2019, which is a continuation of International Patent Application No. PCT/IB2018/058564, filed Oct. 31, 2018, which claims the benefit of U.S. Provisional Patent Application No. 62/579,449, filed Oct. 31, 2017, the entire disclosures of which are incorporated by reference herein in their entirety.

FIELD

The instant disclosure relates to antibodies that specifically bind to ApoC3 (e.g., human ApoC3) and methods of using the same.

BACKGROUND

Elevated blood triglyceride levels (hypertriglyceridemia) are a causal factor for atherosclerosis, and increase the risk of cardiovascular events, such as cardiovascular death, angina, myocardial infarction, and stroke.

ApoC3 is a protein that circulates at very high concentrations (greater than 10 µM) in the blood, mostly bound to triglyceride rich lipoprotein (TRL), TRL remnants, and high density lipoprotein. ApoC3 appears to be an important regulator of blood triglyceride levels. For example, ApoC3 levels in humans have been shown to positively correlate with blood triglyceride levels, with elevated ApoC3 levels being associated with hypertriglyceridemia. In addition, ApoC3 has been shown to inhibit the activity of lipoprotein lipase (an enzyme that hydrolyses triglycerides in TRL) and also to inhibit hepatic uptake of TRL remnants, both of which cause elevation of blood triglyceride levels.

Several therapies have been approved for the treatment hypertriglyceridemia, such as fibrates, niacin, and omega-3 fatty acids. However these therapies are only modestly effective at lowering plasma triglycerides. Accordingly, there is a need in the art for improved therapies for lowering plasma triglycerides.

SUMMARY

The instant disclosure provides antibodies that specifically bind to ApoC3 (e.g., human ApoC3) and inhibit ApoC3 function. Also provided are pharmaceutical compositions comprising these antibodies, nucleic acids encoding these antibodies, expression vectors and host cells for making these antibodies, and methods of treating a subject using these antibodies.

In certain embodiments, the anti-ApoC3 antibodies disclosed herein can attenuate the ability of ApoC3 to inhibit TRL uptake by hepatocytes and can cause a rapid and sustained decrease in the serum levels of ApoC3 and ApoB when administered to a subject. Accordingly, the disclosed anti-ApoC3 antibodies are useful for the treatment and prevention of hypertriglyceridemia and associated diseases (e.g., cardiovascular disease and pancreatitis).

Accordingly, in one aspect, the instant disclosure provides an isolated antibody that specifically binds to ApoC3 with a first dissociation constant ($K_D$) at pH 7.4 and with a second $K_D$ at pH 5.5, wherein the ratio between the second $K_D$ and the first $K_D$ is at least about 5, 10, 20, or 50. In certain embodiments, the first $K_D$ is less than 10, 5, 2, 1, 0.5, 0.2, or 0.1 nM. In certain embodiments, the half-life of the antibody in a mouse expressing ApoC3 is at least about 3, 7, 14, 21, or 28 days.

In certain embodiments, the antibody attenuates the ability of ApoC3 to inhibit hepatocyte uptake of very low density lipoprotein (VLDL). In certain embodiments, the antibody is capable of increasing the rate of clearance of ApoC3 from the blood in a subject. In certain embodiments, the antibody is capable of increasing the rate of clearance of ApoB from the blood in a subject. In certain embodiments, the antibody is capable of reducing the level of ApoC3 in the blood in a subject. In certain embodiments, the antibody is capable of reducing the level of ApoC3 in the blood in a subject by at least 40% for at least 2 weeks. In certain embodiments, the antibody is capable of reducing the level of ApoB in the blood in a subject. In certain embodiments, the antibody is capable of reducing the level of ApoB in the blood in a subject by at least 20% for at least 2 weeks. In certain embodiments, the antibody is capable of inhibiting post-prandial lipemia in a subject. In certain embodiments, the antibody is capable of binding to lipid-bound ApoC3.

In certain embodiments, the antibody binds to an epitope within the amino acid sequence set forth in SEQ ID NO: 2. In certain embodiments, the epitope comprises at least one of the amino acids at position 2, 5, 6, 8, or 10 of SEQ ID NO: 2. In certain embodiments, the epitope comprises the amino acids at positions 5 and 6 of SEQ ID NO: 2. In certain embodiments, the epitope comprises the amino acids at positions 2, 5, 6, and 8 of SEQ ID NO: 2. In certain embodiments, the epitope comprises the amino acids at position 10 of SEQ ID NO: 2. In certain embodiments, the epitope comprises the amino acids at positions 6, 8, and 10 of SEQ ID NO: 2. In certain embodiments, the epitope comprises the amino acids at positions 6 and 8 of SEQ ID NO: 2.

In certain embodiments, the antibody (e.g., humanized antibody) comprises a heavy chain variable region having complementarity determining regions CDRH1, CDRH2 and CDRH3, and a light chain variable region having complementarity determining regions CDRL1, CDRL2 and CDRL3, and wherein:
(a) CDRH1 comprises the amino acid sequence of TYSMR (SEQ ID NO: 3);
(b) CDRH2 comprises the amino acid sequence of SIHTX$_1$X$_2$GGTAYRDSVKG, wherein X$_1$ is G, E, or D, and X$_2$ is G or A (SEQ ID NO: 87);
(c) CDRH3 comprises the amino acid sequence of AGYSD (SEQ ID NO: 10);
(d) CDRL1 comprises the amino acid sequence of KTSQGLVHSXGKTYFY, wherein X is D or G (SEQ ID NO: 88);
(e) CDRL2 comprises the amino acid sequence of QVSNRAS (SEQ ID NO: 7); and
(f) CDRL3 comprises the amino acid sequence of AXGTYYPHT, wherein X is Q or H (SEQ ID NO: 8), and optionally wherein the CDRH1, CDRH2, and CDRH3 of the antibody are not SEQ ID NOs: 3, 9, 10; 3, 11, 10; 3, 9, 12; or 3, 11, 12, respectively.

In certain embodiments, CDRH2 comprises the amino acid sequence of SIHTGGGGTAYRDSVKG (SEQ ID NO: 36), SIHTEAGGTAYRDSVKG (SEQ ID NO: 37), SIHTDAGGTAYRDSVKG (SEQ ID NO: 38), or SIHTEGGGTAYRDSVKG (SEQ ID NO: 39). In certain embodiments, CDRL1 comprises the amino acid sequence of KTSQGLVHSDGKTYFY (SEQ ID NO: 6) or KTSQGLVHSGGKTYFY (SEQ ID NO: 40). In certain embodiments, CDRL3 comprises the amino acid sequence of AHGTYYPHT (SEQ ID NO: 14) or AQGTYYPHT (SEQ ID NO: 13).

In certain embodiments, the CDRH1, CDRH2, CDRH3, CDRL1, CDRL2, and CDRL3 comprise the amino acid sequences set forth in SEQ ID NOs: 3, 36, 10, 6, 7, and 14; 3, 37, 10, 40, 7, and 14; 3, 38, 10, 40, 7, and 14; 3, 38, 10, 6, 7, and 14; 3, 39, 10, 6, 7, and 14; or 3, 37, 10, 40, 7, and 13, respectively. In certain embodiments, the heavy chain variable region comprises an amino acid sequences selected from the group consisting of SEQ ID NOs: 42-53. In certain embodiments, the light chain variable region comprises an amino acid sequences selected from the group consisting of SEQ ID NOs: 54-65. In certain embodiments, the heavy chain variable region and the light chain variable region, respectively, comprise the amino acid sequences set forth in SEQ ID NOs: 42 and 54, 43 and 55, 44 and 56, 45 and 57, 46 and 58, 46 and 54, 47 and 58, 47 and 54, 48 and 58, 48 and 54, 49 and 59, 49 and 60, 50 and 59, 50 and 60, 51 and 61, 52 and 62, 53 and 62, 43 and 63, 44 and 64, or 45 and 65.

In certain embodiments, the antibody comprises a heavy chain variable region having complementarity determining regions CDRH1, CDRH2 and CDRH3, and a light chain variable region having complementarity determining regions CDRL1, CDRL2 and CDRL3, and wherein:
(a) CDRH1 comprises the amino acid sequence of TYSMR (SEQ ID NO: 3);
(b) CDRH2 comprises the amino acid sequence of SIX$_1$TDGGGTAYRDSVKG, wherein X$_1$ is S or H (SEQ ID NO: 4);
(c) CDRH3 comprises the amino acid sequence of X$_2$GYSD, wherein X$_2$ is A or H (SEQ ID NO: 5);
(d) CDRL1 comprises the amino acid sequence of KTSQGLVHSDGKTYFY (SEQ ID NO: 6);
(e) CDRL2 comprises the amino acid sequence of QVSNRAS (SEQ ID NO: 7); and
(f) CDRL3 comprises the amino acid sequence of AX$_3$GTYYPHT, wherein X$_3$ is Q or H (SEQ ID NO: 8), and wherein at least one of X$_1$, X$_2$, and X$_3$ is H.

In certain embodiments, the CDRH1, CDRH2, CDRH3, CDRL1, CDRL2, and CDRL3 comprise the amino acid sequences set forth in SEQ ID NOs: 3, 11, 10, 6, 7, and 13; 3, 9, 12, 6, 7, and 13; 3, 9, 10, 6, 7, and 14; 3, 11, 10, 6, 7, and 14; 3, 9, 12, 6, 7, and 14; 3, 11, 12, 6, 7, and 13; or 3, 11, 12, 6, 7, and 13, respectively. In certain embodiments, the heavy chain variable region comprises an amino acid sequences selected from the group consisting of SEQ ID NOs: 16-18. In certain embodiments, the light chain variable region comprises the amino acid sequence set forth in SEQ ID NO: 20. In certain embodiments, the heavy chain variable region and the light chain variable region, respectively, comprise the amino acid sequences set forth in SEQ ID NOs: 16 and 19, 17 and 19, 18 and 19, 15 and 20, 16 and 20, 17 and 20, or 18 and 20, respectively.

In another aspect, the instant disclosure provides an isolated antibody (e.g., humanized antibody) that specifically binds to ApoC3, comprising a heavy chain variable region having complementarity determining regions CDRH1, CDRH2 and CDRH3, and a light chain variable region having complementarity determining regions CDRL1, CDRL2 and CDRL3, wherein:
(a) CDRH1 comprises the amino acid sequence of TYSMR (SEQ ID NO: 3);
(b) CDRH2 comprises the amino acid sequence of SIHTX$_1$X$_2$GGTAYRDSVKG, wherein X$_1$ is G, E, or D, and X$_2$ is G or A (SEQ ID NO: 87);
(c) CDRH3 comprises the amino acid sequence of AGYSD (SEQ ID NO: 10);
(d) CDRL1 comprises the amino acid sequence of KTSQGLVHSXGKTYFY, wherein X is D or G (SEQ ID NO: 88);
(e) CDRL2 comprises the amino acid sequence of QVSNRAS (SEQ ID NO: 7); and
(f) CDRL3 comprises the amino acid sequence of AXGTYYPHT, wherein X is Q or H (SEQ ID NO: 8).

In certain embodiments, CDRH2 comprises the amino acid sequence of SIHTGGGGTAYRDSVKG (SEQ ID NO: 36), SIHTEAGGTAYRDSVKG (SEQ ID NO: 37), SIHTDAGGTAYRDSVKG (SEQ ID NO: 38), or SIHTEGGGTAYRDSVKG (SEQ ID NO: 39). In certain embodiments, CDRL1 comprises the amino acid sequence of KTSQGLVHSDGKTYFY (SEQ ID NO: 6) or KTSQGLVHSGGKTYFY (SEQ ID NO: 40). In certain embodiments, CDRL3 comprises the amino acid sequence of AHGTYYPHT (SEQ ID NO: 14) or AQGTYYPHT (SEQ ID NO: 13). In certain embodiments, the CDRH1, CDRH2, CDRH3, CDRL1, CDRL2, and CDRL3 comprise the amino acid sequences set forth in SEQ ID NOs: 3, 36, 10, 6, 7, and 14; 3, 37, 10, 40, 7, and 14; 3, 38, 10, 40, 7, and 14; 3, 38, 10, 6, 7, and 14; 3, 39, 10, 6, 7, and 14; or 3, 37, 10, 40, 7, and 13, respectively.

In another aspect, the instant disclosure provides an isolated antibody (e.g., humanized antibody) that specifically binds to ApoC3, the antibody comprising a heavy chain variable region comprising an amino acid sequence selected from the group consisting of SEQ ID NOs: 42-53.

In another aspect, the instant disclosure provides an isolated antibody (e.g., humanized antibody) that specifically binds to ApoC3, the antibody comprising a light chain variable region comprising an amino acid sequence selected from the group consisting of SEQ ID NOs: 54-65.

In another aspect, the instant disclosure provides an isolated antibody (e.g., humanized antibody) that specifically binds to ApoC3, the antibody comprising a heavy chain variable region and a light chain variable region, wherein the heavy chain variable region and the light chain variable region, respectively, comprise the amino acid sequences set forth in SEQ ID NOs: 42 and 54, 43 and 55, 44 and 56, 45 and 57, 46 and 58, 46 and 54, 47 and 58, 47 and 54, 48 and 58, 48 and 54, 49 and 59, 49 and 60, 50 and 59, 50 and 60, 51 and 61, 52 and 62, 53 and 62, 43 and 63, 44 and 64, or 45 and 65.

In another aspect, the instant disclosure provides an isolated antibody that specifically binds to ApoC3, comprising a heavy chain variable region having complementarity determining regions CDRH1, CDRH2 and CDRH3, and a light chain variable region having complementarity determining regions CDRL1, CDRL2 and CDRL3, wherein:
(a) CDRH1 comprises the amino acid sequence of TYSMR (SEQ ID NO: 3);
(b) CDRH2 comprises the amino acid sequence of SIX$_1$TDGGGTAYRDSVKG, wherein X$_1$ is S or H (SEQ ID NO: 4);
(c) CDRH3 comprises the amino acid sequence of X$_2$GYSD, wherein X$_2$ is A or H (SEQ ID NO: 5);
(d) CDRL1 comprises the amino acid sequence of KTSQGLVHSDGKTYFY (SEQ ID NO: 6);
(e) CDRL2 comprises the amino acid sequence of QVSNRAS (SEQ ID NO: 7); and
(f) CDRL3 comprises the amino acid sequence of AX$_3$GTYYPHT, wherein X$_3$ is Q or H (SEQ ID NO: 8), and wherein at least one of X$_1$, X$_2$, and X$_3$ is H.

In certain embodiments, the CDRH1, CDRH2, CDRH3, CDRL1, CDRL2, and CDRL3 comprise the amino acid sequences set forth in SEQ ID NOs: 3, 11, 10, 6, 7, and 13; 3, 9, 12, 6, 7, and 13; 3, 9, 10, 6, 7, and 14; 3, 11, 10, 6, 7, and 14; 3, 9, 12, 6, 7, and 14; 3, 11, 12, 6, 7, and 13; or 3, 11, 12, 6, 7, and 13, respectively.

In another aspect, the instant disclosure provides an isolated antibody that specifically binds to ApoC3, the antibody comprising a heavy chain variable region comprising an amino acid sequence selected from the group consisting of SEQ ID NOs: 16-18.

In another aspect, the instant disclosure provides an isolated antibody that specifically binds to ApoC3, the antibody comprising a light chain variable region comprising the amino acid sequence set forth in SEQ ID NO: 20.

In another aspect, the instant disclosure provides an isolated antibody that specifically binds to ApoC3, the antibody comprising a heavy chain variable region and a light chain variable region, wherein the heavy chain variable region and the light chain variable region, respectively, comprise the amino acid sequences set forth in SEQ ID NOs: 16 and 19, 17 and 19, 18 and 19, 15 and 20, 16 and 20, 17 and 20, or 18 and 20, respectively.

In certain embodiments of any one of the foregoing aspects, the antibody further comprises a human or humanized constant region. In certain embodiments, the constant region is a variant of a wild type human immunoglobulin heavy chain constant region, and wherein the variant human immunoglobulin heavy chain constant region has an increased affinity for human neonatal Fc receptor (FcRn) at pH 6 relative to the affinity of the wild type human immunoglobulin heavy chain constant region for human FcRn at pH 6. In certain embodiments, the constant region is a heavy chain constant region of a human IgG. In certain embodiments, the constant region is a heavy chain constant region of a human IgG$_1$, IgG$_2$, or IgG$_4$.

In certain embodiments, the constant region comprises the amino acids K, F, and Y at EU positions 433, 434, and 436, respectively. In certain embodiments, the constant region comprises the amino acids Y, T, and E at EU positions 252, 254, and 256, respectively. In certain embodiments, the constant region comprises the amino acids L and S at EU positions 428 and 434, respectively. In certain embodiments, the constant region comprises an amino acid sequence selected from the group consisting of SEQ ID NOs: 22-24, 76-78, and 81-86.

In certain embodiments, the isolated antibody comprises a heavy chain comprising an amino acid sequence selected from the group consisting of SEQ ID NOs: 66-73. In certain embodiments, the isolated antibody comprises a light chain comprising the amino acid sequence set forth in SEQ ID NO: 74. In certain embodiments, the isolated antibody comprises a heavy chain and a light chain, wherein the heavy chain and the light chain, respectively, comprise the amino acid sequences set forth in SEQ ID NOs: 66 and 74, 67 and 74, 68 and 74, 69 and 74, 70 and 74, 71 and 74, 72 and 74, or 73 and 74, respectively.

In another aspect, the instant disclosure provides a pharmaceutical composition comprising an antibody as disclosed herein and a pharmaceutically acceptable carrier.

In another aspect, the instant disclosure provides a polynucleotide encoding the heavy chain variable region or the light chain variable region of an antibody as disclosed herein. In another aspect, the instant disclosure provides an expression vector comprising the polynucleotide as disclosed herein. In another aspect, the instant disclosure provides a host cell comprising the expression vector as disclosed herein.

In another aspect, the instant disclosure provides a method for producing an antibody that binds to ApoC3, the method comprising culturing the host cell as disclosed herein under conditions that allow expression of the antibody.

In another aspect, the instant disclosure provides a method for inhibiting the activity of ApoC3 in a subject, the method comprising administering to the subject an effective amount of an antibody or pharmaceutical composition as disclosed herein. In another aspect, the instant disclosure provides a method for reducing triglyceride levels in the blood of a subject, the method comprising administering to the subject an effective amount of an antibody or pharmaceutical composition as disclosed herein. In another aspect, the instant disclosure provides a method for inhibiting post-prandial lipemia in a subject, the method comprising administering to the subject an effective amount of an antibody or pharmaceutical composition as disclosed herein. In another aspect, the instant disclosure provides a method for treating hypertriglyceridemia in a subject, the method comprising administering to the subject an effective amount of an antibody or pharmaceutical composition as disclosed herein. In another aspect, the instant disclosure provides a method for treating chylomicronemia in a subject, the method comprising administering to the subject an effective amount of an antibody or pharmaceutical composition as disclosed herein.

In another aspect, the instant disclosure provides a method for reducing the risk of cardiovascular disease in a subject with hypertriglyceridemia, the method comprising administering to the subject an effective amount of an antibody or pharmaceutical composition as disclosed herein. In certain embodiments, the cardiovascular disease is myocardial infarction. In certain embodiments, the cardiovascular disease is angina. In certain embodiments, the cardiovascular disease is stroke. In certain embodiments, the cardiovascular disease is atherosclerosis.

In certain embodiments of the foregoing aspects relating to treatment methods, the antibody reduces the levels of chylomicron or chylomicron remnants in the blood of the subject. In certain embodiments, the subject is receiving an additional lipid lowering agent. In certain embodiments, the additional lipid lowering agent is an HMG-CoA reductase inhibitor. In certain embodiments, the HMG-CoA reductase inhibitor is atorvastatin, fluvastatin, lovastatin, pitavastatin, pravastatin, rosuvastatin or simvastatin. In certain embodiments, the additional lipid lowering agent is a PCSK9 inhibitor. In certain embodiments, the PCSK9 inhibitor is alirocumab, evolocumab, or bococizumab. In certain embodiments, the additional lipid lowering agent is ezetimibe. In certain embodiments, the additional lipid lowering agent is a combination of ezetimibe and an HMG-CoA reductase inhibitor. In certain embodiments, the additional lipid lowering agent is a combination of ezetimibe, an HMG-CoA reductase inhibitor, and a PCSK9 inhibitor.

uptake by HepG2 cells. HepG2 cells were incubated with DiI VLDL and purified ApoC3 either alone or in the presence of an anti-ApoC3 antibody as indicated. DiI VLDL ingested by HepG2 cells were measured by fluorescence spectroscopy of the DiI dye. HepG2 cells incubated with DiI VLDL alone ("VLDL") served as a positive control, and HepG2 cells incubated with DiI VLDL and purified ApoC3 in the absence of an anti-ApoC3 antibody ("ApoC3") served as a negative control.

Figure 2A:
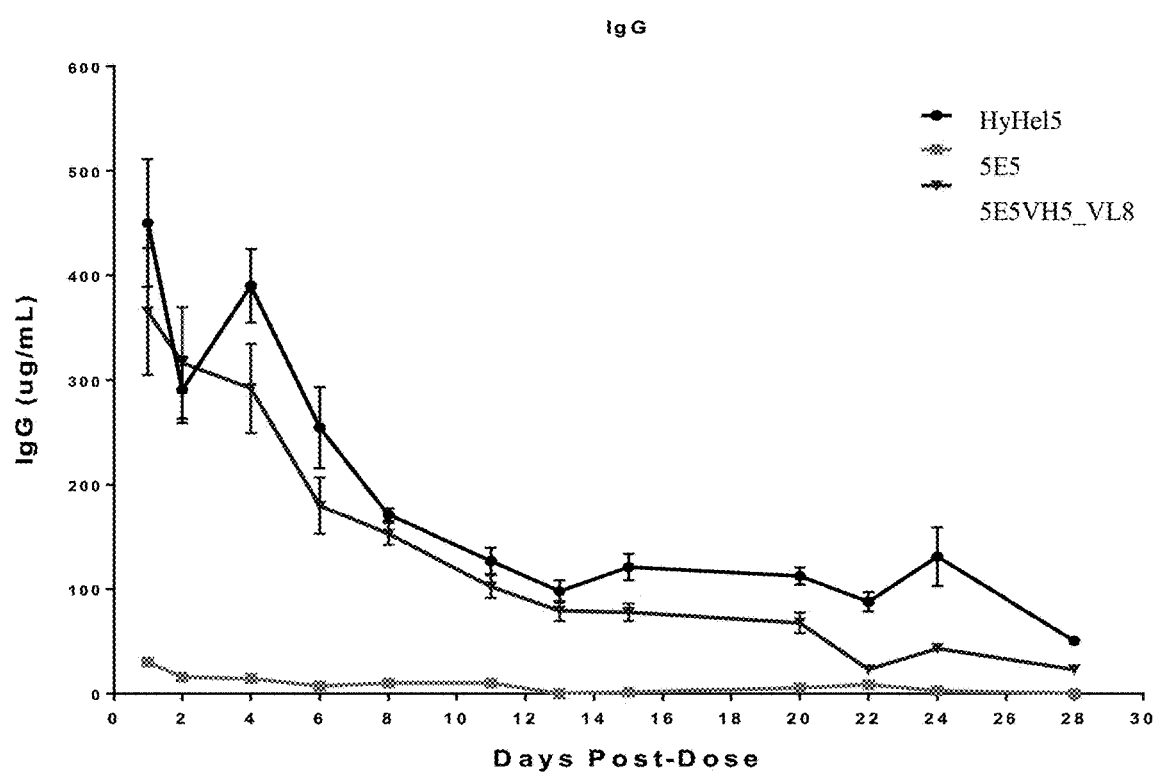

FIG. 2A is a graph showing the serum levels at various times post-injection of two anti-ApoC3 antibodies, 5E5 and 5E5VH5_VL8, and an anti-hen egg lysosome human IgG$_1$ antibody (HyHEL5), in an AAV8-human ApoC3 mouse model.

Figure 2B:
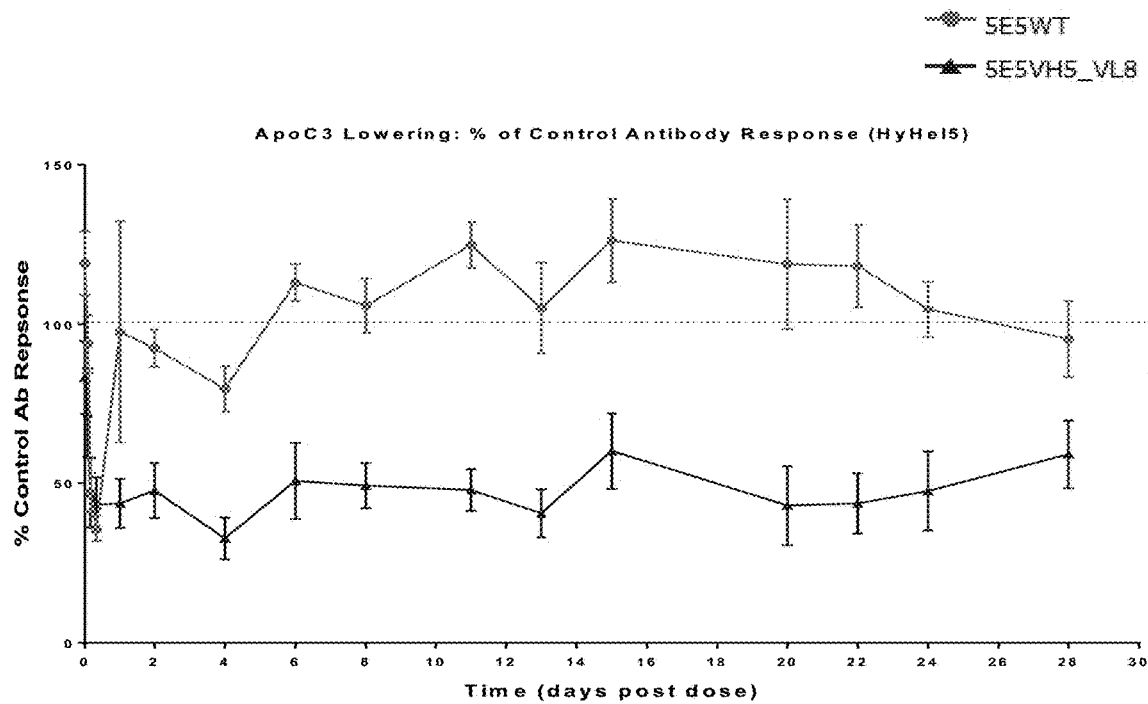

FIG. 2B is a graph showing the effect of 5E5 and 5E5VH5_VL8 on the level of circulating human ApoC3 in an AAV8-human ApoC3 mouse model.

Figure 2C:
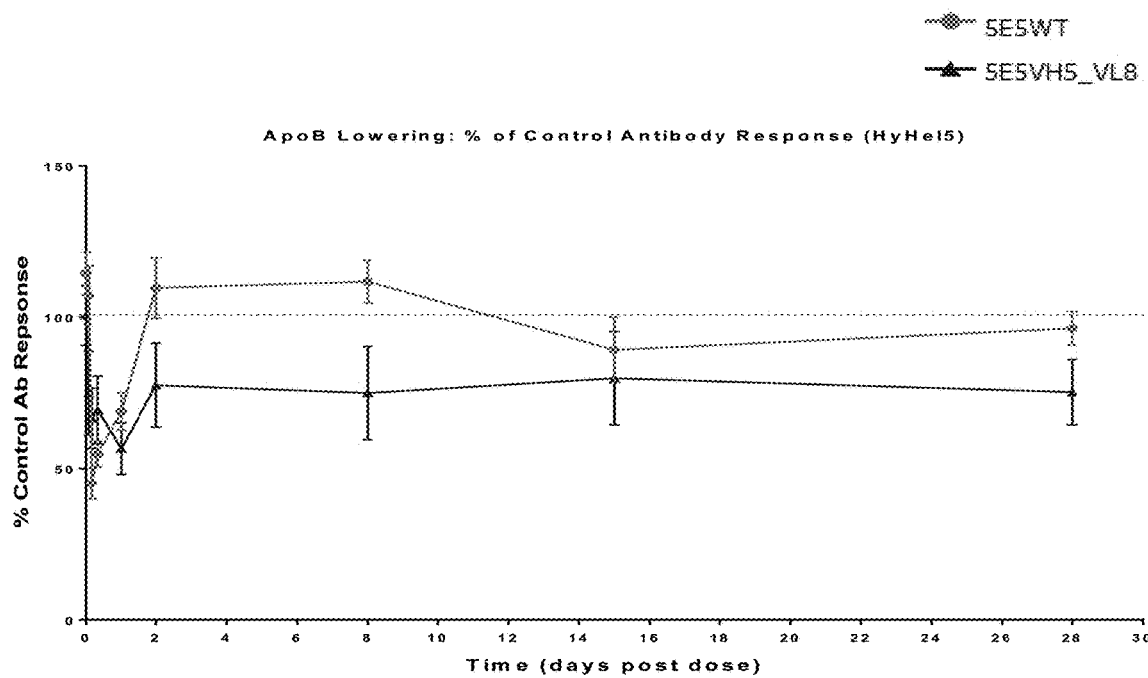

FIG. 2C is a graph showing the effect of 5E5 and 5E5VH5_VL8 on the level of circulating ApoB in an AAV8-human ApoC3 mouse model.

FIGS. 3A-E are a series of surface plasmon resonance (SPR) sensorgrams showing the binding kinetics of twenty humanized anti-ApoC3 antibodies (mAb1 to mAb20) for human ApoC3, when human ApoC3 is immobilized on a biosensor chip. Sensorgrams with dotted and solid lines corresponds to assay pH of 7.4 and 5.5, respectively. For reference, the sensorgrams corresponding to 5E5VH5_VL8 at 25 nM concentration are included in every graph (in dashed line at pH7.4 and in long-dashed line at pH5.5).

FIGS. 4A-E are a series of SPR sensorgrams showing the binding kinetics of twenty humanized anti-ApoC3 antibodies (mAb1 to mAb20) human ApoC3, when the ApoC3 antibodies are immobilized on a biosensor chip. Sensorgrams in dotted and solid line corresponds to assay pH of 7.4 and 5.5, respectively. For reference, the sensorgrams corresponding to 5E5VH5_VL8 at 600 nM target nhuApoC3 concentration are included in every graph (dashed line at pH7.4 and long dashed lines at pH5.5).

Figure 5A:
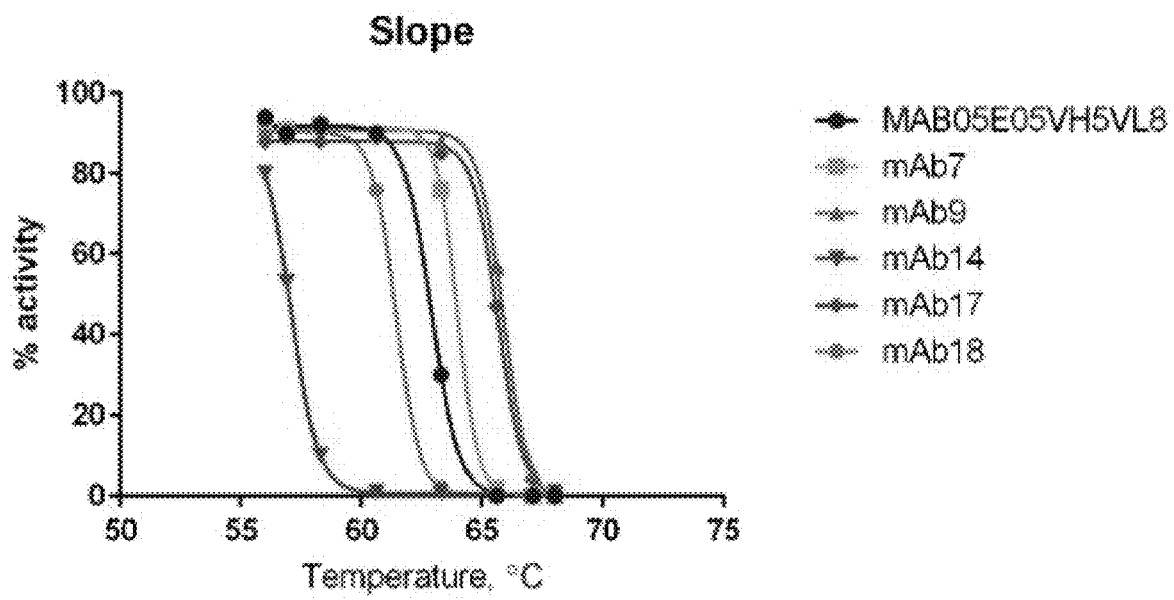
Figure 5B:
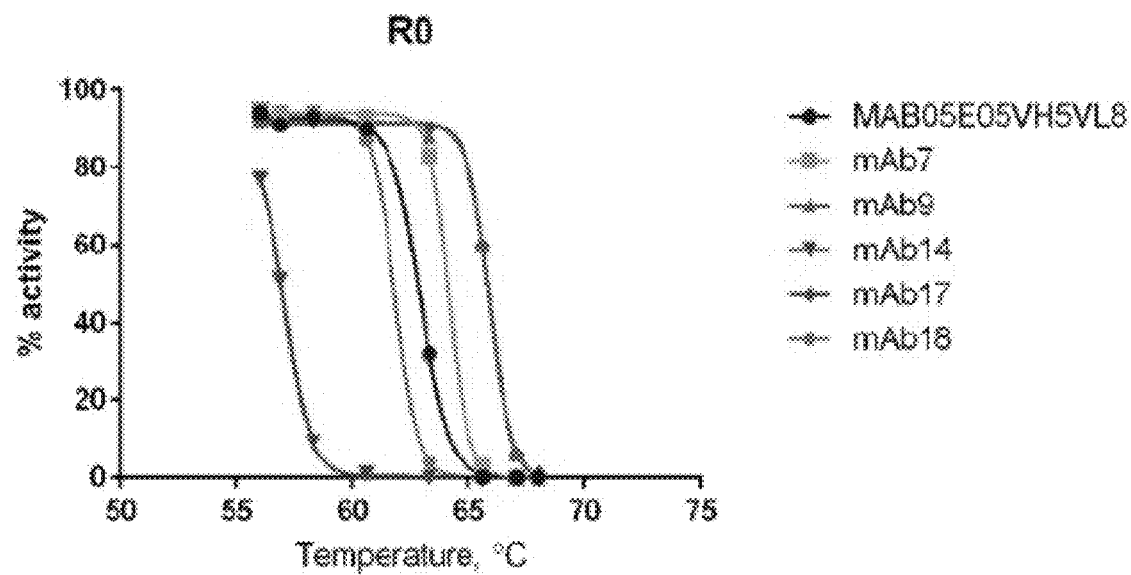
Figure 5C:
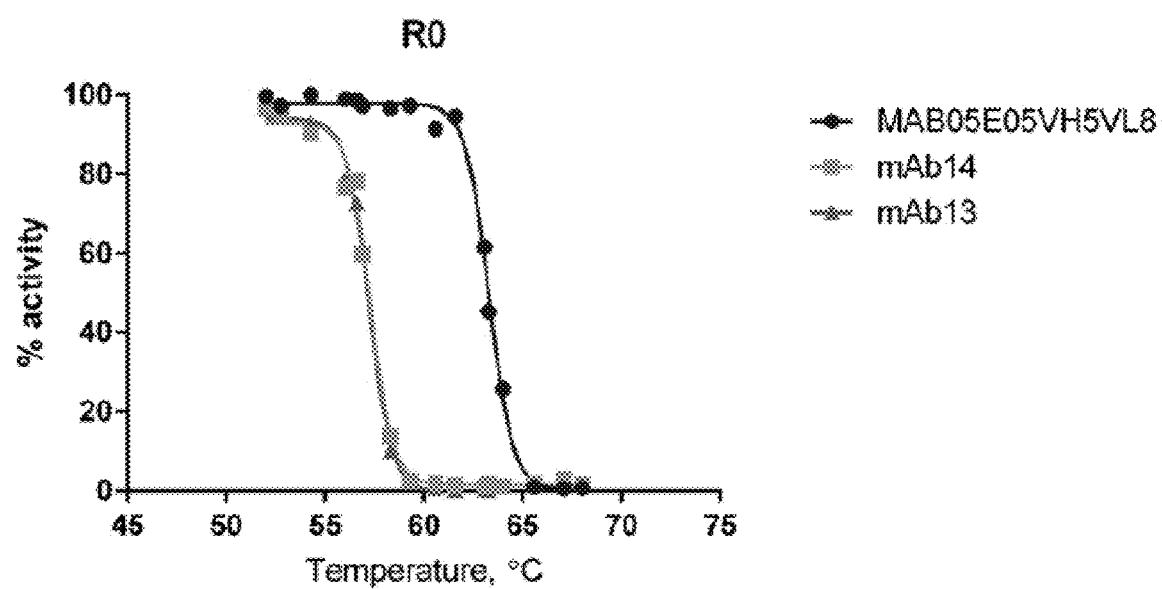

FIGS. 5A-C are graphs showing the percentage activity of selected humanized antibodies and 5E5VH5_VL8 after incubation of the antibodies at the indicated temperatures for 1 hour, relative to the activity of the corresponding antibodies incubated at 4° C. for 1 hour. The activity was measured as the association rate in FIG. 5A, and was measured as the RU maximal value (R0) in FIGS. 5B and 5C.

DETAILED DESCRIPTION

The instant disclosure provides antibodies that specifically bind to ApoC3 (e.g., human ApoC3) and inhibit ApoC3 function. Also provided are pharmaceutical compositions comprising these antibodies, nucleic acids encoding these antibodies, expression vectors and host cells for making these antibodies, and methods of treating a subject using these antibodies. In certain embodiments, the anti-ApoC3 antibodies disclosed herein can attenuate the ability of ApoC3 to inhibit TRL uptake by hepatocytes and can cause a rapid and sustained decrease in the serum levels of ApoC3 and ApoB when administered to a subject. Accordingly, the disclosed anti-ApoC3 antibodies are useful for the treatment and prevention of hypertriglyceridemia and associated diseases (e.g., cardiovascular disease and pancreatitis).

1. Definitions

As used herein, the term "ApoC3" refers to Apolipoprotein C3 protein. In certain embodiments, the ApoC3 is human ApoC3. An exemplary human ApoC3 amino acid sequence is set forth in RefSeq accession number NP_000031.1. The mature amino acid sequence of NP_000031.1 is as follows: SEAEDASLLSFMQGYM-KHATKTAK-DALSSVQESQVAQQARGWVTDGFSSLKDYWST VKDKFSEFWDLDPEVRPTSAVAA (SEQ ID NO: 1).

As used herein, the terms "antibody" and "antibodies" include full length antibodies, antigen-binding fragments of full length antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), scFv-Fcs, camelid antibodies (e.g., llama antibodies), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies disclosed herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies disclosed herein are IgG antibodies, or a class (e.g., human IgG$_1$ or IgG$_4$) or subclass thereof. In a specific embodiment, the antibody is a humanized monoclonal antibody.

As used herein, the term "isolated antibody" refers to an antibody that has been identified and separated and/or recovered from at least one component of its natural environment. The term "isolated antibody" includes an antibody in situ within a recombinant host cell.

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are incorporated by reference in their entireties, where the definitions include overlapping or subsets of amino acid residues when compared against each other. In certain embodiments, the term "CDR" is a CDR as defined by Kabat et al., J. Biol. Chem. 252, 6609-6616 (1977) and Kabat et al., Sequences of protein of immunological interest. (1991). CDRH1, CDRH2 and CDRH3 denote the heavy chain CDRs, and CDRL1, CDRL2 and CDRL3 denote the light chain CDRs.

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha (α), delta (δ), epsilon (ε), gamma (γ), and mu (μ), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

As used herein, the term "EU position" refers to the amino acid position according to the EU numbering convention for the constant regions of an antibody, as described in Edelman, G. M. et al., Proc. Natl. Acad. USA, 63, 78-85 (1969) and Kabat et al., in "Sequences of Proteins of Immunological Interest", U.S. Dept. Health and Human Services, 5th edition, 1991, each of which is herein incorporated by reference in its entirety.

As used herein, the term "specifically binds to" refers to the ability of an antibody to bind to an antigen with a dissociation constant ($K_D$) of less than about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or less, or bind to an antigen with an affinity that is at least two-fold greater than its affinity for a nonspecific antigen.

As used herein, an "epitope" refers to a localized region of an antigen to which an antibody can specifically bind. An epitope can be, for example, contiguous amino acids of a polypeptide (a linear or contiguous epitope) or an epitope can, for example, be formed from two or more non-contiguous regions of a polypeptide or polypeptides (a conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), peptide scanning assays, or mutagenesis mapping (e.g., site-directed mutagenesis mapping).

As used herein, the term "treat," "treating," and "treatment" refer to therapeutic or preventative measures disclosed herein. The methods of "treatment" employ administration of an anti-ApoC3 antibody to a subject having a disease or disorder, or predisposed to having such a disease or disorder, in order to prevent, cure, delay, reduce the severity of, reduce the risk of developing, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal.

As used herein, the term "or" means and/or.

As used herein, the terms "about" and "approximately," when used to modify a numeric value or numeric range, indicate that deviations of 5% to 10% above and 5% to 10% below the value or range remain within the intended meaning of the recited value or range.

2. Anti-ApoC3 Antibodies

The instant disclosure provides isolated antibodies (e.g., humanized antibodies) that specifically bind to ApoC3 (e.g., human ApoC3) and inhibit ApoC3 function.

In certain embodiments, the isolated antibodies bind to ApoC3 protein of a mammal. In certain embodiments, the isolated antibodies bind to human ApoC3. In certain embodiments, the isolated antibodies bind to *Macaca fascicularis* (cynomolgus monkey) ApoC3.

In certain embodiments, the isolated antibodies bind to ApoC3 (e.g., human ApoC3) with a higher affinity at physiological pH (e.g., pH 7.4) than under at acidic pH (e.g., pH 5.5 to pH 6). Methods for generating such pH-dependent antibodies are well known in the art. For example, in one exemplary method, one or more amino residues in the heavy and/or light chain CDRs of an anti-ApoC3 antibody are substituted with a histidine residue, as described in: Igawa et al., Nat Biotechnol. (2010) 28(11):1203-1207; Chaparro-Riggers et al., J Biol Chem. (2012) 287(14):11090-11097; U.S. Pat. No. 9,096,651, and U.S. patent publication number US20110111406A1, each of which is hereby incorporated by reference herein in its entirety. However, although such methods are well known in the art, the skilled worker will appreciate that, for any given antibody, the precise CDR amino acids that can be mutated to histidine to achieve pH-dependent binding to antigen without disrupting the antibody's affinity for antigen can only be determined empirically (see e.g., Edgcomb and Murphy, Proteins (2002) 49:1-6, which is hereby incorporated by reference herein in its entirety).

A skilled person in the art would appreciate that the affinity of an antibody to an antigen can be indicated by the dissociation constant ($K_D$), wherein a smaller $K_D$ indicates a higher affinity. Accordingly, in certain embodiments, the anti-ApoC3 antibodies bind to ApoC3 (e.g., human ApoC3) with a first $K_D$ at pH 7.4 and with a second $K_D$ at pH 5.5, wherein the ratio between the second $K_D$ and the first $K_D$ is at least 1 (e.g., at least 1.1, 1.2, 1.3, 1.4, 1.5, 1.6, 1.7, 1.8, 1.9, 2, 2.5, 3, 3.5, 4, 4.5, 5, 6, 7, 8, 9, 10, 11, 12, 13, 14, 15, 20, 25, 30, 35, 40, 45, 50, 60, 70, 80, 90, or 100).

In certain embodiments, the first $K_D$ is less than 100 nM (e.g., less than 50, 20, 10, 5, 2, 1, 0.5, 0.2, or 0.1 nM). In certain embodiments, the second $K_D$ is greater than 1 nM (e.g., greater than 2, 5, 10, 20, or 50 nM, or greater than 0.1, 0.2, 0.5, 1, 2, 5, 10, 20, 50, or 100 µM). In certain embodiments, the first $K_D$ is less than 100 nM (e.g., less than 50, 20, 10, 5, 2, 1, 0.5, 0.2, or 0.1 nM), and the half-life of the antibody in an animal (e.g., a human or a mouse) expressing ApoC3 (e.g., human ApoC3) is at least about 1 day (e.g., at least about 2, 3, 4, 5, 6, or 7 days, or greater than about 1, 2, 3, 4, 6, or 8 weeks). In certain embodiments, the ApoC3 is human ApoC3, and the animal expressing the ApoC3 is a human. In certain embodiments, the ApoC3 is human ApoC3, and the animal expressing the ApoC3 is a mouse expressing human ApoC3.

In certain embodiments, the isolated antibodies disclosed herein attenuate the ability of ApoC3 to inhibit hepatocyte uptake of TRL (e.g., VLDL) or TRL remnants (in vivo or in vitro). In certain embodiments, the isolated antibodies disclosed herein attenuate the ability of ApoC3 to inhibit hepatocyte uptake of TRL (e.g., VLDL) or TRL remnants by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the isolated antibodies disclosed herein attenuate the ability of ApoC3 to inhibit hepatocyte uptake of TRL (e.g., VLDL) or TRL remnants by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art.

In certain embodiments, the isolated antibodies disclosed herein are capable of inhibiting post-prandial lipemia in a subject when administered to the subject prior to, during, or after a meal. In certain embodiments, the anti-ApoC3 antibodies disclosed herein are capable of inhibiting post-prandial lipemia in the subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the anti-ApoC3 antibodies disclosed herein are capable of inhibiting post-prandial lipemia in the subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art.

In certain embodiments, the isolated antibodies disclosed herein are capable of reducing the levels of post-prandial chylomicron or chylomicron remnants in a subject when administered to the subject prior to, during, or after a meal. In certain embodiments, the anti-ApoC3 antibodies disclosed herein are capable of reducing the levels of post-prandial chylomicron or chylomicron remnants in a subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the anti-ApoC3 antibodies disclosed herein are capable of reducing the levels of post-prandial chylomicron or chylomicron remnants in a subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art.

In certain embodiments, the isolated antibodies disclosed herein are capable of increasing the rates of clearance of ApoC3 and/or ApoB (e.g., ApoB48 and/or ApoB100) from the blood in a subject. In certain embodiments, the anti-ApoC3 antibodies are capable of increasing the rates of clearance of ApoC3 and/or ApoB (e.g., ApoB48 and/or ApoB100) from the blood in a subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the anti-ApoC3 antibodies disclosed herein are capable of increasing the rates of clearance of ApoC3 and/or ApoB (e.g., ApoB48 and/or ApoB100) from the blood in a subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art. Methods for assessing the clearance of ApoC3 and/or ApoB (e.g., ApoB48 and/or ApoB100) include without limitation the isotope tracer techniques, wherein the isotope can be either radioactive or stable.

In certain embodiments, the isolated antibodies disclosed herein are capable of reducing the levels of ApoC3 and/or ApoB (e.g., ApoB48 and/or ApoB100) in the blood in a subject. In certain embodiments, the anti-ApoC3 antibodies are capable of reducing the levels of ApoC3 and/or ApoB (e.g., ApoB48 and/or ApoB100) in the blood in a subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the anti-ApoC3 antibodies disclosed herein are capable of reducing the levels of ApoC3 and/or ApoB (e.g., ApoB48 and/or ApoB100) in the blood in a subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art. In certain embodiments, the reduction in the levels of ApoC3 and/or ApoB (e.g., ApoB48 and/or ApoB100) in the blood in the subject is maintained for at least 1, 2, 3, 4, 5, 6, 7, 8, 9, 10, 15, 20, 25, 30, 35, 40, 45, or 50 days, or at least 1, 2, 3, 4, 5, 6, 7, or 8 weeks.

In certain embodiments, the isolated antibodies disclosed herein are capable of binding to lipid-bound ApoC3 (e.g., ApoC3 bound to triglyceride, TRL (e.g., VLDL) or TRL remnants). In certain embodiments, the isolated antibodies disclosed herein do not inhibit the binding of ApoC3 to a lipid or a lipoprotein. In certain embodiments, the antibodies disclosed herein do not compete for the binding of ApoC3 with a lipid or a lipoprotein. In certain embodiments, the lipid comprises a fatty acid chain. In certain embodiments, the lipid comprises a phosphatidyl group. In certain embodiments, the lipid comprises a phosphatidylcholine (e.g., DMPC), a phosphatidylserine, a phosphatidylethanolamine, a phosphatidylinositol or a phosphatidylglycerol. In certain embodiments, the lipid is a triglyceride. In certain embodiments, the lipoprotein is a TRL (e.g., VLDL) or a TRL remnant. In certain embodiments, the ability of ApoC3 to bind to lipids and lipoproteins (e.g., triglyceride, TRL (e.g., VLDL) or TRL remnants) in the presence of an anti-ApoC3 antibody disclosed herein is at least 50%, 55%, 60%, 65%, 70%, 75%, 80%, 85%, 90%, 95%, 98%, or 99% of the ability of ApoC3 to bind to the same lipids and lipoproteins in the absence of an anti-ApoC3 antibody, as assessed by methods disclosed herein or by methods known to one of skill in the art.

In certain embodiments, the isolated antibodies disclosed herein attenuate the ability of ApoC3 to inhibit hepatocyte uptake of TRL (e.g., VLDL) or TRL remnants. In certain embodiments, the uptake of TRL (e.g., VLDL) or TRL remnants by hepatocytes (e.g., HepG2 cells) in the presence of an anti-ApoC3 antibody as disclosed herein is at least 1.1, 1.2, 1.3, 1.4, 1.5, 1.6, 1.7, 1.8, 1.9, 2, 2.5, 3, 3.5, 4, 4.5, or 5 folds higher than the uptake of TRL (e.g., VLDL) or TRL remnants by hepatocytes (e.g., HepG2 cells) in the absence of an anti-ApoC3 antibody.

In certain embodiments, the isolated antibodies disclosed herein attenuate the ability of ApoC3 to inhibit hepatocyte uptake of TRL (e.g., VLDL) or TRL remnants, and are capable of binding to lipid-bound ApoC3 (e.g., ApoC3 bound to triglyceride, TRL (e.g., VLDL) or TRL remnants).

In certain embodiments, the isolated antibodies disclosed herein bind to an epitope of ApoC3 within the amino acid sequence FSEFWDLDPE (SEQ ID NO: 2). In certain embodiments, the epitope comprises at least one amino acid within SEQ ID NO: 2, and optionally comprises one or more amino acids from SEQ ID NO: 1 contiguous to SEQ ID NO: 2. In certain embodiments, the epitope comprises at least one of the amino acid at position 2, 5, 6, 8, or 10 of SEQ ID NO: 2. In certain embodiments, the epitope comprises at least two of the amino acid at position 2, 5, 6, 8, or 10 of SEQ ID NO: 2. In certain embodiments, the epitope comprises at least three of the amino acid at position 2, 5, 6, 8, or 10 of SEQ ID NO: 2. In certain embodiments, the epitope comprises at least four of the amino acid at position 2, 5, 6, 8, or 10 of SEQ ID NO: 2. In certain embodiments, the epitope comprises the amino acids at positions 5 and 6 of SEQ ID NO: 2. In certain embodiments, the epitope comprises the amino acids at positions 2, 5 and 6 of SEQ ID NO: 2. In certain embodiments, the epitope comprises the amino acids at positions 2, 5 and 8 of SEQ ID NO: 2. In certain embodiments, the epitope comprises the amino acids at positions 2, 5, 6, and 8 of SEQ ID NO: 2. In certain embodiments, the epitope comprises the amino acid at position 10 of SEQ ID NO: 2. In certain embodiments, the epitope comprises the amino acids at positions 6 and 10 of SEQ ID NO: 2. In certain embodiments, the epitope comprises the amino acids at positions 8 and 10 of SEQ ID NO: 2. In certain embodiments, the epitope comprises the amino acids at positions 6 and 8 of SEQ ID NO: 2. In certain embodiments, the epitope comprises the amino acids at positions 6, 8 and 10 of SEQ ID NO: 2. In certain embodiments, the antibodies are capable of binding to lipid-bound ApoC3 (e.g., ApoC3 bound to triglyceride, TRL (e.g., VLDL) or TRL remnants). In certain embodiments, the antibodies are not capable of attenuating the ability of ApoC3 to inhibit lipoprotein lipase-mediated lipolysis of TRL (e.g., VLDL). In certain embodiments, the antibodies also attenuate the ability of ApoC3 to inhibit hepatocyte uptake of TRL (e.g., VLDL) or TRL remnants. In certain embodiments, the antibodies are also capable of inhibiting post-prandial lipemia in a subject when administered to the subject prior to, during, or after a meal. In certain embodiments, the antibodies disclosed herein are also capable of reducing the levels of post-prandial chylomicron or chylomicron remnants in a subject when administered to the subject prior to, during, or after a meal.

Any suitable assays can be used to measure the foregoing functional activities of the antibodies disclosed herein. Exemplary assays include, but are not limited to, the functional assays disclosed in the Examples herein.

The amino acid sequences of exemplary anti-ApoC3 antibodies are set forth in Tables 1-13, herein.

TABLE 1

Heavy chain CDR amino acid sequences of exemplary anti-ApoC3 antibodies.

| VH clone | CDRH1 | SEQ ID NO | CDRH2 | SEQ ID NO | CDRH3 | SEQ ID NO |
|---|---|---|---|---|---|---|
| 5E5VHWT | TYSMR | 3 | SISTDGGGTAYRDSVKG | 9 | AGYSD | 10 |
| 5E5VH5 | TYSMR | 3 | SIHTDGGGTAYRDSVKG | 11 | AGYSD | 10 |
| 5E5VH12 | TYSMR | 3 | SISTDGGGTAYRDSVKG | 9 | HGYSD | 12 |
| 5E5VH5VH12 | TYSMR | 3 | SIHTDGGGTAYRDSVKG | 11 | HGYSD | 12 |

TABLE 2

Light chain CDR amino acid sequences of exemplary anti-ApoC3 antibodies.

| VL clone | CDRL1 | SEQ ID NO | CDRL2 | SEQ ID NO | CDRL3 | SEQ ID NO |
|---|---|---|---|---|---|---|
| 5E5VLWT | KTSQGLVHSDGKTYFY | 6 | QVSNRAS | 7 | AQGTYYPHT | 13 |
| 5E5VL8 | KTSQGLVHSDGKTYFY | 6 | QVSNRAS | 7 | AHGTYYPHT | 14 |

TABLE 3

VH amino acid sequences of exemplary anti-ApoC3 antibodies.

| VH clone | Amino acid Sequence | SEQ ID NO |
|---|---|---|
| 5E5VHWT | QLQLVESGGGLVQPGGSLRLSCAASGFTFGTYSMRWVRQVPRKALEWVSSISTDGGGTAYRDSVKGRFTISRDNAKNTLYLQMNNLKPEDTAIYYCVIAGYSDWGQGTQVTVSS | 15 |
| 5E5VH5 | QLQLVESGGGLVQPGGSLRLSCAASGFTFGTYSMRWVRQVPRKALEWVSSIHTDGGGTAYRDSVKGRFTISRDNAKNTLYLQMNNLKPEDTAIYYCVIAGYSDWGQGTQVTVSS | 16 |

TABLE 3-continued

VH amino acid sequences of exemplary anti-ApoC3 antibodies.

| VH clone | Amino acid Sequence | SEQ ID NO |
|---|---|---|
| 5E5VH12 | QLQLVESGGGLVQPGGSLRLSCAASGFTFGTYSMRWVRQVPRKALEWVSSISTDGGGTAYRDSVKGRFTISRDNAKNTLYLQMNNLKPEDTAIYYCVIHGYSDWGQGTQVTVSS | 17 |
| 5E5VH5VH12 | QLQLVESGGGLVQPGGSLRLSCAASGFTFGTYSMRWVRQVPRKALEWVSSIHTDGGGTAYRDSVKGRFTISRDNAKNTLYLQMNNLKPEDTAIYYCVIHGYSDWGQGTQVTVSS | 18 |

TABLE 4

VL amino acid sequences of exemplary anti-ApoC3 antibodies.

| VL clone | Amino acid Sequence | SEQ ID NO |
|---|---|---|
| 5E5VLWT | ATMLTQSPGSLSVVPGESASISCKTSQGLVHSDGKTYFYWFLQKPGQSPQQLIYQVSNRASGVPDRFTGSGSGTDFTLKISGVKAEDAGVYYCAQGTYYPHTFGSGTRLEIK | 19 |
| 5E5VL8 | ATMLTQSPGSLSVVPGESASISCKTSQGLVHSDGKTYFYWFLQKPGQSPQQLIYQVSNRASGVPDRFTGSGSGTDFTLKISGVKAEDAGVYYCAHGTYYPHTFGSGTRLEIK | 20 |

TABLE 5

VH and VL sequences of exemplary anti-ApoC3 antibodies.

| Antibody | VH | SEQ ID NO | VL | SEQ ID NO |
|---|---|---|---|---|
| 5E5WT | 5E5VHWT | 15 | 5E5VLWT | 19 |
| 5E5VH5_VLWT | 5E5VH5 | 16 | 5E5VLWT | 19 |
| 5E5VH12_VLWT | 5E5VH12 | 17 | 5E5VLWT | 19 |
| 5E5VH5VH12_VLWT | 5E5VH5VH12 | 18 | 5E5VLWT | 19 |
| 5E5VHWT_VL8 | 5E5VHWT | 15 | 5E5VL8 | 20 |
| 5E5VH5_VL8 | 5E5VH5 | 16 | 5E5VL8 | 20 |
| 5E5VH12_VL8 | 5E5VH12 | 17 | 5E5VL8 | 20 |
| 5E5VH5VH12_VL8 | 5E5VH5VH12 | 18 | 5E5VL8 | 20 |

TABLE 6

Sequences of exemplary heavy chain and light chain constant regions.

| Constant Region | Amino Acid Sequence | SEQ ID NO |
|---|---|---|
| Human IgG$_1$ constant region wild-type | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 21 |
| Human IgG$_1$ constant region wild-type | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 75 |
| Human IgG$_1$ constant region YTE | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 22 |
| Human IgG$_1$ constant region YTE | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG | 76 |

TABLE 6-continued

Sequences of exemplary heavy chain and light chain constant regions.

| Constant Region | Amino Acid Sequence | SEQ ID NO |
|---|---|---|
| Human IgG$_1$ constant region NHance | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYN STYRVVSVLTVLHQDWLNGKEYKCKVSNKALPAPIEKTISKAKG QPREPQVYTLPPSRDELTKNQVSLTCLVKGFYPSDIAVEWESNGQ PENNYKTTPPVLDSDGSFFLYSKLTVDKSRWQQGNVFSCSVMHE ALKFHYTQKSLSLSPGK | 23 |
| Human IgG$_1$ constant region NHance | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYN STYRVVSVLTVLHQDWLNGKEYKCKVSNKALPAPIEKTISKAKG QPREPQVYTLPPSRDELTKNQVSLTCLVKGFYPSDIAVEWESNGQ PENNYKTTPPVLDSDGSFFLYSKLTVDKSRWQQGNVFSCSVMHE ALKFHYTQKSLSLSPG | 77 |
| Human IgG$_1$ constant region Xtend | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYN STYRVVSVLTVLHQDWLNGKEYKCKVSNKALPAPIEKTISKAKG QPREPQVYTLPPSRDELTKNQVSLTCLVKGFYPSDIAVEWESNGQ PENNYKTTPPVLDSDGSFFLYSKLTVDKSRWQQGNVFSCSVLHE ALHSHYTQKSLSLSPGK | 24 |
| Human IgG$_1$ constant region Xtend | ASTKGPSVFPLAPSSKSTSGGTAALGCLVKDYFPEPVTVSWNSGA LTSGVHTFPAVLQSSGLYSLSSVVTVPSSSLGTQTYICNVNHKPSN TKVDKKVEPKSCDKTHTCPPCPAPELLGGPSVFLFPPKPKDTLMIS RTPEVTCVVVDVSHEDPEVKFNWYVDGVEVHNAKTKPREEQYN STYRVVSVLTVLHQDWLNGKEYKCKVSNKALPAPIEKTISKAKG QPREPQVYTLPPSRDELTKNQVSLTCLVKGFYPSDIAVEWESNGQ PENNYKTTPPVLDSDGSFFLYSKLTVDKSRWQQGNVFSCSVLHE ALHSHYTQKSLSLSPG | 78 |
| Human IgG$_4$ constant region wild-type | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLFPPKPKDTLMISRT PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVMHEAL HNHYTQKSLSLSLGK | 79 |
| Human IgG$_4$ S228P constant region wild-type | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLFPPKPKDTLMISRT PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVMHEAL HNHYTQKSLSLSLG | 80 |
| Human IgG$_4$ S228P constant region YTE | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLFPPKPKDTLYITRE PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVMHEAL HNHYTQKSLSLSLGK | 81 |
| Human IgG$_4$ S228P constant region YTE | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLFPPKPKDTLYITRE PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVMHEAL HNHYTQKSLSLSLG | 82 |

TABLE 6-continued

Sequences of exemplary heavy chain and light chain constant regions.

| Constant Region | Amino Acid Sequence | SEQ ID NO |
|---|---|---|
| Human IgG$_4$ S228P constant region NHance | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLPPKPKDTLMISRT PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVMHEAL KFHYTQKSLSLSLGK | 83 |
| Human IgG$_4$ S228P constant region NHance | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLPPKPKDTLMISRT PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVMHEAL KFHYTQKSLSLSLG | 84 |
| Human IgG$_4$ S228P constant region Xtend | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLPPKPKDTLMISRT PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVLHEAL HSHYTQKSLSLSLGK | 85 |
| Human IgG$_4$ S228P constant region Xtend | ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLPPKPKDTLMISRT PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVLHEAL HSHYTQKSLSLSLG | 86 |
| Human Igκ constant region | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC | 25 |
| Human Igλ constant region | GQPKANPTVTLFPPSSEELQANKATLVCLISDFYPGAVTVAWKA DGSPVKAGVETTKPSKQSNNKYAASSYLSLTPEQWKSHRSYSCQ VTHEGSTVEKTVAPTECS | 26 |

TABLE 7

Full heavy chain and light chain sequences of exemplary anti-ApoC3 antibodies.

| Antibody chain | Amino Acid Sequence | SEQ ID NO |
|---|---|---|
| 5E5VH5 | QLQLVESGGGLVQPGGSLRLSCAASGFTFGTYSMRWVRQVPRKA LEWVSSIHTDGGGTAYRDSVKGRFTISRDNAKNTLYLQMNNLKPE DTAIYYCVIAGYSDWGQGTQVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVMHEALHNHYTQKSLSLSPGK | 27 |
| 5E5VH5_YTE | QLQLVESGGGLVQPGGSLRLSCAASGFTFGTYSMRWVRQVPRKA LEWVSSIHTDGGGTAYRDSVKGRFTISRDNAKNTLYLQMNNLKPE DTAIYYCVIAGYSDWGQGTQVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPELLGGPSVFLFPPKPKDTLYITREPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSRDELTKNQV | 28 |

TABLE 7-continued

Full heavy chain and light chain sequences of exemplary anti-ApoC3 antibodies.

| Antibody chain | Amino Acid Sequence | SEQ ID NO |
|---|---|---|
| | SLTCLVKGFYPSDIAVEWESNGQPENNYKTTPPVLDSDGSFFLYSK LTVDKSRWQQGNVFSCSVMHEALHNHYTQKSLSLSPGK | |
| 5E5VH5_ NHance | QLQLVESGGGLVQPGGSLRLSCAASGFTFGTYSMRWVRQVPRKA LEWVSSIHTDGGGTAYRDSVKGRFTISRDNAKNTLYLQMNNLKPE DTAIYYCVIAGYSDWGQGTQVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVMHEALKFHYTQKSLSLSPGK | 29 |
| 5E5VH5_ Xtend | QLQLVESGGGLVQPGGSLRLSCAASGFTFGTYSMRWVRQVPRKA LEWVSSIHTDGGGTAYRDSVKGRFTISRDNAKNTLYLQMNNLKPE DTAIYYCVIAGYSDWGQGTQVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVLHEALHSHYTQKSLSLSPGK | 30 |
| 5E5VH12 | QLQLVESGGGLVQPGGSLRLSCAASGFTFGTYSMRWVRQVPRKA LEWVSSISTDGGGTAYRDSVKGRFTISRDNAKNTLYLQMNNLKPE DTAIYYCVIHGYSDWGQGTQVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVMHEALHNHYTQKSLSLSPGK | 31 |
| 5E5VH12_ YTE | QLQLVESGGGLVQPGGSLRLSCAASGFTFGTYSMRWVRQVPRKA LEWVSSISTDGGGTAYRDSVKGRFTISRDNAKNTLYLQMNNLKPE DTAIYYCVIHGYSDWGQGTQVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPELLGGPSVFLFPPKPKDTLYITREPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVMHEALHNHYTQKSLSLSPGK | 32 |
| 5E5VH12_ NHance | QLQLVESGGGLVQPGGSLRLSCAASGFTFGTYSMRWVRQVPRKA LEWVSSISTDGGGTAYRDSVKGRFTISRDNAKNTLYLQMNNLKPE DTAIYYCVIHGYSDWGQGTQVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVMHEALKFHYTQKSLSLSPGK | 33 |
| 5E5VH12_ Xtend | QLQLVESGGGLVQPGGSLRLSCAASGFTFGTYSMRWVRQVPRKA LEWVSSISTDGGGTAYRDSVKGRFTISRDNAKNTLYLQMNNLKPE DTAIYYCVIHGYSDWGQGTQVTVSSASTKGPSVFPLAPSSKSTSGG TAALGCLVKDYFPEPVTVSWNSGALTSGVHTFPAVLQSSGLYSLS SVVTVPSSSLGTQTYICNVNHKPSNTKVDKKVEPKSCDKTHTCPP CPAPELLGGPSVFLFPPKPKDTLMISRTPEVTCVVVDVSHEDPEVK FNWYVDGVEVHNAKTKPREEQYNSTYRVVSVLTVLHQDWLNGK EYKCKVSNKALPAPIEKTISKAKGQPREPQVYTLPPSRDELTKNQV SLTCLVKGFYPSDIAVEWESNGQPENNYKTTPPVLDSDGSFFLYSK LTVDKSRWQQGNVFSCSVLHEALHSHYTQKSLSLSPGK | 34 |

TABLE 7-continued

Full heavy chain and light chain sequences of exemplary anti-ApoC3 antibodies.

| Antibody chain | Amino Acid Sequence | SEQ ID NO |
|---|---|---|
| 5E5VL8_ full light chain | ATMLTQSPGSLSVVPGESASISCKTSQGLVHSDGKTYFYWFLQKP GQSPQQLIYQVSNRASGVPDRFTGSGSGTDFTLKISGVKAEDAGV YYCAHGTYYPHTFGSGTRLEIKRTVAAPSVFIFPPSDEQLKSGTAS VVCLLNNFYPREAKVQWKVDNALQSGNSQESVTEQDSKDSTYSL SSTLTLSKADYEKHKVYACEVTHQGLSSPVTKSFNRGEC | 35 |

The amino acid sequences of exemplary humanized anti-ApoC3 antibodies are set forth in Tables 8-13, herein.

TABLE 8

Heavy chain CDR amino acid sequences of exemplary humanized anti-ApoC3 antibodies.

| VH clone | CDRH1 | SEQ ID NO | CDRH2 | SEQ ID NO | CDRH3 | SEQ ID NO |
|---|---|---|---|---|---|---|
| VH CDR consensus | TYSMR | 3 | SIHTX$_1$X$_2$GGTAYRDS VKG, wherein X$_1$ is, G, E or D, and X$_2$ is G or A | 87 | AGYSD | 10 |
| mAb7_VH | TYSMR | 3 | SIHTGGGGTAYRDSVKG | 36 | AGYSD | 10 |
| mAb1_VH | TYSMR | 3 | SIHTEGGGTAYRDSVKG | 39 | AGYSD | 10 |
| mAb2_VH | TYSMR | 3 | SIHTEGGGTAYRDSVKG | 39 | AGYSD | 10 |
| mAb3_VH | TYSMR | 3 | SIHTEGGGTAYRDSVKG | 39 | AGYSD | 10 |
| mAb4_VH | TYSMR | 3 | SIHTEGGGTAYRDSVKG | 39 | AGYSD | 10 |
| mAb5_VH | TYSMR | 3 | SIHTEGGGTAYRDSVKG | 39 | AGYSD | 10 |
| mAb6_VH | TYSMR | 3 | SIHTEGGGTAYRDSVKG | 39 | AGYSD | 10 |
| mAb8_VH | TYSMR | 3 | SIHTDAGGTAYRDSVKG | 38 | AGYSD | 10 |
| mAb9_VH | TYSMR | 3 | SIHTDAGGTAYRDSVKG | 38 | AGYSD | 10 |
| mAb10_VH | TYSMR | 3 | SIHTEGGGTAYRDSVKG | 39 | AGYSD | 10 |
| mAb11_VH | TYSMR | 3 | SIHTEGGGTAYRDSVKG | 39 | AGYSD | 10 |
| mAb12_VH | TYSMR | 3 | SIHTDAGGTAYRDSVKG | 38 | AGYSD | 10 |
| mAb13_VH | TYSMR | 3 | SIHTEGGGTAYRDSVKG | 39 | AGYSD | 10 |
| mAb14_VH | TYSMR | 3 | SIHTEGGGTAYRDSVKG | 39 | AGYSD | 10 |
| mAb15_VH | TYSMR | 3 | SIHTEAGGTAYRDSVKG | 37 | AGYSD | 10 |
| mAb16_VH | TYSMR | 3 | SIHTEAGGTAYRDSVKG | 37 | AGYSD | 10 |
| mAb17_VH | TYSMR | 3 | SIHTEAGGTAYRDSVKG | 37 | AGYSD | 10 |
| mAb18_VH | TYSMR | 3 | SIHTEAGGTAYRDSVKG | 37 | AGYSD | 10 |
| mAb19_VH | TYSMR | 3 | SIHTDAGGTAYRDSVKG | 38 | AGYSD | 10 |
| mAb20_VH | TYSMR | 3 | SIHTDAGGTAYRDSVKG | 38 | AGYSD | 10 |

TABLE 9

Light chain CDR amino acid sequences of exemplary humanized anti-ApoC3 antibodies.

| VL clone | CDRL1 | SEQ ID NO | CDRL2 | SEQ ID NO | CDRL3 | SEQ ID NO |
|---|---|---|---|---|---|---|
| VL CDR consensus | KTSQGLVHSXGKTYFY, wherein X is D or G | 88 | QVSNRAS | 7 | AXGTYYPHT, wherein X is Q or H | 8 |
| mAb7_VL | KTSQGLVHSDGKTYFY | 6 | QVSNRAS | 7 | AHGTYYPHT | 14 |
| mAb1_VL | KTSQGLVHSDGKTYFY | 6 | QVSNRAS | 7 | AHGTYYPHT | 14 |
| mAb2_VL | KTSQGLVHSDGKTYFY | 6 | QVSNRAS | 7 | AHGTYYPHT | 14 |
| mAb3_VL | KTSQGLVHSDGKTYFY | 6 | QVSNRAS | 7 | AHGTYYPHT | 14 |
| mAb4_VL | KTSQGLVHSDGKTYFY | 6 | QVSNRAS | 7 | AHGTYYPHT | 14 |
| mAb5_VL | KTSQGLVHSDGKTYFY | 6 | QVSNRAS | 7 | AHGTYYPHT | 14 |
| mAb6_VL | KTSQGLVHSDGKTYFY | 6 | QVSNRAS | 7 | AHGTYYPHT | 14 |
| mAb8_VL | KTSQGLVHSDGKTYFY | 6 | QVSNRAS | 7 | AHGTYYPHT | 14 |
| mAb9_VL | KTSQGLVHSDGKTYFY | 6 | QVSNRAS | 7 | AHGTYYPHT | 14 |
| mAb10_VL | KTSQGLVHSDGKTYFY | 6 | QVSNRAS | 7 | AHGTYYPHT | 14 |
| mAb11_VL | KTSQGLVHSDGKTYFY | 6 | QVSNRAS | 7 | AHGTYYPHT | 14 |
| mAb12_VL | KTSQGLVHSDGKTYFY | 6 | QVSNRAS | 7 | AHGTYYPHT | 14 |
| mAb13_VL | KTSQGLVHSDGKTYFY | 6 | QVSNRAS | 7 | AHGTYYPHT | 14 |
| mAb14_VL | KTSQGLVHSDGKTYFY | 6 | QVSNRAS | 7 | AHGTYYPHT | 14 |
| mAb15_VL | KTSQGLVHSGGKTYFY | 40 | QVSNRAS | 7 | AQGTYYPHT | 13 |
| mAb16_VL | KTSQGLVHSGGKTYFY | 40 | QVSNRAS | 7 | AHGTYYPHT | 14 |
| mAb17_VL | KTSQGLVHSGGKTYFY | 40 | QVSNRAS | 7 | AQGTYYPHT | 13 |
| mAb18_VL | KTSQGLVHSGGKTYFY | 40 | QVSNRAS | 7 | AHGTYYPHT | 14 |
| mAb19_VL | KTSQGLVHSGGKTYFY | 40 | QVSNRAS | 7 | AQGTYYPHT | 13 |
| mAb20_VL | KTSQGLVHSGGKTYFY | 40 | QVSNRAS | 7 | AHGTYYPHT | 14 |

TABLE 10

VH amino acid sequences of exemplary humanized anti-ApoC3 antibodies.

| VH clone | Amino acid Sequence | SEQ ID NO |
|---|---|---|
| VH consensus | QLX$_1$ESGGGLVQPGGSLRLSCAASGFTFX$_2$TYSMRWVRQX$_3$PGKGLEWVSSIHTX$_4$X$_5$GGTAYRDSVKGRFTISRDNX$_6$KNTLYLQMNX$_7$LX$_8$X$_9$EDTAX$_{10}$YYCVIAGYSDWGQGTX$_{11}$VTVSS, wherein<br>X$_1$ is V or L;<br>X$_2$ is G or S;<br>X$_3$ is V or A;<br>X$_4$ is G, E, or D;<br>X$_5$ is G or A;<br>X$_6$ is A or S;<br>X$_7$ is S or N;<br>X$_8$ is R or K;<br>X$_9$ is A or P;<br>X$_{10}$ is I or V; and<br>X$_{11}$ is L or Q | 89 |

TABLE 10-continued

VH amino acid sequences of exemplary humanized anti-ApoC3 antibodies.

| VH clone | Amino acid Sequence | SEQ ID NO |
|---|---|---|
| VH consensus | QLVESGGGLVQPGGSLRLSCAASGFTFX$_1$TYSMRWVRQX$_2$PGKGLEWVSSIHTX$_3$X$_4$GGTAYRDSVKGRFTISRDNAKNTLYLQMNX$_5$LX$_6$X$_7$EDTAX$_8$YYCVIAGYSDWGQGTX$_9$VTVSS, wherein<br>X$_1$ is G or S;<br>X$_2$ is V or A;<br>X$_3$ is G, E, or D;<br>X$_4$ is G or A;<br>X$_5$ is S or N;<br>X$_6$ is R or K;<br>X$_7$ is A or P;<br>X$_8$ is I or V; and<br>X$_9$ is L or Q | 90 |
| mAb1_VH, mAb2_VH | QLVESGGGLVQPGGSLRLSCAASGFTFGTYSMRWVRQVPGKGLEWVSSIHTEGGTAYRDSVKGRFTISRDNAKNTLYLQMNSLRAEDTAIYYCVIAGYSDWGQGTLVTVSS | 46 |
| mAb3_VH, mAb4_VH | QLVESGGGLVQPGGSLRLSCAASGFTFGTYSMRWVRQAPGKGLEWVSSIHTEGGTAYRDSVKGRFTISRDNAKNTLYLQMNSLRAEDTAIYYCVIAGYSDWGQGTLVTVSS | 47 |
| mAb5_VH, mAb6_VH | QLVESGGGLVQPGGSLRLSCAASGFTFGTYSMRWVRQAPGKGLEWVSSIHTEGGTAYRDSVKGRFTISRDNAKNTLYLQMNSLRAEDTAVYYCVIAGYSDWGQGTLVTVSS | 48 |
| mAb7_VH | QLVESGGGLVQPGGSLRLSCAASGFTFSTYSMRWVRQAPGKGLEWVSSIHTGGGTAYRDSVKGRFTISRDNAKNTLYLQMNNLRAEDTAIYYCVIAGYSDWGQGTLVTVSS | 42 |
| mAb8_VH, mAb9_VH | QLVESGGGLVQPGGSLRLSCAASGFTFSTYSMRWVRQAPGKGLEWVSSIHTDAGGTAYRDSVKGRFTISRDNAKNTLYLQMNNLRAEDTAVYYCVIAGYSDWGQGTLVTVSS | 49 |
| mAb10_VH, mAb11_VH | QLVESGGGLVQPGGSLRLSCAASGFTFSTYSMRWVRQVPGKGLEWVSSIHTEGGTAYRDSVKGRFTISRDNAKNTLYLQMNNLRAEDTAVYYCVIAGYSDWGQGTLVTVSS | 50 |
| mAb12_VH | QLVESGGGLVQPGGSLRLSCAASGFTFSTYSMRWVRQVPGKGLEWVSSIHTDAGGTAYRDSVKGRFTISRDNAKNTLYLQMNSLRPEDTAIYYCVIAGYSDWGQGTLVTVSS | 51 |
| mAb13_VH | QLLESGGGLVQPGGSLRLSCAASGFTFSTYSMRWVRQVPGKGLEWVSSIHTEGGTAYRDSVKGRFTISRDNSKNTLYLQMNSLRAEDTAVYYCVIAGYSDWGQGTLVTVSS | 52 |
| mAb14_VH | QLLESGGGLVQPGGSLRLSCAASGFTFGTYSMRWVRQVPGKGLEWVSSIHTEGGTAYRDSVKGRFTISRDNSKNTLYLQMNSLRAEDTAVYYCVIAGYSDWGQGTLVTVSS | 53 |
| mAb15_VH, mAb16_VH | QLVESGGGLVQPGGSLRLSCAASGFTFGTYSMRWVRQAPGKGLEWVSSIHTEAGGTAYRDSVKGRFTISRDNAKNTLYLQMNNLKAEDTAIYYCVIAGYSDWGQGTQVTVSS | 43 |
| mAb17_VH, mAb18_VH | QLVESGGGLVQPGGSLRLSCAASGFTFSTYSMRWVRQAPGKGLEWVSSIHTEAGGTAYRDSVKGRFTISRDNAKNTLYLQMNNLRAEDTAVYYCVIAGYSDWGQGTLVTVSS | 44 |
| mAb19_VH, mAb20_VH | QLVESGGGLVQPGGSLRLSCAASGFTFSTYSMRWVRQAPGKGLEWVSSIHTDAGGTAYRDSVKGRFTISRDNAKNTLYLQMNNLRPEDTAVYYCVIAGYSDWGQGTLVTVSS | 45 |

TABLE 11

VL amino acid sequences of exemplary humanized anti-ApoC3 antibodies.

| VL clone | Amino acid Sequence | SEQ ID NO |
|---|---|---|
| VL consensus | DIVMTQSPX$_1$SLX$_2$VX$_3$PGESASISCKTSQGLVHSX$_4$GKTYFY WFLQKPGQSPQX$_5$LIYQVSNRASGVPDRFX$_6$GSGSGTDFTLK ISX$_7$V X$_8$AEDX$_9$GVYYCAX$_{10}$GTYYPHTFGX$_{11}$GTRLEIK, wherein<br>X$_1$ is L or G;<br>X$_2$ is P or S;<br>X$_3$ is T or V;<br>X$_4$ is D or G;<br>X$_5$ is Q or L;<br>X$_6$ is S or T;<br>X$_7$ is R or G;<br>X$_8$ is K or E;<br>X$_9$ is A or V;<br>X$_{10}$ is H or Q; and<br>X$_{11}$ is Q or S | 91 |
| VL consensus | DIVMTQSPX$_1$SLX$_2$VX$_3$PGESASISCKTSQGLVHSX$_4$GKTYFY WFLQKPGQSPQQLIYQVSNRASGVPDRFX$_5$GSGSGTDFTLKI SX$_6$V X$_7$AEDX$_8$GVYYCAX$_9$GTYYPHTFGX$_{10}$GTRLEIK, wherein<br>X$_1$ is L or G;<br>X$_2$ is P or S;<br>X$_3$ is T or V;<br>X$_4$ is D or G;<br>X$_5$ is S or T;<br>X$_6$ is R or G;<br>X$_7$ is K or E;<br>X$_8$ is A or V;<br>X$_9$ is H or Q; and<br>X$_{10}$ is Q or S | 92 |
| mAb1_VL, mAb3_VL, mAb5_VL | DIVMTQSPLSLPVTPGESASISCKTSQGLVHSDGKTYFYWFL QKPGQSPQQLIYQVSNRASGVPDRFTGSGSGTDFTLKISRVK AEDAGVYYCAHGTYYPHTFGQGTRLEIK | 58 |
| mAb2_VL, mAb4_VL, mAb6_VL, mAb7_VL | DIVMTQSPLSLPVTPGESASISCKTSQGLVHSDGKTYFYWFL QKPGQSPQQLIYQVSNRASGVPDRFSGSGSGTDFTLKISRVK AEDAGVYYCAHGTYYPHTFGQGTRLEIK | 54 |
| mAb8_VL, mAb10_VL | DIVMTQSPLSLSVVPGEPASISCKTSQGLVHSDGKTYFYWFL QKPGQSPQQLIYQVSNRASGVPDRFSGSGSGTDFTLKISRVE AEDVGVYYCAHGTYYPHTFGQGTRLEIK | 59 |
| mAb9_VL, mAb11_VL | DIVMTQSPLSLSVTPGEPASISCKTSQGLVHSDGKTYFYWFL QKPGQSPQQLIYQVSNRASGVPDRFSGSGSGTDFTLKISRVE AEDVGVYYCAHGTYYPHTFGQGTRLEIK | 60 |
| mAb12_VL | DIVMTQSPLSLSVTPGEPASISCKTSQGLVHSDGKTYFYWFL QKPGQSPQQLIYQVSNRASGVPDRFTGSGSGTDFTLKISRVK AEDVGVYYCAHGTYYPHTFGQGTRLEIK | 61 |
| mAb13_VL, mAb14_VL | DIVMTQSPLSLPVTPGEPASISCKTSQGLVHSDGKTYFYWYL QKPGQSPQLLIYQVSNRASGVPDRFSGSGSGTDFTLKISRVE AEDVGVYYCAHGTYYPHTFGQGTRLEIK | 62 |
| mAb15_VL | DIVMTQSPLSLPVTPGESASISCKTSQGLVHSGGKTYFYWFL QKPGQSPQQLIYQVSNRASGVPDRFTGSGSGTDFTLKISRVE AEDAGVYYCAQGTYYPHTFGSGTRLEIK | 63 |
| mAb16_VL | DIVMTQSPLSLPVTPGESASISCKTSQGLVHSGGKTYFYWFL QKPGQSPQQLIYQVSNRASGVPDRFTGSGSGTDFTLKISRVE AEDAGVYYCAHGTYYPHTFGSGTRLEIK | 55 |
| mAb17_VL | DIVMTQSPLSLPVTPGEPASISCKTSQGLVHSGGKTYFYWFL QKPGQSPQQLIYQVSNRASGVPDRFTGSGSGTDFTLKISRVE AEDAGVYYCAQGTYYPHTFGQGTRLEIK | 64 |
| mAb18_VL | DIVMTQSPLSLPVTPGEPASISCKTSQGLVHSGGKTYFYWFL QKPGQSPQQLIYQVSNRASGVPDRFTGSGSGTDFTLKISRVE AEDAGVYYCAHGTYYPHTFGQGTRLEIK | 56 |

TABLE 11-continued

VL amino acid sequences of exemplary humanized anti-ApoC3 antibodies.

| VL clone | Amino acid Sequence | SEQ ID NO |
|---|---|---|
| mAb19_VL | DIVMTQSPGSLSVTPGEPASISCKTSQGLVHSGGKTYFYWFL QKPGQSPQQLIYQVSNRASGVPDRFTGSGSGTDFTLKISGVE AEDAGVYYCAQGTYYPHTFGQGTRLEIK | 65 |
| mAb20_VL | DIVMTQSPGSLSVTPGEPASISCKTSQGLVHSGGKTYFYWFL QKPGQSPQQLIYQVSNRASGVPDRFTGSGSGTDFTLKISGVE AEDAGVYYCAHGTYYPHTFGQGTRLEIK | 57 |

TABLE 12

VH and VL sequences of exemplary humanized anti-ApoC3 antibodies.

| Antibody | VH | SEQ ID NO | VL | SEQ ID NO |
|---|---|---|---|---|
| mAb1 | mAb1_VH | 46 | mAb1_VL | 58 |
| mAb2 | mAb2_VH | 46 | mAb2_VL | 54 |
| mAb3 | mAb3_VH | 47 | mAb3_VL | 58 |
| mAb4 | mAb4_VH | 47 | mAb4_VL | 54 |
| mAb5 | mAb5_VH | 48 | mAb5_VL | 58 |
| mAb6 | mAb6_VH | 48 | mAb6_VL | 54 |
| mAb7 | mAb7_VH | 42 | mAb7_VL | 54 |
| mAb8 | mAb8_VH | 49 | mAb8_VL | 59 |
| mAb9 | mAb9_VH | 49 | mAb9_VL | 60 |
| mAb10 | mAb10_VH | 50 | mAb10_VL | 59 |
| mAb11 | mAb11_VH | 50 | mAb11_VL | 60 |
| mAb12 | mAb12_VH | 51 | mAb12_VL | 61 |
| mAb13 | mAb13_VH | 52 | mAb13_VL | 62 |
| mAb14 | mAb14_VH | 53 | mAb14_VL | 62 |
| mAb15 | mAb15_VH | 43 | mAb15_VL | 63 |
| mAb16 | mAb16_VH | 43 | mAb16_VL | 55 |
| mAb17 | mAb17_VH | 44 | mAb17_VL | 64 |
| mAb18 | mAb18_VH | 44 | mAb18_VL | 56 |
| mAb19 | mAb19_VH | 45 | mAb19_VL | 65 |
| mAb20 | mAb20_VH | 45 | mAb20_VL | 57 |

TABLE 13

Full heavy chain and light chain sequences of exemplary humanized anti-ApoC3 antibodies.

| Antibody chain | Amino Acid Sequence | SEQ ID NO |
|---|---|---|
| mAb7 heavy chain IgG$_1$ | QLVESGGGLVQPGGSLRLSCAASGFTFSTYSMRWVRQAPGKGLE WVSSIHTGGGGTAYRDSVKGRFTISRDNAKNTLYLQMNNLRAED TAIYYCVIAGYSDWGQGTLVTVSSASTKGPSVFPLAPSSKSTSGGT AALGCLVKDYFPEPVTVSWNSGALTSGVHTFPAVLQSSGLYSLSS VVTVPSSSLGTQTYICNVNHKPSNTKVDKKVEPKSCDKTHTCPPC PAPELLGGPSVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPSRDELTKNQVS LTCLVKGFYPSDIAVEWESNGQPENNYKTTPPVLDSDGSFFLYSKL TVDKSRWQQGNVFSCSVMHEALHNHYTQKSLSLSPG | 66 |
| mAb7 heavy chain IgG$_1$ Xtend | QLVESGGGLVQPGGSLRLSCAASGFTFSTYSMRWVRQAPGKGLE WVSSIHTGGGGTAYRDSVKGRFTISRDNAKNTLYLQMNNLRAED TAIYYCVIAGYSDWGQGTLVTVSSASTKGPSVFPLAPSSKSTSGGT AALGCLVKDYFPEPVTVSWNSGALTSGVHTFPAVLQSSGLYSLSS VVTVPSSSLGTQTYICNVNHKPSNTKVDKKVEPKSCDKTHTCPPC PAPELLGGPSVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPSRDELTKNQVS LTCLVKGFYPSDIAVEWESNGQPENNYKTTPPVLDSDGSFFLYSKL TVDKSRWQQGNVFSCSVLHEALHSHYTQKSLSLSPG | 67 |
| mAb7 heavy chain IgG$_1$ NHance | QLVESGGGLVQPGGSLRLSCAASGFTFSTYSMRWVRQAPGKGLE WVSSIHTGGGGTAYRDSVKGRFTISRDNAKNTLYLQMNNLRAED TAIYYCVIAGYSDWGQGTLVTVSSASTKGPSVFPLAPSSKSTSGGT AALGCLVKDYFPEPVTVSWNSGALTSGVHTFPAVLQSSGLYSLSS VVTVPSSSLGTQTYICNVNHKPSNTKVDKKVEPKSCDKTHTCPPC PAPELLGGP SVFLFPPKPKDTLMISRTPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPSRDELTKNQVS LTCLVKGFYPSDIAVEWESNGQPENNYKTTPPVLDSDGSFFLYSKL TVDKSRWQQGNVFSCSVMHEALKFHYTQKSLSLSPG | 68 |

TABLE 13-continued

Full heavy chain and light chain sequences of exemplary humanized anti-ApoC3 antibodies.

| Antibody chain | Amino Acid Sequence | SEQ ID NO |
|---|---|---|
| mAb7 heavy chain IgG1 YTE | QLVESGGGLVQPGGSLRLSCAASGFTFSTYSMRWVRQAPGKGLE WVSSIHTGGGGTAYRDSVKGRFTISRDNAKNTLYLQMNNLRAED TAIYYCVIAGYSDWGQGTLVTVSSASTKGPSVFPLAPSSKSTSGGT AALGCLVKDYFPEPVTVSWNSGALTSGVHTFPAVLQSSGLYSLSS VVTVPSSSLGTQTYICNVNHKPSNTKVDKKVEPKSCDKTHTCPPC PAPELLGGPSVFLFPPKPKDTLYITREPEVTCVVVDVSHEDPEVKF NWYVDGVEVHNAKTKPREEQYNSTYRVVSVLTVLHQDWLNGKE YKCKVSNKALPAPIEKTISKAKGQPREPQVYTLPPSRDELTKNQVS LTCLVKGFYPSDIAVEWESNGQPENNYKTTPPVLDSDGSFFLYSKL TVDKSRWQQGNVFSCSVMHEALHNHYTQKSLSLSPG | 69 |
| mAb7 heavy chain IgG4 S228P | QLVESGGGLVQPGGSLRLSCAASGFTFSTYSMRWVRQAPGKGLE WVSSIHTGGGGTAYRDSVKGRFTISRDNAKNTLYLQMNNLRAED TAIYYCVIAGYSDWGQGTLVTVSSASTKGPSVFPLAPCSRSTSEST AALGCLVKDYFPEPVTVSWNSGALTSGVHTFPAVLQSSGLYSLSS VVTVPSSSLGTKTYTCNVDHKPSNTKVDKRVESKYGPPCPPCPAP EFLGGPSVFLFPPKPKDTLMISRTPEVTCVVVDVSQEDPEVQFNWY VDGVEVHNAKTKPREEQFNSTYRVVSVLTVLHQDWLNGKEYKC KVSNKGLPSSIEKTISKAKGQPREPQVYTLPPSQEEMTKNQVSLTC LVKGFYPSDIAVEWESNGQPENNYKTTPPVLDSDGSFFLYSRLTV DKSRWQEGNVFSCSVMHEALHNHYTQKSLSLSLG | 70 |
| mAb7 heavy chain IgG4 S228P Xtend | QLVESGGGLVQPGGSLRLSCAASGFTFSTYSMRWVRQAPGKGLE WVSSIHTGGGGTAYRDSVKGRFTISRDNAKNTLYLQMNNLRAED TAIYYCVIAGYSDWGQGTLVTVSSASTKGPSVFPLAPCSRSTSEST AALGCLVKDYFPEPVTVSWNSGALTSGVHTFPAVLQSSGLYSLSS VVTVPSSSLGTKTYTCNVDHKPSNTKVDKRVESKYGPPCPPCPAP EFLGGPSVFLFPPKPKDTLMISRTPEVTCVVVDVSQEDPEVQFNWY VDGVEVHNAKTKPREEQFNSTYRVVSVLTVLHQDWLNGKEYKC KVSNKGLPSSIEKTISKAKGQPREPQVYTLPPSQEEMTKNQVSLTC LVKGFYPSDIAVEWESNGQPENNYKTTPPVLDSDGSFFLYSRLTV DKSRWQEGNVFSCSVLHEALHSHYTQKSLSLSLG | 71 |
| mAb7 heavy chain IgG4 S228P NHance | QLVESGGGLVQPGGSLRLSCAASGFTFSTYSMRWVRQAPGKGLE WVSSIHTGGGGTAYRDSVKGRFTISRDNAKNTLYLQMNNLRAED TAIYYCVIAGYSDWGQGTLVTVSSASTKGPSVFPLAPCSRSTSEST AALGCLVKDYFPEPVTVSWNSGALTSGVHTFPAVLQSSGLYSLSS VVTVPSSSLGTKTYTCNVDHKPSNTKVDKRVESKYGPPCPPCPAP EFLGGPSVFLFPPKPKDTLMISRTPEVTCVVVDVSQEDPEVQFNWY VDGVEVHNAKTKPREEQFNSTYRVVSVLTVLHQDWLNGKEYKC KVSNKGLPSSIEKTISKAKGQPREPQVYTLPPSQEEMTKNQVSLTC LVKGFYPSDIAVEWESNGQPENNYKTTPPVLDSDGSFFLYSRLTV DKSRWQEGNVFSCSVMHEALKFHYTQKSLSLSLG | 72 |
| mAb7 heavy chain IgG4 S228P YTE | QLVESGGGLVQPGGSLRLSCAASGFTFSTYSMRWVRQAPGKGLE WVSSIHTGGGGTAYRDSVKGRFTISRDNAKNTLYLQMNNLRAED TAIYYCVIAGYSDWGQGTLVTVSSASTKGPSVFPLAPCSRSTSEST AALGCLVKDYFPEPVTVSWNSGALTSGVHTFPAVLQSSGLYSLSS VVTVPSSSLGTKTYTCNVDHKPSNTKVDKRVESKYGPPCPPCPAP EFLGGPSVFLFPPKPKDTLYITREPEVTCVVVDVSQEDPEVQFNWY VDGVEVHNAKTKPREEQFNSTYRVVSVLTVLHQDWLNGKEYKC KVSNKGLPSSIEKTISKAKGQPREPQVYTLPPSQEEMTKNQVSLTC LVKGFYPSDIAVEWESNGQPENNYKTTPPVLDSDGSFFLYSRLTV DKSRWQEGNVFSCSVMHEALHNHYTQKSLSLSLG | 73 |
| mAb7 light chain Igκ | DIVMTQSPLSLPVTPGESASISCKTSQGLVHSDGKTYFYWFLQKPG QSPQQLIYQVSNRASGVPDRFSGSGSGTDFTLKISRVKAEDAGVY YCAHGTYYPHTFGQGTRLEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC | 74 |

In certain embodiments, the instant disclosure provides an isolated antibody that specifically binds to ApoC3 (e.g., human ApoC3), the antibody comprising a VH domain comprising one, two, or all three of the CDRs of a VH domain set forth in Table 3 or 10 herein. In certain embodiments, the antibody comprises the CDRH1 of one of VH domains set forth in Table 3 or 10. In certain embodiments, the antibody comprises the CDRH2 of one of the VH domains set forth in Table 3 or 10. In certain embodiments, the antibody comprises the CDRH3 of one of the VH domains set forth in Table 3 or 10.

In certain embodiments, the instant disclosure provides an isolated antibody that specifically binds to ApoC3 (e.g., human ApoC3), the antibody comprising a VL domain comprising one, two, or all three of the CDRs of a VL domain disclosed in Table 4 or 11 herein. In certain embodiments, the antibody comprises the CDRL1 of one of VL domains set forth in Table 4 or 11. In certain embodiments, the antibody comprises the CDRL2 of one of the VL domains set forth in Table 4 or 11. In certain embodiments, the antibody comprises the CDRL3 of one of the VL domains set forth in Table 4 or 11.

In certain embodiments, the instant disclosure provides an isolated antibody that specifically binds to ApoC3 (e.g., human ApoC3), the antibody comprising a heavy chain variable region having complementarity determining regions CDRH1, CDRH2 and CDRH3, and a light chain variable region having complementarity determining regions CDRL1, CDRL2 and CDRL3, wherein CDRH1, CDRH2, CDRH3, CDRL1, CDRL2, and CDRL3 comprise the amino acid sequences of the CDRH1, CDRH2, CDRH3, CDRL1, CDRL2, and CDRL3 regions, respectively, of an antibody set forth in Tables 5 or 12.

In certain embodiments, the CDRs of an antibody can be determined according to Kabat et al., J. Biol. Chem. 252, 6609-6616 (1977) and Kabat et al., Sequences of protein of immunological interest (1991). In certain embodiments, the light chain CDRs of an antibody are determined according to Kabat and the heavy chain CDRs of an antibody are determined according to MacCallum (supra).

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212. According to the IMGT numbering scheme, CDRH1 is at positions 26 to 35, CDRH2 is at positions 51 to 57, CDRH3 is at positions 93 to 102, CDRL1 is at positions 27 to 32, CDRL2 is at positions 50 to 52, and CDRL3 is at positions 89 to 97.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.).

In certain embodiments, the CDRs of an antibody can be determined according to MacCallum R M et al., (1996) J Mol Biol 262: 732-745. See also, e.g., Martin A. "Protein Sequence and Structure Analysis of Antibody Variable Domains," in Antibody Engineering, Kontermann and Dübel, eds., Chapter 31, pp. 422-439, Springer-Verlag, Berlin (2001).

In certain embodiments, the instant disclosure provides an isolated antibody that specifically binds to ApoC3 (e.g., human ApoC3), wherein the antibody comprises a heavy chain variable region comprising the CDRH1, CDRH2, and CDRH3 region amino acid sequences of a VH domain set forth in Table 3, and a light chain variable region comprising the CDRL1, CDRL2, and CDRL3 region amino acid sequences of a VL domain set forth in Table 4, wherein each CDR is independently defined in accordance with the Kabat, Chothia, IMGT, MacCallum, or AbM definition of a CDR, as disclosed herein.

In certain embodiments, the instant disclosure provides an isolated antibody (e.g., a humanized antibody) that specifically binds to ApoC3 (e.g., human ApoC3), the antibody comprising a heavy chain variable region having complementarity determining regions CDRH1, CDRH2 and CDRH3, and a light chain variable region having complementarity determining regions CDRL1, CDRL2 and CDRL3, wherein:

(a) CDRH1 comprises the amino acid sequence of TYSMR (SEQ ID NO: 3);

(b) CDRH2 comprises the amino acid sequence of SIX$_1$TX$_2$X$_3$GGTAYRDSVKG, wherein X$_1$ is S or H, X$_2$ is G, E, or D, and X$_3$ is G or A (SEQ ID NO: 93);

(c) CDRH3 comprises the amino acid sequence of X$_4$GYSD, wherein X$_4$ is A or H (SEQ ID NO: 5);

(d) CDRL1 comprises the amino acid sequence of KTSQGLVHSX$_5$GKTYFY, wherein X$_5$ is D or G (SEQ ID NO: 88);

(e) CDRL2 comprises the amino acid sequence of QVSNRAS (SEQ ID NO: 7); and (f) CDRL3 comprises the amino acid sequence of AX$_6$GTYYPHT, wherein X$_6$ is Q or H (SEQ ID NO: 8), and wherein at least one of X$_1$, X$_4$, and X$_6$ is H.

In certain embodiments, CDRH2 comprises the amino acid sequence of

```
                                      (SEQ ID NO: 36)
SIHTGGGGTAYRDSVKG, (SEQ ID NO: 37)
SIHTEAGGTAYRDSVKG, (SEQ ID NO: 38)
SIHTDAGGTAYRDSVKG, (SEQ ID NO: 39)
SIHTEGGGTAYRDSVKG, (SEQ ID NO: 9)
SISTDGGGTAYRDSVKG,
or (SEQ ID NO: 11)
SIHTDGGGTAYRDSVKG.
```

In certain embodiments, CDRH3 comprises the amino acid sequence of AGYSD (SEQ ID NO: 10) or HGYSD (SEQ ID NO: 12).

In certain embodiments, CDRL1 comprises the amino acid sequence of

```
KTSQGLVHSDGKTYFY                        (SEQ ID NO: 6)
or

KTSQGLVHSGGKTYFY.                       (SEQ ID NO: 40)
```

In certain embodiments, CDRL3 comprises the amino acid sequence of

```
AHGTYYPHT                               (SEQ ID NO: 14)
or

AQGTYYPHT.                              (SEQ ID NO: 13)
```

In certain embodiments, the instant disclosure provides an isolated antibody (e.g., a humanized antibody) that specifically binds to ApoC3 (e.g., human ApoC3), wherein the antibody comprises a VH domain comprising the CDRH1, CDRH2 and CDRH3 amino acid sequences set forth in SEQ ID NOs: 3, 36, and 10; 3, 37, and 10; 3, 38, and 10; 3, 39, and 10; 3, 9, and 10; 3, 11, and 10; 3, 9, and 12; or 3, 11, and 12, respectively.

In certain embodiments, the instant disclosure provides an isolated antibody that specifically binds to ApoC3 (e.g., human ApoC3), wherein the antibody comprises a VL domain comprising the CDRL1, CDRL2 and CDRL3 amino acid sequences set forth in SEQ ID NOs: 6, 7, and 14; 40, 7, and 14; 40, 7, and 13; or 6, 7, and 13, respectively.

In certain embodiments, the instant disclosure provides an isolated antibody (e.g., a humanized antibody) that specifically binds to ApoC3 (e.g., human ApoC3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 42, 43, 44, 45, 46, 47, 48, 49, 50, 51, 52, 53, 15, 16, 17, or 18. In certain embodiments, the antibody comprises a heavy chain variable region having the amino acid sequence set forth in SEQ ID NO: 42, 43, 44, 45, 46, 47, 48, 49, 50, 51, 52, 53, 15, 16, 17, or 18.

In certain embodiments, the instant disclosure provides an isolated antibody (e.g., a humanized antibody) that specifically binds to ApoC3 (e.g., human ApoC3), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 54, 55, 56, 57, 58, 59, 60, 61, 62, 63, 64, 65, 19, or 20. In certain embodiments, the antibody comprises a light chain variable region having the amino acid sequence set forth in SEQ ID NO: 54, 55, 56, 57, 58, 59, 60, 61, 62, 63, 64, 65, 19, or 20.

In certain embodiments, the instant disclosure provides an isolated antibody (e.g., a humanized antibody) that specifically binds to ApoC3 (e.g., human ApoC3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 42, 43, 44, 45, 46, 47, 48, 49, 50, 51, 52, 53, 15, 16, 17, or 18, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 54, 55, 56, 57, 58, 59, 60, 61, 62, 63, 64, 65, 19, or 20. In certain embodiments, the antibody comprises a heavy chain variable region having the amino acid sequence set forth in SEQ ID NO: 42, 43, 44, 45, 46, 47, 48, 49, 50, 51, 52, 53, 15, 16, 17, or 18, and a light chain variable region having the amino acid sequence set forth in SEQ ID NO: 54, 55, 56, 57, 58, 59, 60, 61, 62, 63, 64, 65, 19, or 20.

In certain embodiments, the instant disclosure provides an isolated antibody (e.g., a humanized antibody) that specifically binds to ApoC3 (e.g., human ApoC3), the antibody comprising a heavy chain variable region having complementarity determining regions CDRH1, CDRH2 and CDRH3, and a light chain variable region having complementarity determining regions CDRL1, CDRL2 and CDRL3, wherein:
(a) CDRH1 comprises the amino acid sequence of TYSMR (SEQ ID NO: 3);
(b) CDRH2 comprises the amino acid sequence of SIHTX$_1$X$_2$GGTAYRDSVKG, wherein X$_1$ is G, E, or D, and X$_2$ is G or A (SEQ ID NO: 87);
(c) CDRH3 comprises the amino acid sequence of AGYSD (SEQ ID NO: 10);
(d) CDRL1 comprises the amino acid sequence of KTSQGLVHSXGKTYFY, wherein X is D or G (SEQ ID NO: 88);
(e) CDRL2 comprises the amino acid sequence of QVSNRAS (SEQ ID NO: 7); and
(f) CDRL3 comprises the amino acid sequence of AXGTYYPHT, wherein X is Q or H (SEQ ID NO: 8).

In certain embodiments, the instant disclosure provides an isolated antibody (e.g., a humanized antibody) that specifically binds to ApoC3 (e.g., human ApoC3), the antibody comprising a heavy chain variable region having complementarity determining regions CDRH1, CDRH2 and CDRH3, and a light chain variable region having complementarity determining regions CDRL1, CDRL2 and CDRL3, wherein:
(a) CDRH1 comprises the amino acid sequence of TYSMR (SEQ ID NO: 3);
(b) CDRH2 comprises the amino acid sequence of SIHTGGGGTAYRDSVKG (SEQ ID NO: 36), SIHTEAGGTAYRDSVKG (SEQ ID NO: 37), SIHTDAGGTAYRDSVKG (SEQ ID NO: 38), or SIHTEGGGTAYRDSVKG (SEQ ID NO: 39);
(c) CDRH3 comprises the amino acid sequence of AGYSD (SEQ ID NO: 10);
(d) CDRL1 comprises the amino acid sequence of KTSQGLVHSDGKTYFY (SEQ ID NO: 6) or KTSQGLVHSGGKTYFY (SEQ ID NO: 40);
(e) CDRL2 comprises the amino acid sequence of QVSNRAS (SEQ ID NO: 7); and
(f) CDRL3 comprises the amino acid sequence of AHGTYYPHT (SEQ ID NO: 14) or

```
AQGTYYPHT.                              (SEQ ID NO: 13)
```

In certain embodiments, CDRH2 comprises the amino acid sequence of

```
SIHTGGGGTAYRDSVKG,                      (SEQ ID NO: 36)

SIHTEAGGTAYRDSVKG,                      (SEQ ID NO: 37)
```

-continued

```
SIHTDAGGTAYRDSVKG,                             (SEQ ID NO: 38)
or (SEQ ID NO: 39)
SIHTEGGGTAYRDSVKG.
```

In certain embodiments, CDRH2 comprises the amino acid sequence of SIHTGGGGTAYRDSVKG (SEQ ID NO: 36), SIHTEAGGTAYRDSVKG (SEQ ID NO: 37), or SIHTDAGGTAYRDSVKG (SEQ ID NO: 38). In certain embodiments, CDRH2 comprises the amino acid sequence of SIHTGGGGTAYRDSVKG (SEQ ID NO: 36). In certain embodiments, CDRH2 comprises the amino acid sequence of SIHTEAGGTAYRDSVKG (SEQ ID NO: 37). In certain embodiments, CDRH2 comprises the amino acid sequence of SIHTDAGGTAYRDSVKG (SEQ ID NO: 38). In certain embodiments, CDRH2 comprises the amino acid sequence of SIHTEGGGTAYRDSVKG (SEQ ID NO: 39).

In certain embodiments, CDRL1 comprises the amino acid sequence of KTSQGLVHSDGKTYFY (SEQ ID NO: 6) or KTSQGLVHSGGKTYFY (SEQ ID NO: 40). In certain embodiments, CDRL1 comprises the amino acid sequence of KTSQGLVHSDGKTYFY (SEQ ID NO: 6). In certain embodiments, CDRL1 comprises the amino acid sequence of

```
                                               (SEQ ID NO: 40)
KTSQGLVHSGGKTYFY.
```

In certain embodiments, CDRL3 comprises the amino acid sequence of AHGTYYPHT (SEQ ID NO: 14) or AQGTYYPHT (SEQ ID NO: 13). In certain embodiments, CDRL3 comprises the amino acid sequence of AHGTYYPHT (SEQ ID NO: 14). In certain embodiments, CDRL3 comprises the amino acid sequence of AQGTYYPHT (SEQ ID NO: 13). In certain embodiments, the instant disclosure provides an isolated antibody (e.g., a humanized antibody) that specifically binds to ApoC3 (e.g., human ApoC3), wherein the antibody comprises a VH domain comprising the CDRH1, CDRH2 and CDRH3 amino acid sequences set forth in SEQ ID NOs: 3, 36, and 10; 3, 37, and 10; 3, 38, and 10; or 3, 39, and 10, respectively. In certain embodiments, the VH domain comprises the CDRH1, CDRH2 and CDRH3 amino acid sequences set forth in SEQ ID NOs: 3, 36, and 10, respectively. In certain embodiments, the VH domain comprises the CDRH1, CDRH2 and CDRH3 amino acid sequences set forth in SEQ ID NOs: 3, 37, and 10, respectively. In certain embodiments, the VH domain comprises the CDRH1, CDRH2 and CDRH3 amino acid sequences set forth in SEQ ID NOs: 3, 38, and 10, respectively.

In certain embodiments, the instant disclosure provides an isolated antibody that specifically binds to ApoC3 (e.g., human ApoC3), wherein the antibody comprises a VL domain comprising the CDRL1, CDRL2 and CDRL3 amino acid sequences set forth in SEQ ID NOs: 6, 7, and 14; 40, 7, and 14; or 40, 7, and 13, respectively. In certain embodiments, the VL domain comprises the CDRL1, CDRL2 and CDRL3 amino acid sequences set forth in SEQ ID NOs: 6, 7, and 14, respectively. In certain embodiments, the VL domain comprises the CDRL1, CDRL2 and CDRL3 amino acid sequences set forth in SEQ ID NOs: 40, 7, and 14, respectively.

In certain embodiments, the instant disclosure provides an isolated antibody (e.g., a humanized antibody) that specifically binds to ApoC3 (e.g., human ApoC3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 3, 36, 10, 6, 7, and 14; 3, 37, 10, 40, 7, and 14; 3, 38, 10, 40, 7, and 14; 3, 39, 10, 6, 7, and 14; 3, 37, 10, 40, 7, and 13; or 3, 38, 10, 40, 7, and 13, respectively. In certain embodiments, the CDRH1, CDRH2, CDRH3, CDRL1, CDRL2, and CDRL3 regions comprise the amino acid sequences set forth in SEQ ID NOs: 3, 36, 10, 6, 7, and 14, respectively. In certain embodiments, the CDRH1, CDRH2, CDRH3, CDRL1, CDRL2, and CDRL3 regions comprise the amino acid sequences set forth in SEQ ID NOs: 3, 37, 10, 40, 7, and 14, respectively. In certain embodiments, the CDRH1, CDRH2, CDRH3, CDRL1, CDRL2, and CDRL3 regions comprise the amino acid sequences set forth in SEQ ID NOs: 3, 38, 10, 40, 7, and 14, respectively.

In certain embodiments, the instant disclosure provides an isolated antibody (e.g., a humanized antibody) that specifically binds to ApoC3 (e.g., human ApoC3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 42, 43, 44, 45, 46, 47, 48, 49, 50, 51, 52, 53, 89, or 90. In certain embodiments, the antibody comprises a heavy chain variable region having the amino acid sequence set forth in SEQ ID NO: 42, 43, 44, 45, 46, 47, 48, 49, 50, 51, 52, 53, 89, or 90. In certain embodiments, the antibody comprises a heavy chain variable region having the amino acid sequence set forth in SEQ ID NO: 42. In certain embodiments, the antibody comprises a heavy chain variable region having the amino acid sequence set forth in SEQ ID NO: 43. In certain embodiments, the antibody comprises a heavy chain variable region having the amino acid sequence set forth in SEQ ID NO: 44. In certain embodiments, the antibody comprises a heavy chain variable region having the amino acid sequence set forth in SEQ ID NO: 45. In certain embodiments, the antibody comprises a heavy chain variable region having the amino acid sequence set forth in SEQ ID NO: 46. In certain embodiments, the antibody comprises a heavy chain variable region having the amino acid sequence set forth in SEQ ID NO: 47. In certain embodiments, the antibody comprises a heavy chain variable region having the amino acid sequence set forth in SEQ ID NO: 48. In certain embodiments, the antibody comprises a heavy chain variable region having the amino acid sequence set forth in SEQ ID NO: 49. In certain embodiments, the antibody comprises a heavy chain variable region having the amino acid sequence set forth in SEQ ID NO: 50. In certain embodiments, the antibody comprises a heavy chain variable region having the amino acid sequence set forth in SEQ ID NO: 51. In certain embodiments, the antibody comprises a heavy chain variable region having the amino acid sequence set forth in SEQ ID NO: 52. In certain embodiments, the antibody comprises a heavy chain variable region having the amino acid sequence set forth in SEQ ID NO: 53. In certain embodiments, the antibody comprises a heavy chain variable region having the amino acid sequence set forth in SEQ ID NO: 89, optionally wherein the heavy chain variable region does not comprise the amino acid sequence set forth in SEQ ID NO: 15, 16, 17, or 18. In certain embodiments, the antibody comprises a heavy chain variable region having the amino acid sequence set forth in SEQ ID NO: 90, optionally wherein the heavy chain variable region does not comprise the amino acid sequence set forth in SEQ ID NO: 15, 16, 17, or 18.

In certain embodiments, the instant disclosure provides an isolated antibody (e.g., a humanized antibody) that specifically binds to ApoC3 (e.g., human ApoC3), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 54, 55, 56, 57, 58, 59, 60, 61, 62, 63, 64, 65, 91, or 92. In certain embodiments, the antibody comprises a light chain variable region having the amino acid sequence set forth in SEQ ID NO: 54, 55, 56, 57, 58, 59, 60, 61, 62, 63, 64, 65, 91, or 92. In certain embodiments, the antibody comprises a light chain variable region having the amino acid sequence set forth in SEQ ID NO: 54. In certain embodiments, the antibody comprises a light chain variable region having the amino acid sequence set forth in SEQ ID NO: 55. In certain embodiments, the antibody comprises a light chain variable region having the amino acid sequence set forth in SEQ ID NO: 56. In certain embodiments, the antibody comprises a light chain variable region having the amino acid sequence set forth in SEQ ID NO: 57. In certain embodiments, the antibody comprises a light chain variable region having the amino acid sequence set forth in SEQ ID NO: 58. In certain embodiments, the antibody comprises a light chain variable region having the amino acid sequence set forth in SEQ ID NO: 59. In certain embodiments, the antibody comprises a light chain variable region having the amino acid sequence set forth in SEQ ID NO: 60. In certain embodiments, the antibody comprises a light chain variable region having the amino acid sequence set forth in SEQ ID NO: 61. In certain embodiments, the antibody comprises a light chain variable region having the amino acid sequence set forth in SEQ ID NO: 62. In certain embodiments, the antibody comprises a light chain variable region having the amino acid sequence set forth in SEQ ID NO: 63. In certain embodiments, the antibody comprises a light chain variable region having the amino acid sequence set forth in SEQ ID NO: 64. In certain embodiments, the antibody comprises a light chain variable region having the amino acid sequence set forth in SEQ ID NO: 65. In certain embodiments, the antibody comprises a light chain variable region having the amino acid sequence set forth in SEQ ID NO: 91. In certain embodiments, the antibody comprises a light chain variable region having the amino acid sequence set forth in SEQ ID NO: 92.

In certain embodiments, the instant disclosure provides an isolated antibody (e.g., a humanized antibody) that specifically binds to ApoC3 (e.g., human ApoC3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 42, 43, 44, 45, 46, 47, 48, 49, 50, 51, 52, 53, 89, or 90, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 54, 55, 56, 57, 58, 59, 60, 61, 62, 63, 64, 65, 91, or 92. In certain embodiments, the antibody comprises a heavy chain variable region having the amino acid sequence set forth in SEQ ID NO: 42, 43, 44, 45, 46, 47, 48, 49, 50, 51, 52, 53, 89, or 90, and a light chain variable region having the amino acid sequence set forth in SEQ ID NO: 54, 55, 56, 57, 58, 59, 60, 61, 62, 63, 64, 65, 91, or 92. In certain embodiments, the antibody comprises a heavy chain variable region and light chain variable region having the amino acid sequences set forth in SEQ ID NOs: 42 and 54, 43 and 55, 44 and 56, 45 and 57, 46 and 58, 46 and 54, 47 and 58, 47 and 54, 48 and 58, 48 and 54, 49 and 59, 49 and 60, 50 and 59, 50 and 60, 51 and 61, 52 and 62, 53 and 62, 43 and 63, 44 and 64, 45 and 65, 89 and 91, or 90 and 92, respectively. In certain embodiments, the antibody comprises a heavy chain variable region and light chain variable region having the amino acid sequences set forth in SEQ ID NO: 42 and 54, respectively. In certain embodiments, the antibody comprises a heavy chain variable region and light chain variable region having the amino acid sequences set forth in SEQ ID NO: 43 and 55, respectively. In certain embodiments, the antibody comprises a heavy chain variable region and light chain variable region having the amino acid sequences set forth in SEQ ID NO: 44 and 56, respectively. In certain embodiments, the antibody comprises a heavy chain variable region and light chain variable region having the amino acid sequences set forth in SEQ ID NO: 45 and 57, respectively. In certain embodiments, the antibody comprises a heavy chain variable region and light chain variable region having the amino acid sequences set forth in SEQ ID NO: 46 and 58, respectively. In certain embodiments, the antibody comprises a heavy chain variable region and light chain variable region having the amino acid sequences set forth in SEQ ID NO: 46 and 54, respectively. In certain embodiments, the antibody comprises a heavy chain variable region and light chain variable region having the amino acid sequences set forth in SEQ ID NO: 47 and 58, respectively. In certain embodiments, the antibody comprises a heavy chain variable region and light chain variable region having the amino acid sequences set forth in SEQ ID NO: 47 and 54, respectively. In certain embodiments, the antibody comprises a heavy chain variable region and light chain variable region having the amino acid sequences set forth in SEQ ID NO: 48 and 58, respectively. In certain embodiments, the antibody comprises a heavy chain variable region and light chain variable region having the amino acid sequences set forth in SEQ ID NO: 48 and 54, respectively. In certain embodiments, the antibody comprises a heavy chain variable region and light chain variable region having the amino acid sequences set forth in SEQ ID NO: 49 and 59, respectively. In certain embodiments, the antibody comprises a heavy chain variable region and light chain variable region having the amino acid sequences set forth in SEQ ID NO: 49 and 60, respectively. In certain embodiments, the antibody comprises a heavy chain variable region and light chain variable region having the amino acid sequences set forth in SEQ ID NO: 50 and 59, respectively. In certain embodiments, the antibody comprises a heavy chain variable region and light chain variable region having the amino acid sequences set forth in SEQ ID NO: 50 and 60, respectively. In certain embodiments, the antibody comprises a heavy chain variable region and light chain variable region having the amino acid sequences set forth in SEQ ID NO: 51 and 61, respectively. In certain embodiments, the antibody comprises a heavy chain variable region and light chain variable region having the amino acid sequences set forth in SEQ ID NO: 52 and 62, respectively. In certain embodiments, the antibody comprises a heavy chain variable region and light chain variable region having the amino acid sequences set forth in SEQ ID NO: 53 and 62, respectively. In certain embodiments, the antibody comprises a heavy chain variable region and light chain variable region having the amino acid sequences set forth in SEQ ID NO: 43 and 63, respectively. In certain embodiments, the antibody comprises a heavy chain variable region and light chain variable region having the amino acid sequences set forth in SEQ ID NO: 44 and 64, respectively. In certain embodiments, the antibody comprises a heavy chain variable region and light chain variable region having the amino acid sequences set forth in SEQ ID NO: 45 and 65, respectively. In certain embodiments, the antibody comprises a heavy chain variable region and light chain variable region having the amino acid sequences set forth in SEQ ID NO: 89 and 91, respectively, optionally wherein the heavy chain variable region does not comprise the amino acid sequence set forth in SEQ ID NO: 15, 16, 17, or 18. In certain embodiments, the antibody comprises a heavy chain variable region and light chain variable region having the amino acid sequences set forth in SEQ ID NO: 90 and 92, respectively, optionally wherein the heavy chain variable region does not comprise the amino acid sequence set forth in SEQ ID NO: 15, 16, 17, or 18.

In certain embodiments, the instant disclosure provides an isolated antibody that specifically binds to ApoC3 (e.g., human ApoC3), the antibody comprising a heavy chain variable region having complementarity determining regions CDRH1, CDRH2 and CDRH3, and a light chain variable region having complementarity determining regions CDRL1, CDRL2 and CDRL3, and wherein:
(a) the CDRH1 comprises the amino acid sequence of TYSMR (SEQ ID NO: 3);
(b) the CDRH2 comprises the amino acid sequence of SIX$_1$TDGGGTAYRDSVKG, wherein X$_1$ is S or H (SEQ ID NO: 4);
(c) the CDRH3 comprises the amino acid sequence of X$_2$GYSD, wherein X$_2$ is A or H (SEQ ID NO: 5);
(d) the CDRL1 comprises the amino acid sequence of KTSQGLVHSDGKTYFY (SEQ ID NO: 6);
(e) the CDRL2 comprises the amino acid sequence of QVSNRAS (SEQ ID NO: 7); and/or
(f) the CDRL3 comprises the amino acid sequence of AX$_3$GTYYPHT, wherein X$_3$ is Q or H (SEQ ID NO: 8).

In certain embodiments, the instant disclosure provides an isolated antibody that specifically binds to ApoC3 (e.g., human ApoC3), the antibody comprising a heavy chain variable region having complementarity determining regions CDRH1, CDRH2 and CDRH3, and a light chain variable region having complementarity determining regions CDRL1, CDRL2 and CDRL3, and wherein:
(a) the CDRH1 comprises the amino acid sequence of TYSMR (SEQ ID NO: 3);
(b) the CDRH2 comprises the amino acid sequence of SIX$_1$TDGGGTAYRDSVKG, wherein X$_1$ is S or H (SEQ ID NO: 4);
(c) the CDRH3 comprises the amino acid sequence of X$_2$GYSD, wherein X$_2$ is A or H (SEQ ID NO: 5);
(d) the CDRL1 comprises the amino acid sequence of KTSQGLVHSDGKTYFY (SEQ ID NO: 6);
(e) the CDRL2 comprises the amino acid sequence of QVSNRAS (SEQ ID NO: 7); and
(f) the CDRL3 comprises the amino acid sequence of AX$_3$GTYYPHT, wherein X$_3$ is Q or H (SEQ ID NO: 8), and wherein at least one of X$_1$, X$_2$, and X$_3$ is H.

In certain embodiments, the instant disclosure provides an isolated antibody that specifically binds to ApoC3 (e.g., human ApoC3), the antibody comprising:
(a) a CDRH1 comprising the amino acid sequence of SEQ ID NO: 3;
(b) a CDRH2 comprising the amino acid sequence of SEQ ID NO: 9 or 11;
(c) a CDRH3 comprising the amino acid sequence of SEQ ID NO: 10 or 12;
(d) a CDRL1 comprising the amino acid sequence of SEQ ID NO: 6;
(e) a CDRL2 comprising the amino acid sequence of SEQ ID NO: 7; and/or
(f) a CDRL3 comprising the amino acid sequence of SEQ ID NO: 13 or 14.

In certain embodiments, the instant disclosure provides an isolated antibody that specifically binds to ApoC3 (e.g., human ApoC3), the antibody comprising:
(a) a CDRH1 comprising the amino acid sequence of SEQ ID NO: 3;
(b) a CDRH2 comprising the amino acid sequence of SEQ ID NO: 9 or 11;
(c) a CDRH3 comprising the amino acid sequence of SEQ ID NO: 10 or 12;
(d) a CDRL1 comprising the amino acid sequence of SEQ ID NO: 6;
(e) a CDRL2 comprising the amino acid sequence of SEQ ID NO: 7; and
(f) a CDRL3 comprising the amino acid sequence of SEQ ID NO: 13 or 14,
and wherein the isolated antibody does not comprise the CDRH1, CDRH2, CDRH3, CDRL1, CDRL2, and CDRL3 sequences set forth in SEQ ID NOs: 3, 9, 10, 6, 7, and 13, respectively.

In certain embodiments, the instant disclosure provides an isolated antibody that specifically binds to ApoC3 (e.g., human ApoC3), wherein the antibody comprises a VH domain comprising the CDRH1, CDRH2 and CDRH3 amino acid sequences set forth in SEQ ID NOs: 3, 9, and 10; 3, 11, and 10; 3, 9, and 12; or 3, 11, and 12, respectively. In certain embodiments, the VH domain comprises the CDRH1, CDRH2 and CDRH3 amino acid sequences set forth in SEQ ID NOs: 3, 11, and 10, respectively. In certain embodiments, the VH domain comprises the CDRH1, CDRH2 and CDRH3 amino acid sequences set forth in SEQ ID NOs: 3, 9, and 12, respectively. In certain embodiments, the VH domain comprises the CDRH1, CDRH2 and CDRH3 amino acid sequences set forth in SEQ ID NOs: 3, 11, and 12, respectively.

In certain embodiments, the instant disclosure provides an isolated antibody that specifically binds to ApoC3 (e.g., human ApoC3), wherein the antibody comprises a VL domain comprising the CDRL1, CDRL2 and CDRL3 amino acid sequences set forth in SEQ ID NOs: 6, 7, and 13; or 6, 7, and 14, respectively. In certain embodiments, the VL domain comprises the CDRL1, CDRL2 and CDRL3 amino acid sequences set forth in SEQ ID NOs: 6, 7, and 14, respectively.

In certain embodiments, the instant disclosure provides an isolated antibody that specifically binds to ApoC3 (e.g., human ApoC3), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 3, 11, 10, 6, 7, and 13; 3, 9, 12, 6, 7, and 13; 3, 9, 10, 6, 7, and 14; 3, 11, 10, 6, 7, and 14; 3, 9, 12, 6, 7, and 14; 3, 11, 12, 6, 7, and 13; or 3, 11, 12, 6, 7, and 13, respectively. In certain embodiments, the CDRH1, CDRH2, CDRH3, CDRL1, CDRL2, and CDRL3 regions comprise the amino acid sequences set forth in SEQ ID NOs: 3, 11, 10, 6, 7, and 14, respectively. In certain embodiments, the CDRH1, CDRH2, CDRH3, CDRL1, CDRL2, and CDRL3 regions comprise the amino acid sequences set forth in SEQ ID NOs: 3, 9, 12, 6, 7, and 14, respectively.

In certain embodiments, the instant disclosure provides an isolated antibody that specifically binds to ApoC3 (e.g., human ApoC3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 15, 16, 17, or 18. In certain embodiments, the antibody comprises a heavy chain variable region having the amino acid sequence set forth in SEQ ID NO: 15, 16, 17, or 18. In certain embodiments, the antibody comprises a heavy chain variable region having the amino acid sequence set forth in SEQ ID NO: 16. In certain embodiments, the antibody comprises a heavy chain variable region having the amino acid sequence set forth in SEQ ID NO: 17. In certain embodiments, the antibody comprises a heavy chain variable region having the amino acid sequence set forth in SEQ ID NO: 18.

In certain embodiments, the instant disclosure provides an isolated antibody that specifically binds to ApoC3 (e.g., human ApoC3), comprising a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 19 or 20. In certain embodiments, the antibody comprises a light chain variable region having the amino acid sequence set forth in SEQ ID NO: 20.

In certain embodiments, the instant disclosure provides an isolated antibody that specifically binds to ApoC3 (e.g., human ApoC3), comprising a heavy chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 15, 16, 17, or 18, and a light chain variable region comprising an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 19 or 20. In certain embodiments, the antibody comprises a heavy chain variable region having the amino acid sequence set forth in SEQ ID NO: 15, 16, 17, or 18, and a light chain variable region having the amino acid sequence set forth in SEQ ID NO: 19 or 20. In certain embodiments, the antibody comprises a heavy chain variable region and light chain variable region having the amino acid sequences set forth in SEQ ID NOs: 16 and 19, 17 and 19, 18 and 19, 15 and 20, 16 and 20, 17 and 20, or 18 and 20, respectively. In certain embodiments, the antibody comprises a heavy chain variable region and light chain variable region having the amino acid sequences set forth in SEQ ID NO: 16 and 20, respectively. In certain embodiments, the antibody comprises a heavy chain variable region and light chain variable region having the amino acid sequences set forth in SEQ ID NO: 17 and 20, respectively.

Any Ig constant region can be used in the isolated antibodies disclosed herein. In certain embodiments, the Ig constant region is a constant region of human IgG, IgE, IgM, IgD, IgA, or IgY immunoglobulin (Ig) molecule, and/or a constant region of any class (e.g., $IgG_1$, $IgG_2$, $IgG_3$, $IgG_4$, $IgA_1$, and $IgA_2$) or any subclass (e.g., $IgG_{2a}$ and $IgG_{2b}$) of immunoglobulin molecule. In certain embodiments, the Ig constant region is a human or humanized Ig constant region.

In certain embodiments, the constant region is a variant of a wild type human Ig (e.g., IgG) heavy chain constant region, and wherein the variant human Ig heavy chain constant region has an increased affinity (e.g., increased by at least 1.5, 2, 2.5, 3, 4, 5, 6, 7, 8, 9, 10, 15, or 20 fold) for human neonatal Fc receptor (FcRn) at acidic pH (e.g., pH 5.5 to pH 6) relative to the affinity of the corresponding wild type human Ig heavy chain constant region for human FcRn under the same conditions. In certain embodiments, the variant human Ig heavy chain constant region has a similar or decreased affinity (e.g., increased by no more than 1.1, 1.2, 1.3, 1.4, 1.5, 1.6, 1.7, 1.8, 1.9, or 2 fold, equal to, or decreased) for human neonatal Fc receptor (FcRn) at physiological pH (e.g., at pH 7.4) relative to the affinity of the wild type human Ig heavy chain constant region for human FcRn under the same conditions. In certain embodiments, the constant region comprises one, two, or more amino acids (e.g., having one or more substitutions, insertions or deletions) from a wild-type Ig (e.g., IgG) constant domain or FcRn-binding fragment thereof (e.g., an Fc or hinge-Fc domain fragment). In certain embodiments, the half-life of the antibody with the variant constant region in vivo is increased relative to the half-life of the corresponding antibody with the wild-type constant domain or FcRn-binding fragment thereof in vivo. See, e.g., International Publication Nos. WO 02/060919; WO 98/23289; and WO 97/34631; and U.S. Pat. Nos. 5,869,046, 6,121,022, 6,277,375, 6,165,745, 8,088,376, and 8,163,881, all of which are herein incorporated by reference in their entireties, for examples of mutations that will increase the half-life of an antibody in vivo. In certain embodiment, the one or more different amino acid are in the second constant (CH2) domain (residues 231-340 of human $IgG_1$) and/or the third constant (CH3) domain (residues 341-447 of human $IgG_1$), numbered according to the EU numbering system. In certain embodiments, the constant region of the IgG (e.g., $IgG_1$, $IgG_2$, or $IgG_4$) of an antibody disclosed herein comprises the amino acids tyrosine (Y) threonine (T), and glutamic acid (E) at positions 252, 254, and 256, respectively, numbered according to the EU numbering system. See U.S. Pat. No. 7,658,921, which is herein incorporated by reference in its entirety. This type of IgG, referred to as "YTE IgG" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, the constant region of the IgG (e.g., $IgG_1$) of an antibody disclosed herein comprises the amino acid alanine (A), serine (S), tyrosine (Y), or phenylalanine (F) at position 434, numbered according to the EU numbering system. In certain embodiments, the constant region of the IgG (e.g., $IgG_1$, $IgG_2$, or $IgG_4$) of an antibody disclosed herein comprises the amino acids lysine (K), phenylalanine (F), and tyrosine (Y) at positions 433, 434, and 436, respectively, numbered according to the EU numbering system. In certain embodiments, the constant region of the IgG (e.g., $IgG_1$, $IgG_2$, or $IgG_4$) of an antibody disclosed herein comprises the amino acids leucine (L) and serine (S) at positions 428 and 434, respectively, numbered according to the EU numbering system. Additional IgG constant regions that may have increased affinity to FcRn under acidic condition are described in Ward et al., Mol. Immunol. (2015) 67(200): 131-41, which is herein incorporated by reference in its entirety. In certain embodiments, an antibody comprises an IgG constant domain comprising one, two, three or more amino acid substitutions of amino acid residues at positions 251-257, 285-290, 308-314, 385-389, and 428-436, numbered according to the EU numbering system. In certain embodiments, the isolated antibodies disclosed herein comprise a heavy chain constant region comprising the amino acid sequence set forth in SEQ ID NO: 21, 22, 23, 24, 75, 76, 77, 78, 79, 80, 81, 82, 83, 84, 85, or 86. In certain embodiments, the isolated antibodies disclosed herein comprise a light chain constant region comprising the amino acid sequence set forth in SEQ ID NO: 25 or 26.

In certain embodiments, the instant disclosure provides an isolated antibody that specifically binds to ApoC3 (e.g., human ApoC3), comprising a heavy chain comprising the amino acid sequence set forth in SEQ ID NO: 66, 67, 68, 69, 70, 71, 72, or 73. In certain embodiments, the instant disclosure provides an isolated antibody that specifically binds to ApoC3 (e.g., human ApoC3), comprising a light chain comprising the amino acid sequence set forth in SEQ ID NO: 74. In certain embodiments, the instant disclosure provides an isolated antibody that specifically binds to ApoC3 (e.g., human ApoC3), comprising a heavy chain and a light chain comprising the amino acid sequences set forth in SEQ ID NOs: 66 and 74, 67 and 74, 68 and 74, 69 and 74, 70 and 74, 71 and 74, 72 and 74, or 73 and 74, respectively.

In certain embodiments, the instant disclosure provides an isolated antibody that specifically binds to ApoC3 (e.g., human ApoC3), comprising a heavy chain comprising the amino acid sequence set forth in SEQ ID NO: 27, 28, 29, 30, 31, 32, 33, or 34. In certain embodiments, the instant disclosure provides an isolated antibody that specifically binds to ApoC3 (e.g., human ApoC3), comprising a light chain comprising the amino acid sequence set forth in SEQ ID NO: 35. In certain embodiments, the instant disclosure provides an isolated antibody that specifically binds to ApoC3 (e.g., human ApoC3), comprising a heavy chain and a light chain comprising the amino acid sequences set forth in SEQ ID NOs: 27 and 35, 28 and 35, 29 and 35, 30 and 35, 31 and 35, 32 and 35, 33 and 35, or 34 and 35, respectively.

3. Methods of Use

ApoC3 inhibits TRL (e.g., VLDL) and TRL remnant uptake and clearance by hepatocytes and inhibits lipoprotein lipase-mediated lipolysis of TRL (e.g., VLDL), thereby functioning to increase triglyceride levels in the blood of a subject. In certain embodiments, the anti-ApoC3 antibodies disclosed herein can attenuate the ability of ApoC3 to inhibit TRL (e.g., VLDL) and TRL remnant uptake and clearance by hepatocytes or attenuate the ability of ApoC3 to inhibit lipoprotein lipase-mediated lipolysis of TRL (e.g., VLDL). Accordingly, in certain embodiments, the instant disclosure provides a method for inhibiting the activity of ApoC3 in the blood of a subject, the method comprising administering to the subject an effective amount of an anti-ApoC3 antibody or pharmaceutical composition disclosed herein. In certain embodiments, the activity of ApoC3 is inhibition of TRL (e.g., VLDL) and TRL remnants uptake and clearance by hepatocytes. In certain embodiments, the activity of ApoC3 is inhibition of lipoprotein lipase-mediated lipolysis of TRL. In certain embodiments, the activity of ApoC3 is inhibition of TRL (e.g., VLDL) and TRL remnants uptake and clearance by hepatocytes and inhibition of lipoprotein lipase-mediated lipolysis of TRL.

The anti-ApoC3 antibodies disclosed herein are useful for increasing the rate of clearance of ApoC3 and/or ApoB (e.g., ApoB48 and/or ApoB100) from the blood in a subject. Accordingly, in certain embodiments, the instant disclosure provides a method for increasing the rate of clearance of ApoC3 and/or ApoB (e.g., ApoB48 and/or ApoB100) from the blood in a subject, the method comprising administering to the subject an effective amount of an anti-ApoC3 antibody or pharmaceutical composition disclosed herein.

The anti-ApoC3 antibodies disclosed herein are useful for reducing the level of ApoC3 and/or ApoB (e.g., ApoB48 and/or ApoB100) in the blood of a subject. Accordingly, in certain embodiments, the instant disclosure provides a method for reducing the level of ApoC3 and/or ApoB (e.g., ApoB48 and/or ApoB100) in the blood of a subject, the method comprising administering to the subject an effective amount of an anti-ApoC3 antibody or pharmaceutical composition disclosed herein. In certain embodiments, the method reduces the level of ApoC3 and/or ApoB (e.g., ApoB48 and/or ApoB100) in the blood of a subject by at least 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods disclosed herein or by methods known to one of skill in the art. In certain embodiments, the method reduces the levels of ApoC3 and/or ApoB (e.g., ApoB48 and/or ApoB100) in the blood in a subject by at least about 1.1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods disclosed herein or by methods known to one of skill in the art. In certain embodiments, the reduction in the levels of ApoC3 and/or ApoB (e.g., ApoB48 and/or ApoB100) in the blood in the subject is maintained for at least 1, 2, 3, 4, 5, 6, 7, 8, 9, 10, 15, 20, 25, 30, 35, 40, 45, or 50 days, or at least 1, 2, 3, 4, 5, 6, 7, or 8 weeks.

The anti-ApoC3 antibodies disclosed herein are useful for reducing triglyceride levels in the blood of a subject. Accordingly, in certain embodiments, the instant disclosure provides a method for reducing triglyceride levels in the blood of a subject, the method comprising administering to the subject an effective amount of an anti-ApoC3 antibody or pharmaceutical composition disclosed herein.

The anti-ApoC3 antibodies disclosed herein are useful for the treatment of hypertriglyceridemia. Accordingly, in certain embodiments, the instant disclosure provides a method for treating hypertriglyceridemia in a subject, the method comprising administering to the subject an effective amount of an anti-ApoC3 antibody or pharmaceutical composition disclosed herein. In certain embodiments, the instant disclosure provides a method for treating chylomicronemia in a subject, the method comprising administering to the subject an effective amount of an anti-ApoC3 antibody or pharmaceutical composition disclosed herein. In certain embodiments, the instant disclosure provides a method for treating chylomicronemia syndrome in a subject, the method comprising administering to the subject an effective amount of an anti-ApoC3 antibody or pharmaceutical composition disclosed herein.

The anti-ApoC3 antibodies disclosed herein are useful for the treatment and prevention of post-prandial lipemia in a subject. Accordingly, in certain embodiments, the instant disclosure provides a method for inhibiting post-prandial lipemia in a subject, the method comprising administering to the subject an effective amount of an anti-ApoC3 antibody or pharmaceutical composition disclosed herein. The anti-ApoC3 antibody can be administered to the subject prior to, during, or after a meal.

Without wishing to be bound by theory, Applicants believe that, in certain embodiments, the antibodies disclosed herein are capable of reducing the levels of post-prandial chylomicron or chylomicron remnants in a subject when administered to the subject prior to, during, or after a meal. Accordingly, in certain embodiments, the instant disclosure provides a method for reducing the levels of post-prandial chylomicron or chylomicron remnants in a subject, the method comprising administering to the subject an effective amount of an anti-ApoC3 antibody or pharmaceutical composition disclosed herein. The anti-ApoC3 antibody can be administered to the subject prior to, during, or after a meal.

The reduction of triglyceride levels in blood in patients with hypertriglyceridemia may reduce the risk of development of pancreatitis. Accordingly, in certain embodiments, the instant disclosure provides a method for reducing the risk of pancreatitis in a subject with hypertriglyceridemia, the method comprising administering to the subject an effective amount of an anti-ApoC3 antibody or pharmaceutical composition disclosed herein The anti-ApoC3 antibodies disclosed herein are useful for reducing the risk of cardiovascular disease in a subject. Accordingly, in certain embodiments, the instant disclosure provides a method for reducing the risk of cardiovascular disease in a subject with hypertriglyceridemia, the method comprising administering to the subject an effective amount of an anti-ApoC3 antibody or pharmaceutical composition disclosed herein. The risk of developing any cardiovascular disease associated with or caused by hypertriglyceridemia or excessive post prandial lipemia can be reduced by administration of an anti-ApoC3 antibody or pharmaceutical composition disclosed herein. Cardiovascular disease for which the risk can be reduced include without limitation coronary artery disease, atherosclerosis, angina, myocardial infarction, and stroke.

The anti-ApoC3 antibodies or pharmaceutical compositions disclosed herein can be administered either alone or in combination an additional therapeutic agent. In certain embodiments, the additional therapeutic agent is another lipid lowering agent. Any one or more lipid lowering agent can be used in combination with an anti-ApoC3 antibody or pharmaceutical composition disclosed herein. Suitable lipid lowering agents include without limitation HMG-CoA reductase inhibitors (e.g., atorvastatin, fluvastatin, lovastatin, pitavastatin, pravastatin, rosuvastatin or simvastatin), fibrates, niacin, bile acid sequestrants (e.g., cholestyramine, colestipol, and colesevelam), inhibitors of dietary cholesterol absorption (e.g., ezetimibe), microsomal triglyceride transfer protein (MTP) inhibitors (e.g., lomitapide), phytosterols, pancreatic lipase inhibitors (e.g., orlistat), cholesteryl ester transfer protein inhibitors, squalene synthase inhibitors (e.g., TAK-475, zaragozic acid, and RPR 107393), ApoA-1 Milano, succinobucol (AGI-1067), Apoprotein-B inhibitors (e.g., Mipomersen), and proprotein convertase subtilisin/kexin type 9 (PCSK9) inhibitors (e.g., alirocumab, evolocumab, and bococizumab). In certain embodiments, the additional lipid lowering agent is a combination of ezetimibe and an HMG-CoA reductase inhibitor. In certain embodiments, the lipid lowering agent is a combination of ezetimibe, an HMG-CoA reductase inhibitor, and a PCSK9 inhibitor.

The anti-ApoC3 antibodies or pharmaceutical compositions disclosed herein may be delivered to a subject by a variety of routes. These include, but are not limited to, parenteral, intradermal, intramuscular, intraperitoneal, intravenous, and subcutaneous routes. In certain embodiments, the antibody or pharmaceutical composition disclosed herein is delivered subcutaneously or intravenously.

The amount of an anti-ApoC3 antibody or pharmaceutical composition disclosed herein which will be effective in the treatment or prevention of a condition will depend on the nature of the disease, and can be empirically determined by standard clinical techniques. The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. The anti-ApoC3 antibodies or pharmaceutical compositions disclosed herein can be administered at any frequency (e.g., about every week, every two weeks, every three weeks, every four weeks, every month, or every two months). Usually, the patient is a human, but non-human mammals including transgenic mammals can also be treated. Treatment dosages and regimens are optimally titrated to optimize safety and efficacy.

The anti-ApoC3 antibodies disclosed herein can also be used to assay ApoC3 (e.g., human ApoC3) protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I)carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody disclosed herein. Alternatively, a second antibody that recognizes an anti-ApoC3 antibody disclosed herein can be labeled and used in combination with an anti-ApoC3 antibody to detect ApoC3 (e.g., human ApoC3) protein levels.

Assaying for the expression level of ApoC3 (e.g., human ApoC3) protein is intended to include qualitatively or quantitatively measuring or estimating the level of ApoC3 (e.g., human ApoC3) protein in a first biological sample either directly (e.g., by determining or estimating absolute protein level) or relatively (e.g., by comparing to the disease associated protein level in a second biological sample). ApoC3 (e.g., human ApoC3) polypeptide expression level in the first biological sample can be measured or estimated and compared to a standard ApoC3 (e.g., human ApoC3) protein level, the standard being taken from a second biological sample obtained from an individual not having the disorder or being determined by averaging levels from a population of individuals not having the disorder. As will be appreciated in the art, once the "standard" ApoC3 (e.g., human ApoC3) polypeptide level is known, it can be used repeatedly as a standard for comparison.

As used herein, the term "biological sample" refers to any biological sample obtained from a subject, cell line, tissue, or other source of cells potentially expressing ApoC3 (e.g., human ApoC3). Methods for obtaining tissue biopsies and body fluids from animals (e.g., humans) are well known in the art. Biological samples include peripheral mononuclear blood cells.

The anti-ApoC3 antibodies disclosed herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status or immune response may be utilized to predict, diagnose and monitor to evaluate patient samples including those known to have or suspected of having elevated ApoC3 activity. In one embodiment, an anti-ApoC3 antibody can be used in immunohistochemistry of biopsy samples. In another embodiment, an anti-ApoC3 antibody can be used to detect levels of ApoC3 (e.g., human ApoC3), which levels can then be linked to certain disease symptoms. Anti-ApoC3 antibodies disclosed herein may carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-ApoC3 antibodies disclosed herein may carry a fluorescence label. Exemplary fluorescence labels include, for example, reactive and conjugated probes e.g. Aminocoumarin, Fluorescein and Texas red, Alexa Fluor dyes, Cy dyes and DyLight dyes. An anti-ApoC3 antibody may carry a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$ an $^{186}Re$. When radioactive labels are used, currently available counting procedures known in the art may be utilized to identify and quantitate the specific binding of anti-ApoC3 antibody to ApoC3 (e.g., human ApoC3). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-ApoC3 antibody under conditions that allow for the formation of a complex between the antibody and ApoC3 (e.g., human ApoC3). Any complexes formed between the antibody and ApoC3 (e.g., human ApoC3) are detected and compared in the sample and the control. The antibodies disclosed herein can also be used to purify ApoC3 (e.g., human ApoC3) via immunoaffinity purification. Also included herein is an assay system which may be prepared in the form of a test kit for the quantitative analysis of the extent of the presence of, for instance, ApoC3 (e.g., human ApoC3). The system or test kit may comprise a labeled component, e.g., a labeled ApoC3 antibody, and one or more additional immunochemical reagents.

4. Pharmaceutical Compositions

Provided herein are pharmaceutical compositions comprising an anti-ApoC3 antibody disclosed herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); or non-ionic surfactants such as TWEEN™, PLURONICS™ or polyethylene glycol (PEG).

In a specific embodiment, pharmaceutical compositions comprise an anti-ApoC3 antibody disclosed herein, and optionally one or more additional prophylactic or therapeutic agents, in a pharmaceutically acceptable carrier. In a specific embodiment, pharmaceutical compositions comprise an effective amount of an antibody disclosed herein, and optionally one or more additional prophylactic or therapeutic agents, in a pharmaceutically acceptable carrier. In some embodiments, the antibody is the only active ingredient included in the pharmaceutical composition. Pharmaceutical compositions disclosed herein can be useful in inhibiting, ApoC3 activity and treating a condition, such as cancer or an infectious disease.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-ApoC3 antibody disclosed herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

An anti-ApoC3 antibody disclosed herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

In certain embodiments, a pharmaceutical composition comprising an disclosed herein is a lyophilized powder, which can be reconstituted for administration as solutions, emulsions and other mixtures. It may also be reconstituted and formulated as solids or gels. The lyophilized powder is prepared by dissolving an antibody disclosed herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-ApoC3 antibodies disclosed herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

The compositions to be used for in vivo administration can be sterile. This is readily accomplished by filtration through, e.g., sterile filtration membranes.

5. Polynucleotides, Vectors and Methods of Producing Anti-ApoC3 Antibodies

In another aspect, provided herein are polynucleotides comprising a nucleotide sequence encoding an anti-ApoC3 antibody disclosed herein (e.g., a light chain variable region or heavy chain variable region), and vectors, e.g., vectors comprising such polynucleotides for recombinant expression in host cells (e.g., *E. coli* and mammalian cells).

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors or other chemicals. In a specific embodiment, a nucleic acid molecule(s) encoding an antibody disclosed herein is isolated or purified.

In particular aspects, provided herein are polynucleotides comprising nucleotide sequences encoding antibodies, which specifically bind to ApoC3 (e.g., human ApoC3) polypeptide and comprises an amino acid sequence as disclosed herein, as well as antibodies which compete with such antibodies for binding to ApoC3 (e.g., human ApoC3) polypeptide (e.g., in a dose-dependent manner), or which binds to the same epitope as that of such antibodies.

In certain aspects, provided herein are polynucleotides comprising a nucleotide sequence encoding the light chain or heavy chain of an antibody disclosed herein. The polynucleotides can comprise nucleotide sequences encoding the VH, VL or CDRs of antibodies disclosed herein (see, e.g., Tables 1-4 herein).

Also provided herein are polynucleotides encoding an anti-ApoC3 antibody that are optimized, e.g., by codon/RNA optimization, replacement with heterologous signal sequences, and elimination of mRNA instability elements. Methods to generate optimized nucleic acids encoding an anti-ApoC3 antibody (e.g., light chain, heavy chain, VH domain, or VL domain) for recombinant expression by introducing codon changes or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties or function as the original amino acid. Such methods can increase expression of an anti-ApoC3 by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-ApoC3 antibody encoded by polynucleotides that have not been optimized.

In certain embodiments, an optimized polynucleotide sequence encoding an anti-ApoC3 antibody disclosed herein (e.g., VL domain or VH domain) can hybridize to an antisense (e.g., complementary) polynucleotide of an unoptimized polynucleotide sequence encoding an anti-ApoC3 antibody disclosed herein (e.g., VL domain or VH domain). In specific embodiments, an optimized nucleotide sequence encoding an anti-ApoC3 antibody disclosed herein or a fragment hybridizes under high stringency conditions to antisense polynucleotide of an unoptimized polynucleotide sequence encoding an anti-ApoC3 antibody disclosed herein. In a specific embodiment, an optimized nucleotide sequence encoding an anti-ApoC3 antibody disclosed herein hybridizes under high stringency, intermediate or lower stringency hybridization conditions to an antisense polynucleotide of an unoptimized nucleotide sequence encoding an anti-ApoC3 antibody disclosed herein. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies disclosed herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody disclosed herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain or heavy chain of an antibody. Such PCR amplification methods can be used to obtain nucleic acids comprising the sequence encoding the variable light chain region or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody disclosed herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-ApoC3 (e.g., human ApoC3) antibodies disclosed herein can be readily isolated and sequenced using conventional procedures (e.g., by using oligonucleotide probes that are capable of binding specifically to genes encoding the heavy and light chains of the anti-ApoC3 (e.g., human ApoC3) antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-ApoC3 (e.g., human ApoC3) antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody disclosed herein. In specific embodiments, polynucleotides disclosed herein hybridize under high stringency, intermediate or lower stringency hybridization conditions to polynucleotides encoding a VH domain or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

In certain aspects, provided herein are cells (e.g., host cells) expressing (e.g., recombinantly) antibodies disclosed herein which specifically bind to ApoC3 (e.g., human ApoC3) and related polynucleotides and expression vectors. Provided herein are vectors (e.g., expression vectors) comprising polynucleotides comprising nucleotide sequences encoding anti-ApoC3 (e.g., human ApoC3) antibodies or a fragment for recombinant expression in host cells, preferably in mammalian cells. Also provided herein are host cells comprising such vectors for recombinantly expressing anti-ApoC3 (e.g., human ApoC3) antibodies disclosed herein (e.g., human or humanized antibody). In a particular aspect, provided herein are methods for producing an antibody disclosed herein, comprising expressing such antibody from a host cell.

Recombinant expression of an antibody disclosed herein (e.g., a full-length antibody, heavy or light chain of an antibody, or a single chain antibody disclosed herein) that specifically binds to ApoC3 (e.g., human ApoC3) involves construction of an expression vector containing a polynucleotide that encodes the antibody. Once a polynucleotide encoding an antibody molecule, heavy or light chain of an antibody, (e.g., heavy or light chain variable regions) disclosed herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are disclosed herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule disclosed herein, a heavy or light chain of an antibody, a heavy or light chain variable region of an antibody, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody disclosed herein. Thus, provided herein are host cells containing a polynucleotide encoding an antibody disclosed herein, or a heavy or light chain thereof, or fragment thereof, or a single chain antibody disclosed herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody disclosed herein. In specific embodiments, a host cell contains two different vectors, a first vector comprising a polynucleotide encoding a heavy chain or a heavy chain variable region of an antibody disclosed herein, or a fragment thereof, and a second vector comprising a polynucleotide encoding a light chain or a light chain variable region of an antibody disclosed herein, or a fragment thereof. In other embodiments, a first host cell comprises a first vector comprising a polynucleotide encoding a heavy chain or a heavy chain variable region of an antibody disclosed herein, or a fragment thereof, and a second host cell comprises a second vector comprising a polynucleotide encoding a light chain or a light chain variable region of an antibody disclosed herein. In specific embodiments, a heavy chain/heavy chain variable region expressed by a first cell associated with a light chain/light chain variable region of a second cell to form an anti-ApoC3 antibody disclosed herein. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-ApoC3 antibody disclosed herein, and a second vector comprising a polynucleotide encoding a heavy chain/heavy chain variable region of an anti-ApoC3 antibody disclosed herein.

A variety of host-expression vector systems can be utilized to express antibody molecules disclosed herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule disclosed herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid)

containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies disclosed herein are CHO cells, for example CHO cells from the CHO GS System™ (Lonza). In a particular embodiment, cells for expressing antibodies disclosed herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7). In certain embodiments, antibodies disclosed herein are produced by CHO cells or NS0 cells. In a specific embodiment, the expression of nucleotide sequences encoding antibodies disclosed herein which specifically bind ApoC3 (e.g., human ApoC3) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region El or E3) will result in a recombinant virus that is viable and capable of expressing the antibody molecule in infected hosts (e.g., see Logan J & Shenk T (1984) PNAS 81(12): 3655-9). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-ApoC3 (e.g., human ApoC3) antibodies disclosed herein are produced in mammalian cells, such as CHO cells.

In a specific embodiment, the antibodies disclosed herein have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of α1,6-fucosyltransferase can be used to produce antibodies with reduced fucose content. The Potelligent® system (Lonza) is an example of such a system that can be used to produce antibodies with reduced fucose content.

For long-term, high-yield production of recombinant proteins, stable expression cells can be generated. For example, cell lines which stably express an anti-ApoC3 antibody disclosed herein can be engineered. In specific embodiments, a cell provided herein stably expresses a light chain/light chain variable region and a heavy chain/heavy chain variable region which associate to form an antibody disclosed herein.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-ApoC3 antibody disclosed herein. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034) and adenine phosphoribosyltransferase (Lowy I et al., (1980) Cell 22(3): 817-23) genes in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56). Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Kohler G (1980) PNAS 77: 2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody disclosed herein), and a second gene and (e.g., light chain of an antibody disclosed herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule disclosed herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies disclosed herein can be fused to heterologous polypeptide sequences disclosed herein or otherwise known in the art to facilitate purification.

In specific embodiments, an antibody disclosed herein is isolated or purified. Generally, an isolated antibody is one that is substantially free of other antibodies with different antigenic specificities than the isolated antibody. For example, in a particular embodiment, a preparation of an antibody disclosed herein is substantially free of cellular material or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies disclosed herein are isolated or purified.

Antibodies that specifically bind to ApoC3 (e.g., human ApoC3) can be produced by any method known in the art for the synthesis of antibodies, for example, by chemical synthesis or by recombinant expression techniques. The methods disclosed herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In a specific embodiment, an antibody disclosed herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In one aspect, provided herein is a method of making an antibody which specifically binds to ApoC3 (e.g., human ApoC3) comprising culturing a cell or host cell disclosed herein. In a certain aspect, provided herein is a method of making an antibody which specifically binds to ApoC3 (e.g., human ApoC3) comprising expressing (e.g., recombinantly expressing) the antibody using a cell or host cell disclosed herein (e.g., a cell or a host cell comprising polynucleotides encoding an antibody disclosed herein). In a particular embodiment, the cell is an isolated cell. In a particular embodiment, the exogenous polynucleotides have been introduced into the cell. In a particular embodiment, the method further comprises the step of purifying the antibody obtained from the cell or host cell.

Methods for producing polyclonal antibodies are known in the art (see, for example, Chapter 11 in: Short Protocols in Molecular Biology, (2002) 5th Ed., Ausubel F M et al., eds., John Wiley and Sons, New York).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981). The term "monoclonal antibody" as used herein is not limited to antibodies produced through hybridoma technology. For example, monoclonal antibodies can be produced recombinantly from host cells exogenously expressing an antibody disclosed herein, for example, light chain or heavy chain of such antibody.

In specific embodiments, a "monoclonal antibody," as used herein, is an antibody produced by a single cell (e.g., hybridoma or host cell producing a recombinant antibody), wherein the antibody specifically binds to ApoC3 (e.g., human ApoC3) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies disclosed herein can, for example, be made by the hybridoma method as described in Kohler G & Milstein C (1975) Nature 256: 495 or can, e.g., be isolated from phage libraries using the techniques as disclosed herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., ApoC3 (e.g., human ApoC3)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986)). Additionally, a RIMMS (repetitive immunization multiple sites) technique can be used to immunize an animal (Kilpatrick K E et al., (1997) Hybridoma 16:381-9, incorporated by reference in its entirety).

In some embodiments, mice (or other animals, such as rats, monkeys, donkeys, pigs, sheep, hamster, or dogs) can be immunized with an antigen (e.g., ApoC3 (e.g., human ApoC3)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against ApoC3 (e.g., human ApoC3). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies disclosed herein include antibody fragments which recognize specific ApoC3 (e.g., human ApoC3) and can be generated by any technique known to those of skill in the art. For example, Fab and F(ab')$_2$ fragments disclosed herein can be produced by proteolytic cleavage of immunoglobulin molecules, using enzymes such as papain (to produce Fab fragments) or pepsin (to produce F(ab')$_2$ fragments). A Fab fragment corresponds to one of the two identical arms of an antibody molecule and contains the complete light chain paired with the VH and CH1 domains of the heavy chain. A F(ab')$_2$ fragment contains the two antigen-binding arms of an antibody molecule linked by disulfide bonds in the hinge region.

Further, the antibodies disclosed herein can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies disclosed herein include those disclosed in Brinkman U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_2$, IgG$_3$ and IgG$_4$. Humanized antibodies can be produced using a variety of techniques known in the art, including but not limited to, CDR-grafting (European Patent No. EP 239400; International Publication No. WO 91/09967; and U.S. Pat. Nos.

5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301.

Further, antibodies that specifically bind to ApoC3 (e.g., human ApoC3) can, in turn, be utilized to generate antiidiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438).

In particular embodiments, an antibody disclosed herein, which binds to the same epitope of ApoC3 (e.g., human ApoC3) as an anti-ApoC3 antibody disclosed herein, is a human antibody. In particular embodiments, an antibody disclosed herein, which competitively blocks (e.g., in a dose-dependent manner) any one of the antibodies disclosed herein, from binding to ApoC3 (e.g., human ApoC3), is a human antibody. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., ApoC3 (e.g., human ApoC3)). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin).

Human antibodies which specifically bind to ApoC3 (e.g., human ApoC3) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., ApoC3 (e.g., human ApoC3)). Such methods are known and are described in the art, see, e.g., Shinmoto H et al., (2004) Cytotechnology 46: 19-23; Naganawa Y et al., (2005) Human Antibodies 14: 27-31.

6. Kits

Also provided, are kits comprising one or more antibodies disclosed herein, or pharmaceutical composition or conjugates thereof. In a specific embodiment, provided herein is a pharmaceutical pack or kit comprising one or more containers filled with one or more of the ingredients of the pharmaceutical compositions disclosed herein, such as one or more antibodies provided herein. In some embodiments, the kits contain a pharmaceutical composition disclosed herein and any prophylactic or therapeutic agent, such as those disclosed herein. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody disclosed herein, preferably a purified antibody, in one or more containers. In a specific embodiment, kits disclosed herein contain a substantially isolated ApoC3 (e.g., human ApoC3) antigen as a control. In another specific embodiment, the kits disclosed herein further comprise a control antibody which does not react with an ApoC3 (e.g., human ApoC3) antigen. In another specific embodiment, kits disclosed herein contain one or more elements for detecting the binding of an antibody to ApoC3 (e.g., human ApoC3) antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized ApoC3 (e.g., human ApoC3) antigen. The ApoC3 (e.g., human ApoC3) antigen provided in the kit can also be attached to a solid support. In a more specific embodiment, the detecting means of the above described kit includes a solid support to which an ApoC3 (e.g., human ApoC3) antigen is attached. Such a kit can also include a non-attached reporter-labeled anti-human antibody or anti-mouse/rat antibody. In this embodiment, binding of the antibody to the ApoC3 (e.g., human ApoC3) antigen can be detected by binding of the said reporter-labeled antibody.

EXAMPLES

The previously identified antibody clone, 5E5, binds to ApoC3 with high affinity at pH 7.4 and slightly reduced affinity at pH 5.5 (see U.S. provisional application 62/360,084). The instant disclosure provides novel derivatives of clone 5E5 that exhibit high affinity binding to ApoC3 at pH 7.4, but much reduced affinity to ApoC3 at pH 5.5 relative to 5E5. The following examples describe the characterization of the novel 5E5 derivatives. The amino acid sequences of 5E5 are set forth in U.S. provisional application 62/360,084, and the amino sequences of the novel 5E5 derivatives are set forth in Tables 1-7, herein.

The examples in this Section are provided to further elucidate the advantages and features of the present application, but are not intended to limit the scope of the application. The examples are for illustrative purposes only.

Example 1: In Vitro Characterization of Anti-ApoC3 scFv-Fc Antibodies

This example describes surface plasmon resonance (SPR)-based experiments to determine the antigen-binding kinetics, at both pH 7.4 and pH 5.5, of anti-ApoC3 scFv-Fc antibodies.

A panel of novel derivatives of antibody clone 5E5 was generated by substitution of one or more CDR amino acids in the VH and/or VL of 5E5 with histidine. The antigen-binding kinetics, at both pH 7.4 and pH 5.5, of each 5E5 derivative was assessed using the SPR-based method set forth below, and clones exhibiting high affinity binding to ApoC3 at pH 7.4, but much reduced affinity to ApoC3 at pH 5.5 relative to 5E5 were selected for further characterization. The binding kinetics of exemplary 5E5 derivatives 5E5VH5_VLWT, 5E5VH12_VLWT, and 5E5VHWT_VL8 are set forth in Table 14.

Test antibodies were produced from transfected HEK293 cells at 50 ml small-scale cultures and purified by protein A chromatography using the ÄKTA pure chromatography system. The quality and yields of the purified of the antibody fragments were determined by spectrophotometry and by SDS-PAGE.

An SPR-based method was employed, in which biotinylated human ApoC3 was captured on a streptavidin (SA) coated chip, and the binding kinetics of test antibodies to the coated chip were measured at both pH 7.4 and pH 5.5. Briefly, 20 µl of biotinylated human ApoC3 was injected at a concentration of 10 µg/ml to reach a surface density of approximately 500 RU. 60 µl of each test antibody was diluted in HBS-EP buffer (GE, cat. nr. BR-1008-26; 0.010 M HEPES, 0.150M NaCl, 3 mM EDTA, 0.05% (v/v) surfactant P20, pH 7.4), and was injected at a concentration of 1-100 nM. The test antibodies were passed through the flow cells at a flow rate of 30 µl/min, followed by an off-rate wash at pH 7.4 or pH 5.5 for 5 min. The resulting sensorgrams were analyzed using the BIAevaluation 4.1 software applying the Langmuir 1:1 binding model to derive binding kinetics. Data was zero adjusted and the reference cell sensorgrams were subtracted.

TABLE 14

| Binding kinetics of anti-ApoC3 scFv-Fc antibodies at pH 7.4 and pH 5.5 | | | | | | |
|---|---|---|---|---|---|---|
| | Association Rate | | Dissociation Rate | | Affinity | |
| Antibody | ka (1/Ms) pH 7.4 | ka (1/Ms) pH 5.5 | kd (1/s) pH 7.4 | kd (1/s) pH 5.5 | $K_D$ (nM) pH 7.4 | $K_D$ (nM) pH 5.5 | $K_D$ pH 5.5/ $K_D$ pH 7.4 |
| 5E5WT | 8.23E+05 | 3.93E+05 | 1.75E−05 | 2.53E−05 | 0.02 | 0.06 | 3.0 |
| 5E5VH5_VLWT | 1.78E+05 | 1.47E+05 | 1.05E−04 | 1.60E−03 | 0.59 | 10.90 | 18.5 |
| 5E5VH12_VLWT | 3.08E+05 | 1.29E+05 | 1.57E−04 | 2.06E−03 | 0.51 | 16.00 | 31.4 |
| 5E5VHWT_VL8 | 3.81E+05 | 2.69E+05 | 2.21E−04 | 1.16E−03 | 0.58 | 4.29 | 7.4 |

All scFv-Fc antibodies tested exhibited higher affinity for ApoC3 at pH 7.4 than at pH 5.5, with antibody 5E5VH12_VLWT showing the most pronounced pH-dependent binding (see Table 14). The magnitude of pH-dependent binding positively correlated with the dissociation rate under acidic conditions.

Example 2: In Vitro Characterization of Anti-ApoC3 Human IgG$_1$ Antibodies

Based on the results in Example 1, test scFv-Fc antibodies were generated as human IgG$_1$ antibodies. An SPR-based assay was employed, in which human ApoC3 protein was immobilized on a CM5 chip, and the binding kinetics of test antibodies to the coated chip were measured at both pH 7.4 and pH 5.5. Briefly, a solution of 50 µg/ml of native human ApoC3 in 10 mM acetate buffer at pH 4.5 was prepared and injected until the surface density reached approximately 500 RU. 60 µl of each test antibody was diluted in HBS-EP buffer (GE, cat. nr. BR-1008-26; 0.010 M HEPES, 0.150M NaCl, 3 mM EDTA, 0.05% (v/v) surfactant P20, pH 7.4), and was injected at a concentration as described in Table 9. The test antibodies were passed through the flow cells at a flow rate of 30 µl/min, followed by an off-rate wash at pH 7.4 or pH 5.5 for 5 min. The resulting sensorgrams were analyzed using the BIAevaluation 4.1 software applying the Langmuir 1:1 binding model to derive binding kinetics. Data was zero adjusted and the reference cell sensorgrams were subtracted.

TABLE 15

Binding kinetics of anti ApoC3 human IgG$_1$ antibodies at pH 7.4 and pH 5.5

| Antibody | pH | ka (1/Ms) | kd (1/s) | Rmax (RU) | Concentration | K$_D$ (M) |
|---|---|---|---|---|---|---|
| 5E5WT | 7.4 | 3.50E+05 | 1.79E−05 | 475 | 50-0.8 nM | 5.12E−11 |
|  | 5.5 | 3.40E+05 | 1.70E−05 | 519 | 50-0.8 nM | 4.99E−11 |
| 5E5VH5_VLWT | 7.4 | 1.78E+05 | 3.77E−05 | 347 | 50-0.8 nM | 2.11E−10 |
|  | 5.5 | 1.55E+05 | 2.03E−04 | 313 | 50-0.8 nM | 1.31E−09 |
| 5E5VH12_VLWT | 7.4 | 3.93E+05 | 1.38E−05 | 420 | 50-0.8 nM | 3.51E−11 |
|  | 5.5 | 3.66E+05 | 3.74E−05 | 413 | 50-0.8 nM | 1.02E−09 |
| 5E5VHWT_VL8 | 7.4 | 7.82E+05 | 2.84E−05 | 479 | 50-0.8 nM | 3.63E−11 |
|  | 5.5 | 7.31E+05 | 4.06E−05 | 463 | 50-0.8 nM | 5.56E−11 |
| 5E5VH5_VL8 | 7.4 | 1.77E+05 | 1.73E−04 | 309 | 50-0.8 nM | 9.75E−10 |
|  | 5.5 | 2.11E+05 | 2.42E−03 | 183 | 50-0.8 nM | 1.14E−08 |
| 5E5VH12_VL8 | 7.4 | 2.67E+05 | 1.63E−04 | 291 | 50-0.8 nM | 6.09E−10 |
|  | 5.5 | 1.88E+05 | 1.65E−03 | 523 | 50-0.8 nM | 8.79E−09 |
| 5E5VH5VH12_VLWT | 7.4 | 6.16E+04 | 3.05E−04 | 220 | 50-0.8 nM | 4.96E−09 |
|  | 5.5 | 1.56E+05 | 3.16E−03 | 381 | 50-0.8 nM | 2.02E−08 |
| 5E5VH5VH12_VL8 | 7.4 | 1.25E+05 | 2.80E−03 | 702 | 50-0.8 nM | 2.24E−08 |
|  | 5.5 | | | No binding detected | | |

All antibodies tested bound to human ApoC3 at pH 7.4, and had reduced affinity to ApoC3 at pH 5.5 (see Table 15). 5E5VH5_VLWT, 5E5VH12_VLWT, 5E5VH5_VL8, and 5E5VH12 VL8 show particularly pronounced pH-dependence.

Example 3: Effect of Anti-ApoC3 Antibodies on VLDL Uptake by Hepatocytes

In this example, the ability of anti-ApoC3 antibodies to attenuate VLDL uptake by hepatocytes was determined.

Briefly, HepG2 cells (ATCC HB-8065) were cultured on a poly-d-lysine coated surface in complete Minimum Essential Medium (MEM) supplemented with 10% FCS for 24 hours, and in complete MEM supplemented with 0.0125% bovine serum albumin (MEM-BSA medium) for another 24 hours. The cells were pre-incubated with 3 µM human ApoC3 protein (Athens Research and Technology) and 3 µM of a test antibody in the IgG$_1$ format for 15 minutes in fresh MEM-BSA medium, and 30 µg/mL ApoC3-depleted DiI-labeled VLDL (Kalen Biomedical, LLC #770130-9) was added to the medium. After a 4-hour incubation, the cells were further incubated with fresh complete MEM supplemented with 1% intralipid for 20 minutes. The amount of DiI-labeled VLDL taken up by the cells was determined by lysing the cells with isopropanol at room temperature for 15 minutes, measuring fluorescence of the DiI label in the lysate (ex=520 nm; em=580), calculating the amount of DiI-labeled VLDL using a standard curve, and normalizing the data based on the quantity of total protein in the lysate. Data was graphed using GraphPad Prism 6 and is reported as average +/−SEM. One-way ANOVA with multiple comparisons were calculated using GraphPad Prism 6.

Figure 1A:
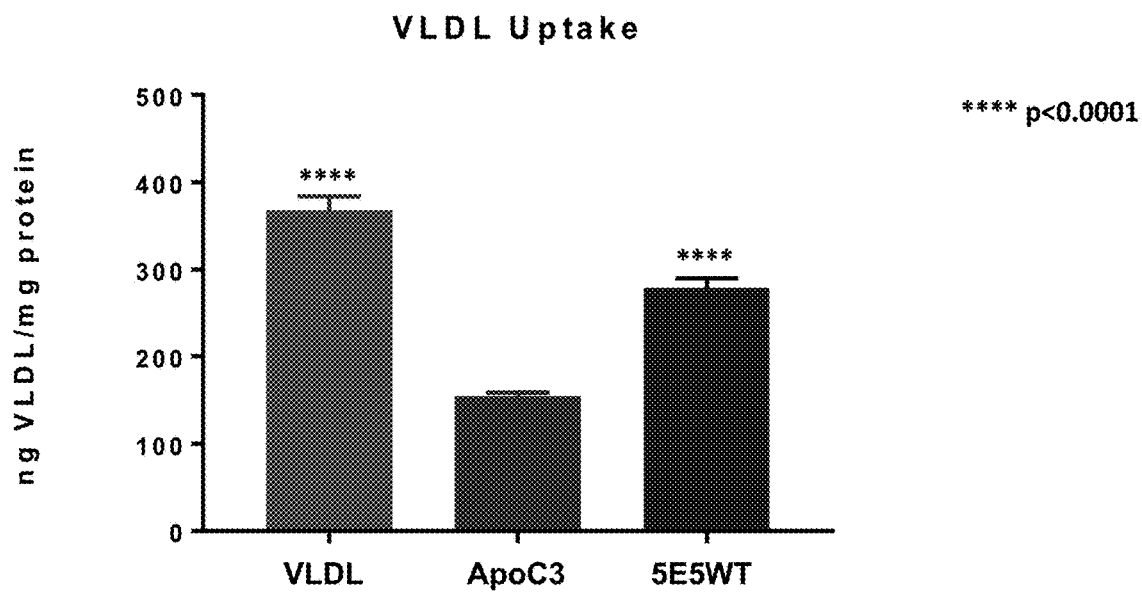
FIGS. 1A, 1B, and 1C are a series of graphs showing that the 5E5WT (FIG. 1A), 5E5VH5_VL8 (FIG. 1B), and 5E5VHWT_VL8 ("VL8"), 5E5VH12_VLWT ("VH12"), 5E5VH5_VLWT ("VH5"), and 5E5VH5_VL8 ("VH5_VL8") (FIG. 1C) antibodies attenuated the ability of ApoC3 to inhibit very low density lipoprotein (VLDL)
Figure 1B:
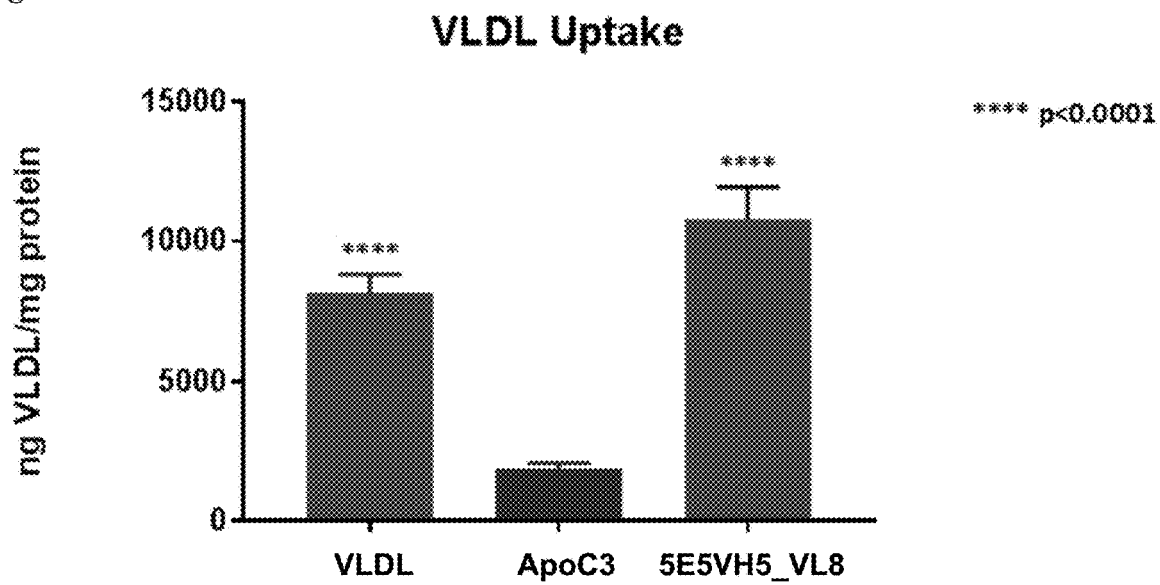
Figure 1C:
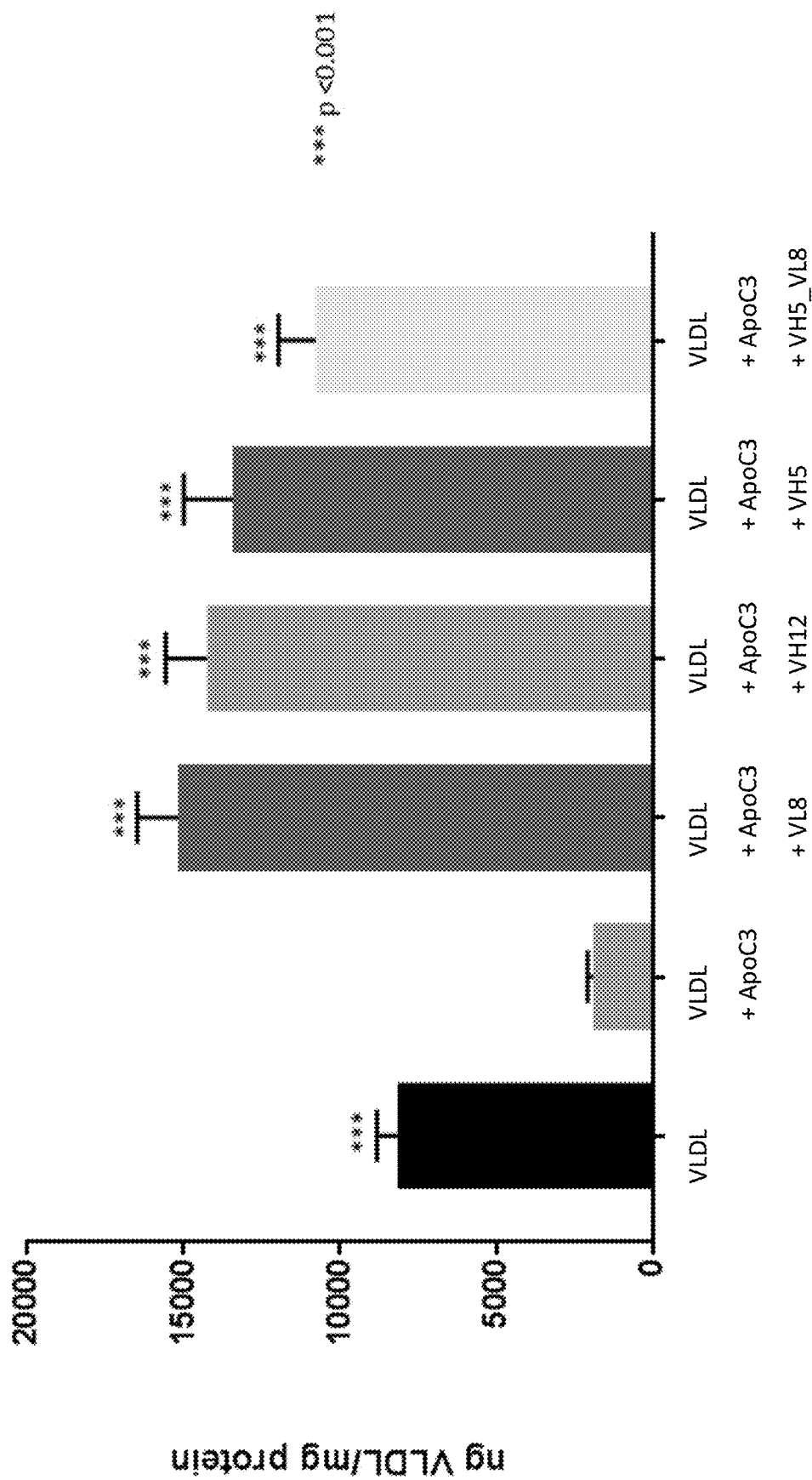

As shown in FIGS. 1A, 1B, and 1C, the 5E5WT, 5E5VHWT_VL8, 5E5VH5_VLWT, 5E5VH12_VLWT, and 5E5VH5_VL8 antibodies increased VLDL uptake by HepG2 cells. In particular, the 5E5VHWT_VL8, 5E5VH5_VLWT, 5E5VH12_VLWT, and 5E5VH5_VL8 antibodies all completely restored VLDL uptake in the presence of ApoC3.

Example 4: Pharmacokinetics and Pharmacodynamics of Anti-ApoC3 Antibodies

This example describes the in vivo characterization of the 5E5VH5_VL8 antibody using a mouse model having impaired triglyceride clearance due to transgenic expression of human ApoC3.

4.1 Generation of Mouse Model

Wild-type C57BL/6 male mice aged 60-63 days maintained on a standard chow diet were infected with $3 \times 10^{11}$ viral particles of an AAV8 vector harboring a human ApoC3 gene operably linked to a thyroxine binding globulin (TBG) promoter (RegenXBio) by intraperitoneal administration. Twelve days following the administration, blood samples were collected from retro-orbital sinus, and levels of human ApoC3 in the blood samples were measured by ELISA using a primary anti-ApoC3 antibody (Abcam rabbit polyclonal anti-human ApoC3 #ab21032) and a secondary ApoC3 antibody (Abcam goat polyclonal biotin-conjugate ApoC3 #ab21024). In the infected mice, the mean serum level of human ApoC3 was 9.9 µM. The mean circulating triglyceride level after a four-hour fasting was 163 mg/dL in these mice, whereas the mean circulating triglyceride level in control mice was 109 mg/dL (p=0.0065).

The mice were then grouped such that all groups had similar mean ApoC3 levels on Day 12. Fourteen days after the AAV infection, blood samples were collected from retro-orbital sinus to establish baseline (T=0) ApoC3 levels. 25 mg/kg of a test anti-ApoC3 human IgG$_1$ antibody was administered to each mouse by injection into the dorsal subcutaneous space. An anti-hen egg lysosome human IgG$_1$ antibody (HyHEL5) was used as an isotype control. Blood samples were collected from retro-orbital sinus 0, 2, 4, 8, and 24 hours after the administration of the test antibodies, and approximately every 2 days afterwards for 30 days. All animal studies were carried out in accordance with the recommendations in the Guide for the Care and Use of Laboratory Animals of the National Institutes of Health. All procedures were approved by the Institutional Animal Care and Use Committee of Vascumab, LLC.

4.2 Pharmacokinetics of Anti-ApoC3 Antibodies

Mice expressing human ApoC3 were generated and treated as described in Section 4.1. Plasma levels of the human IgG$_1$ antibodies were determined with an ELISA assay. Specifically, a 96-well plate (Griener #655061) was coated overnight at 4° C. with 50 µL primary IgG antibody (Fitzgerald 41-XG57 goat anti-human IgG Fc polyclonal) diluted in PBS. The plate was washed 4 times with 200 µL TBS-T, and blocked with 200 µL of blocking buffer consisting of 3% BSA (Roche BSA fraction V protease free #03 117 332 001) plus clear milk (Pierce Clear Milk Blocker #37587) in PBS for 90 minutes at 30° C. The blocking buffer was removed, and 50 µL of test sample diluted in blocking buffer was added and allowed to incubate for 2 hours at room temperature with rotation at 300 rpm. The plate was washed four times with 200 µL TBS-T, and 50 µL secondary antibody (Abcam goat anti-human IgG-Fc (biotin) polyclonal #ab97223) diluted in blocking buffer was added and allowed to incubate for 1 hour at room temperature with rotation at 300 rpm. The plate was washed once with TBS-T, and 50 µL SA-HRP (Abcam #64269) diluted 100-fold in PBS was added and allowed to incubate for 30 min at RT with rotation at 300 rpm. The plate was then washed 4 times with 200 μL TBS-T, and developed with 80 μL TMB. The chromogenic reaction was terminated by 50 μL 0.5 N HCL. Absorbance was read at the wavelength of 450 nm. The amounts of human IgG in test wells were calculated from a 4-parameter fit of a standard curve (Molecular Devices) constructed using the purified test antibody. This method detects human ApoC3 specifically, and does not cross-react with mouse ApoC3.

As shown in FIG. 2A, the 5E5 antibody was rapidly degraded in mice expressing human ApoC3. This can be explained by the rapid turnover of ApoC3 through uptake of ApoC3-containing lipid particles. The 5E5VH5_VL8 antibody, which has a reduced affinity to ApoC3 at lower pH, can dissociate from ApoC3 in acidic organelles and return to the bloodstream via endosomal recycling. The half-life of 5E5VH5_VL8 is about one week, which is similar to the half-life of the isotype control antibody HyHel5 (an antibody that does not bind to a specific antigen in mice). The plasma level of 5E5VH5_VL8 returned to the baseline about one month after the injection. The extended half-life of 5E5VH5_VL8 makes this antibody an excellent candidate for clinical application, due to the low frequency of administration required to maintain a therapeutic level of the antibody in serum.

4.3 Pharmacodynamics of Anti-ApoC3 Antibodies

Mice expressing human ApoC3 were generated and treated as described in Section 4.1. Plasma levels of human ApoC3 and ApoB were determined with an ELISA assay. Specifically, a 96-well plate (Griener #655061) was coated overnight at 4° C. with 50 μL primary ApoC3 antibody (Abcam rabbit polyclonal anti-human ApoC3 #ab21032) or 50 μL primary ApoB antibody (Meridian Life Sciences goat polyclonal anti-human ApoB #K45253G) diluted in PBS. The plate was washed 4 times with 200 μL TBS-T, and blocked with 200 μL of blocking buffer (Pierce Clear Milk Blocker #37587 in PBS) for 90 minutes at 30° C. The blocking buffer was removed, and 50 μL of test sample diluted in blocking buffer was added and allowed to incubate for 2 hours at room temperature with rotation at 300 rpm. The plate was washed four times with 200 μL TBS-T, and 50 μL secondary ApoC3 antibody (Abcam goat polyclonal biotin-conjugate ApoC3 #ab21024) or secondary ApoB antibody (Meridian Life Sciences goat polyclonal biotin-conjugate ApoB48/100 #34003G) diluted in blocking buffer was added and allowed to incubate for 1 hour at room temperature with rotation at 300 rpm. The plate was washed once with TBS-T, and 50 μL SA-HRP (Abcam #64269) diluted 100-fold in PBS was added and allowed to incubate for 30 minutes at room temperature with rotation at 300 rpm. The plate was then washed 4 times with 200 μL TBS-T, and developed with 80 μL TMB (Thermo Ultra-TMB ELISA #34028) followed by 50 μL 0.5 N HCL. Absorbance was read at 450 nm. The amount of ApoC3 in test wells was calculated from a 4-parameter fit of a standard curve (Molecular Devices) constructed using purified ApoC3 (Athens Research and Technology). The amount of ApoB in test wells was calculated from a 4-parameter fit of a standard curve (Molecular Devices) constructed using mouse VLDL isolated by centrifugation (ApoB content is assumed to be 20% of total protein content). Data was calculated and plotted as percentage values relative to the corresponding levels in mice treated with the HyHel5 control antibody.

As shown in FIGS. 2B and 2C, the 5E5 antibody reduced the plasma levels of human ApoC3 and ApoB initially, but the levels returned to normal after about 2 days. By contrast, 5E5VH5_VL8 reduced the plasma levels of human ApoC3 and ApoB for about one month. This long duration of efficacy was consistent with the long half-life of 5E5VH5_VL8, and confirmed that 5E5VH5_VL8 would be an excellent clinical candidate.

Example 5: Humanization of Anti-ApoC3 Antibodies

Humanized variants of 5E5VH5_VL8 were generated according to the "germlining" methods described in WO2012123586A1. Briefly, human germline genes segments with the same canonical fold structure and the highest amino acid sequence identity to the VH and VL regions of 5E5VH5_VL8 were identified by comparison with known human germline gene sequences. The closest human heavy chain and light chain germline sequences were human IGHV3-23*01 and human IGKV2-28*01, respectively. A phage display Fab library of 5E5VH5_VL8 variants was constructed that incorporated humanizing mutations at the amino acid residues of 5E5VH5_VL8 differing from the human IGHV3-23*01 and IGKV2-28*01 germline sequences, with llama and the human residues at each targeted position being equally represented in the library. Mutations to remove the sequence liability motifs DG, DS, NR, or M were also incorporated into the library. Humanized 5E5VH5_VL8 variants with the best target binding characteristics (e.g., high affinity binding to ApoC3 at pH 7.4, but much reduced affinity to ApoC3 at pH 5.5) were identified after several rounds of affinity-driven phage display selections.

Twenty humanized anti-ApoC3 antibodies that retained high affinity, pH-dependent binding were identified from the initial selection and screening described above. The VH and Vκ coding sequences of these antibodies were cloned into an expression vector, and produced in ExpiCHO-S cells as full length $IgG_1$ molecules. The antibodies were then purified using the Hitrap MabSelect Sure column (GE, cat. nr. 11-0034-94) on an ÄKTA Pure system. The antibodies were eluted using 1.0 ml of 0.1 M citrate buffer at pH 3.0, and the eluted fractions were collected in tubes containing 0.1 ml Tris-HCl pH 9.0 for neutralization. Antibody containing fractions were pooled and desalted in 1× phosphate buffered saline solution (PBS; NaCl 137 mM, KCl 3 mM, Na2HPO4 8 mM, KH2PO4 15 mM, pH7.4) using a HiTrap desalting column on the ÄKTA Pure system. Protein concentrations were determined by measuring the absorbance at 280 nm and correction with extinction coefficient as follows: (A280 nm-A340 nm)/c (extinction coefficient in g/L). The purified samples were examined by SDS-PAGE under reducing and non-reducing conditions to confirm the correct size and purity of the samples.

Two different surface plasmon resonance (SPR) assays were performed to evaluate the pH dependent association and dissociation parameters of the humanized anti-ApoC3 antibodies. The methods and results of the two assays are described below.

5.1 SPR Analysis of Humanized Anti-ApoC3 Antibody Binding to Immobilized ApoC3

Biotinylated native human ApoC3 was captured on a streptavidin coated SPR chip (GE Healthcare, cat. nr. BR100032) at pH 7.4, in accordance with the method provided by Biacore, by injection of 20 μl 10 μg/ml biotinylated native human ApoC3 reaching the surface density of approximately 500 RU. 60 μL of test antibody in 1-50 nM range diluted in HBS-EP buffer (GE, cat #BR-1008-26; 0.010 M HEPES, 0.150M NaCl, 3 mM EDTA, 0.05% (v/v) surfactant P20, pH 7.4) was injected and passed through the flow cells at a flow rate of 30 μl/min, followed by an off-rate wash at pH7.4 for 5 min. After the dissociation, the flow cell surfaces were regenerated by injecting 10 μl of 10 mM NaOH/1 M NaCl and 10 μl of 10 mM glycine at pH1.5. The assay was repeated at pH5.5 using the same general protocol, where the running and sample dilution buffer was replaced by a HBS-EP buffer supplemented with citrate buffer to 10 mM final concentration and pH adjusted to 5.5.

The resulting sensorgrams were analyzed using the BIAevaluation 4.1 software using Langmuir 1:1 binding model to derive binding kinetics. Data was zero adjusted and the reference cell sensorgrams were subtracted. Sensorgrams were double referenced to no-analyte blank assay. Fitted parameters were considered not applicable if off-rate values were below the equipment's detection limit of kd: $1\times10^{-6}$ 1/s.

An overview of the calculated kinetic parameters is presented in Table 16 for the generated humanized antibodies. FIGS. 3A-E show the overlaid sensorgrams for each generated humanized mAb at the two assay pH values, at uniform 25 nM mAb concentrations.

As shown in FIGS. 3A-E, mAb1 to mAb6 demonstrated very low off-rates at both pH 7.4 and pH5.5. Their apparent affinity at pH5.5 was improved relative to 5E5VH5_VL8, and pH-dependent target binding was not observed. The mAb7 antibody shows clear pH dependent target binding, with high off-rate at pH 5.5. However, the Rmax values in the binding phase at both pH values were higher than the ones of 5E5VH5_VL8. The mAb8 to mAb12 antibodies demonstrated very low off rates at pH 7.4, and higher Rmax levels at pH5.5 than at pH 7.4. Their apparent affinity at pH5.5 was improved relative to 5E5VH5_VL8, and pH-dependent target binding was not observed. The mAb13 and mAb14 antibodies were generated by grafting the HCDR and LCDR sequences into the closest human germline framework sequences, and showed clear pH-dependent target binding characteristics. However, their affinity to human ApoC3 was reduced at pH 7.4 relative to 5E5VH5_VL8. The mAb15, mAb17, and mAb19 antibodies did not contained the histidine residue at the LCDR3 (Q90H), but displayed the desired pH-dependent target binding charac-

TABLE 16

SPR analysis of humanized ApoC3 antibody binding to immobilized ApoC3

| Antibody | HBS-EP | ka (1/Ms) | kd (1/s) | Rmax (RU) | Conc of analyte | KA (1/M) | KD (M) | KD (nM) | KD pH5.5/ KD pH7.4 |
|---|---|---|---|---|---|---|---|---|---|
| 5E5 | pH7.4 | 3.50E+05 | 1.79E−05 | 475 | 50 nM-0.8 nM | 1.95E+10 | 5.12E−11 | 0.05 | 0.97 |
|  | pH5.5 | 3.40E+05 | 1.70E−05 | 519 | 50 nM-0.8 nM | 2.01E+10 | 4.99E−11 | 0.05 |  |
| 5E5VH5_VL8 | pH7.4 | 1.77E+05 | 1.73E−04 | 309 | 50 nM-0.8 nM | 1.03E+09 | 9.75E−10 | 0.98 | 11.7 |
|  | pH5.5 | 2.11E+05 | 2.42E−03 | 183 | 50 nM-0.8 nM | 8.74E+07 | 1.14E−08 | 11.40 |  |
| 5E5VH12 | pH7.4 | 6.56E+05 | 1.12E−05 | 598 | 25 nM-0.8 nM | 5.84E−10 | 1.71E−11 | 0.02 | 27.6 |
|  | pH5.5 | 3.02E+05 | 1.43E−04 | 684 | 50 nM-0.8 nM | 2.12E+09 | 4.72E−10 | 0.47 |  |
| mAb1 | pH7.4 | 2.61E+05 | 1.18E−05 | 692 | 50 nM-0.8 nM | 2.20E+10 | 4.54E−11 | 0.05 | 5.22 |
|  | pH5.5 | 4.40E+05 | 1.04E−04 | 669 | 25 nM-0.8 nM | 4.23E+09 | 2.37E−10 | 0.24 |  |
| mAb2 | pH7.4 | 2.45E+05 | 1.35E−05 | 696 | 50 nM-0.8 nM | 1.81E+10 | 5.52E−11 | 0.06 | 5.13 |
|  | pH5.5 | 4.35E+05 | 1.23E−04 | 668 | 25 nM-0.8 nM | 3.54E+09 | 2.83E−10 | 0.28 |  |
| mAb3 | pH 7.4 | 2.12E+05 | 2.33E−05 | 697 | 50 nM-0.8 nM | 9.11E+09 | 1.10E−10 | 0.11 | 3.19 |
|  | pH5.5 | 3.63E+05 | 1.27E−04 | 673 | 25 nM-0.8 nM | 2.85E+09 | 3.51E−10 | 0.35 |  |
| mAb4 | pH 7.4 | 2.43E+05 | 1.13E−06 | 671 | 50 nM-0.8 nM | 2.15E+11 | 4.64E−12 | n.a. | n.a. |
|  | pH5.5 | 4.16E+05 | 1.56E−04 | 648 | 25 nM-0.8 nM | 2.67E+09 | 3.74E−10 | 0.37 |  |
| mAb5 | pH 7.4 | 2.37E+05 | 3.51E−05 | 668 | 50 nM-0.8 nM | 6.76E+09 | 1.48E−10 | 0.15 | 2.33 |
|  | pH5.5 | 4.19E+05 | 1.45E−04 | 628 | 25 nM-0.8 nM | 2.90E+09 | 3.45E−10 | 0.35 |  |
| mAb6 | pH 7.4 | 2.22E+05 | 1.33E−05 | 680 | 50 nM-0.8 nM | 1.67E+10 | 5.99E−11 | 0.06 | 5.79 |
|  | pH5.5 | 4.25E+05 | 1.48E−04 | 608 | 25 nM-0.8 nM | 2.88E+09 | 3.47E−10 | 0.35 |  |
| mAb7 | pH 7.4 | 3.64E+05 | 3.37E−05 | 773 | 50 nM-0.8 nM | 1.08E+10 | 9.28E−11 | 0.09 | 52.7 |
|  | pH5.5 | 6.56E+05 | 3.21E−03 | 523 | 25 nM-0.8 nM | 2.05E+08 | 4.89E−09 | 4.89 |  |
| mAb8 | pH 7.4 | 2.37E+05 | 2.41E−05 | 537 | 50 nM-0.8 nM | 9.83E+09 | 1.02E−10 | 0.10 | 7.34 |
|  | pH5.5 | 4.90E+05 | 3.67E−04 | 558 | 25 nM-0.8 nM | 1.34E+09 | 7.49E−10 | 0.75 |  |
| mAb9 | pH 7.4 | 2.23E+05 | 3.32E−05 | 548 | 50 nM-0.8 nM | 6.71E+09 | 1.49E−10 | 0.15 | 5.09 |
|  | pH5.5 | 4.86E+05 | 3.69E−04 | 566 | 25 nM-0.8 nM | 1.32E+09 | 7.59E−10 | 0.76 |  |
| mAb10 | pH 7.4 | 2.21E+05 | 2.12E−05 | 617 | 50 nM-0.8 nM | 1.05E+10 | 9.56E−11 | 0.10 | 2.82 |
|  | pH5.5 | 4.17E+05 | 1.13E−04 | 557 | 25 nM-0.8 nM | 3.70E+09 | 2.70E−10 | 0.27 |  |
| mAb11 | pH 7.4 | 2.19E+05 | 3.80E−05 | 612 | 50 nM-0.8 nM | 5.77E+09 | 1.73E−10 | 0.17 | 1.91 |
|  | pH5.5 | 4.45E+05 | 1.47E−04 | 555 | 25 nM-0.8 nM | 3.02E+09 | 3.31E−10 | 0.33 |  |
| mAb12 | pH 7.4 | 2.28E+05 | 1.49E−05 | 635 | 50 nM-0.8 nM | 1.53E+10 | 6.55E−11 | 0.07 | 2.12 |
|  | pH5.5 | 4.83E+05 | 6.73E−05 | 530 | 25 nM-0.8 nM | 7.18E+09 | 1.39E−10 | 0.14 |  |
| mAb13 | pH 7.4 | 1.10E+05 | 4.61E−04 | 447 | 50 nM-0.8 nM | 2.38E+08 | 4.19E−09 | 4.19 | 1.33 |
|  | pH5.5 | 4.79E+05 | 2.67E−03 | 164 | 25 nM-0.8 nM | 1.80E+08 | 5.56E−09 | 5.56 |  |
| mAb14 | pH 7.4 | 1.44E+05 | 4.27E−04 | 423 | 50 nM-0.8 nM | 3.38E+08 | 2.96E−09 | 2.96 | 7.20 |
|  | pH5.5 | 3.70E+05 | 7.88E−03 | 115 | 25 nM-0.8 nM | 4.70E+07 | 2.13E−08 | 21.30 |  |
| mAb15 | pH 7.4 | 5.16E+05 | 2.77E−06 | 951 | 50 nM-0.8 nM | 1.86E+11 | 5.38E−12 | n.a. | n.a. |
|  | pH5.5 | 7.05E+05 | 2.49E−04 | 753 | 25 nM-0.8 nM | 2.83E+09 | 3.53E−10 | 0.35 |  |
| mAb16 | pH 7.4 | 5.46E+05 | 3.75E−04 | 813 | 50 nM-0.8 nM | 1.46E+09 | 6.87E−10 | 0.69 | 10.8 |
|  | pH5.5 | 1.63E+06 | 1.21E−02 | 282 | 25 nM-0.8 nM | 1.34E+08 | 7.44E−09 | 7.44 |  |
| mAb17 | pH 7.4 | 5.03E+05 | 2.33E−05 | 891 | 50 nM-0.8 nM | 2.15E+10 | 4.64E−11 | 0.05 | 7.37 |
|  | pH5.5 | 8.06E+05 | 2.76E−04 | 746 | 25 nM-0.8 nM | 2.92E+09 | 3.42E−10 | 0.34 |  |
| mAb18 | pH 7.4 | 6.28E+05 | 8.38E−04 | 721 | 50 nM-0.8 nM | 7.49E+08 | 1.33E−09 | 1.33 | 6.48 |
|  | pH5.5 | 1.79E+06 | 1.55E−02 | 179 | 25 nM-0.8 nM | 1.16E+08 | 8.62E−09 | 8.62 |  |
| mAb19 | pH 7.4 | 6.40E+05 | 2.90E−05 | 774 | 50 nM-0.8 nM | 2.21E+10 | 4.53E−11 | 0.05 | 9.21 |
|  | pH5.5 | 7.10E+05 | 2.96E−04 | 736 | 25 nM-0.8 nM | 2.40E+09 | 4.17E−10 | 0.42 |  |
| mAb20 | pH 7.4 | 8.31E+05 | 4.87E−04 | 649 | 25 nM-0.8 nM | 1.71E+09 | 5.86E−10 | 0.59 | 16.11 |
|  | pH5.5 | 2.27E+06 | 2.14E−02 | 202 | 25 nM-0.8 nM | 1.06E+08 | 9.44E−09 | 9.44 |  |

Figure 3A:
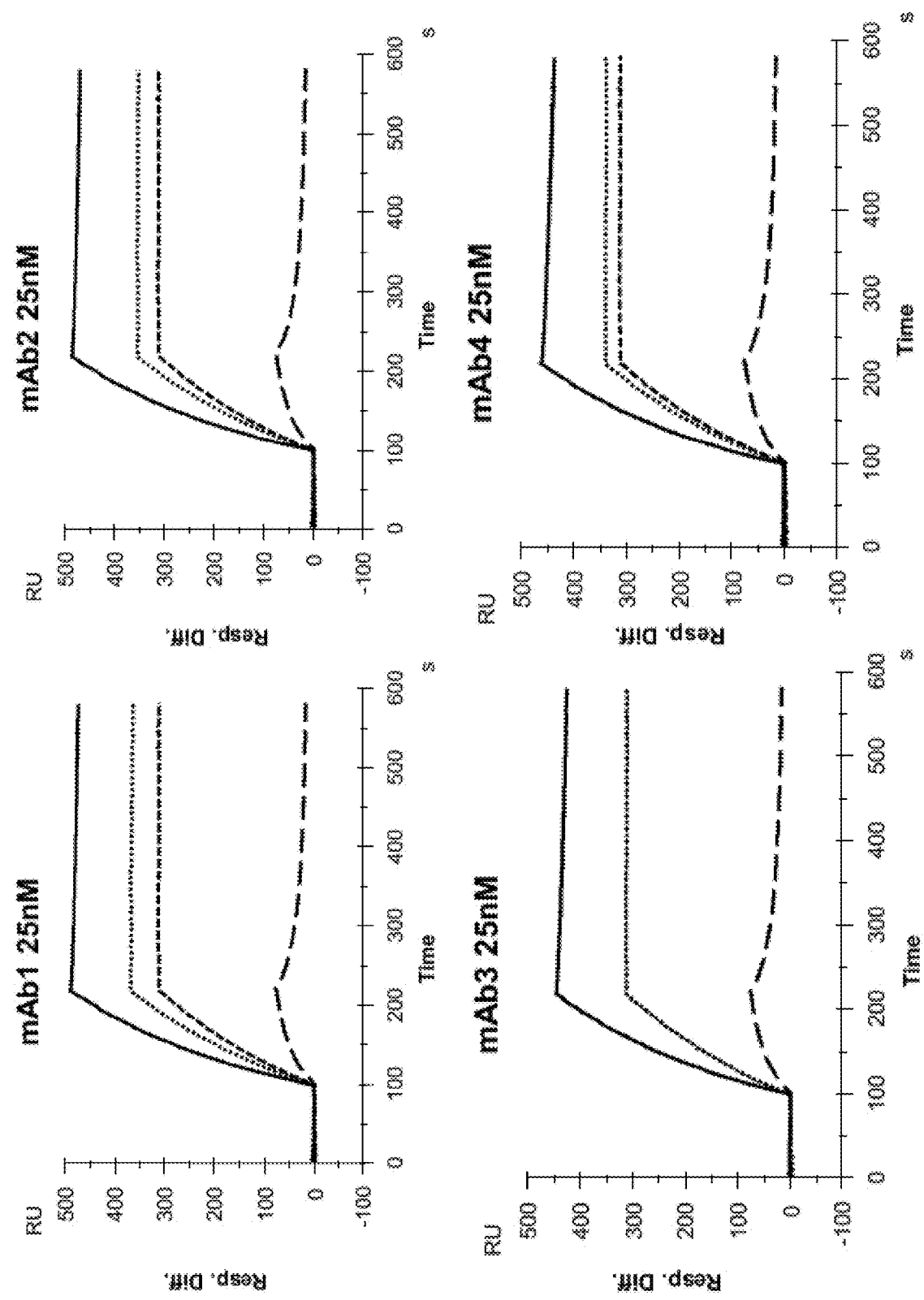
Figure 3B:
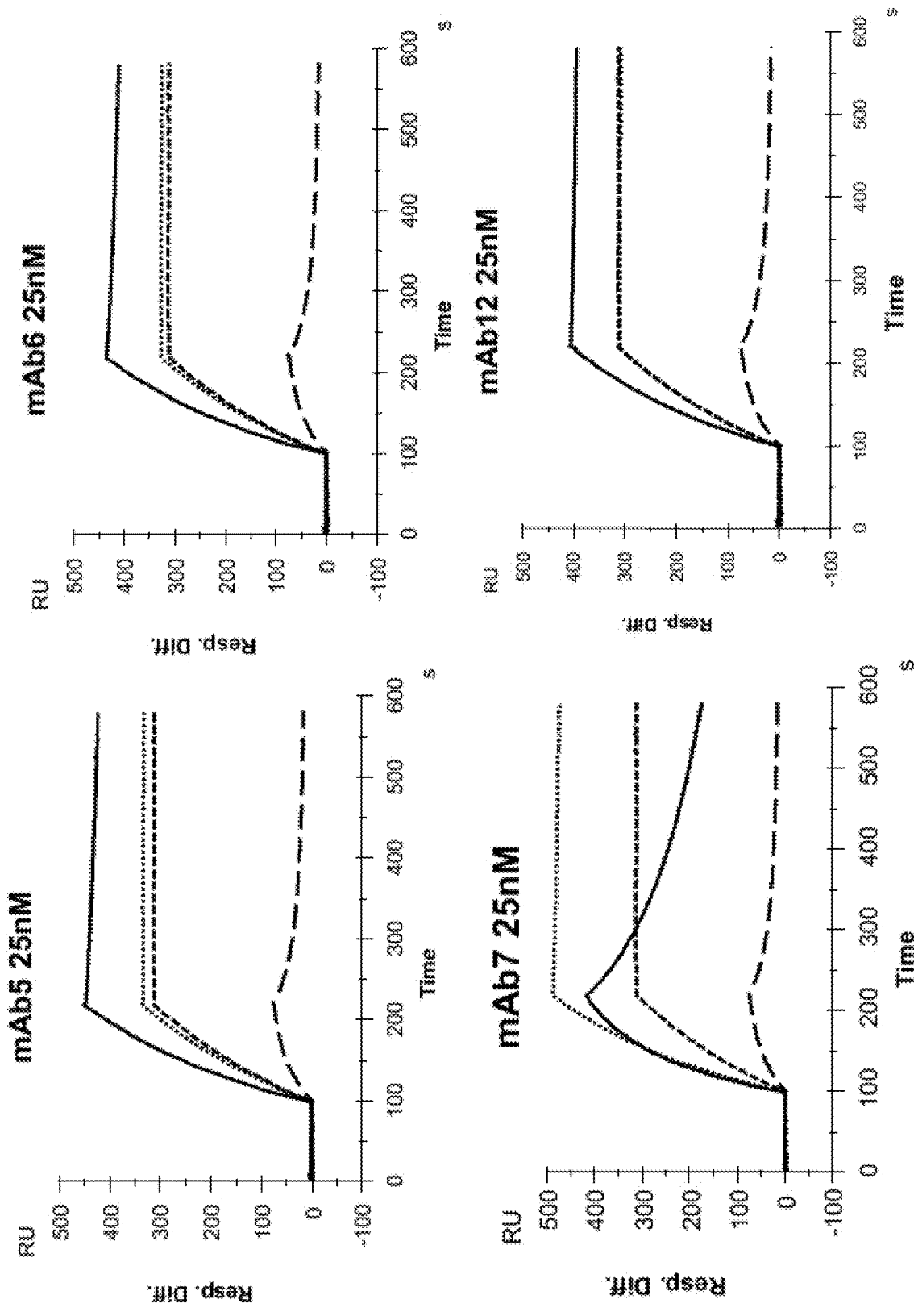
Figure 3C:
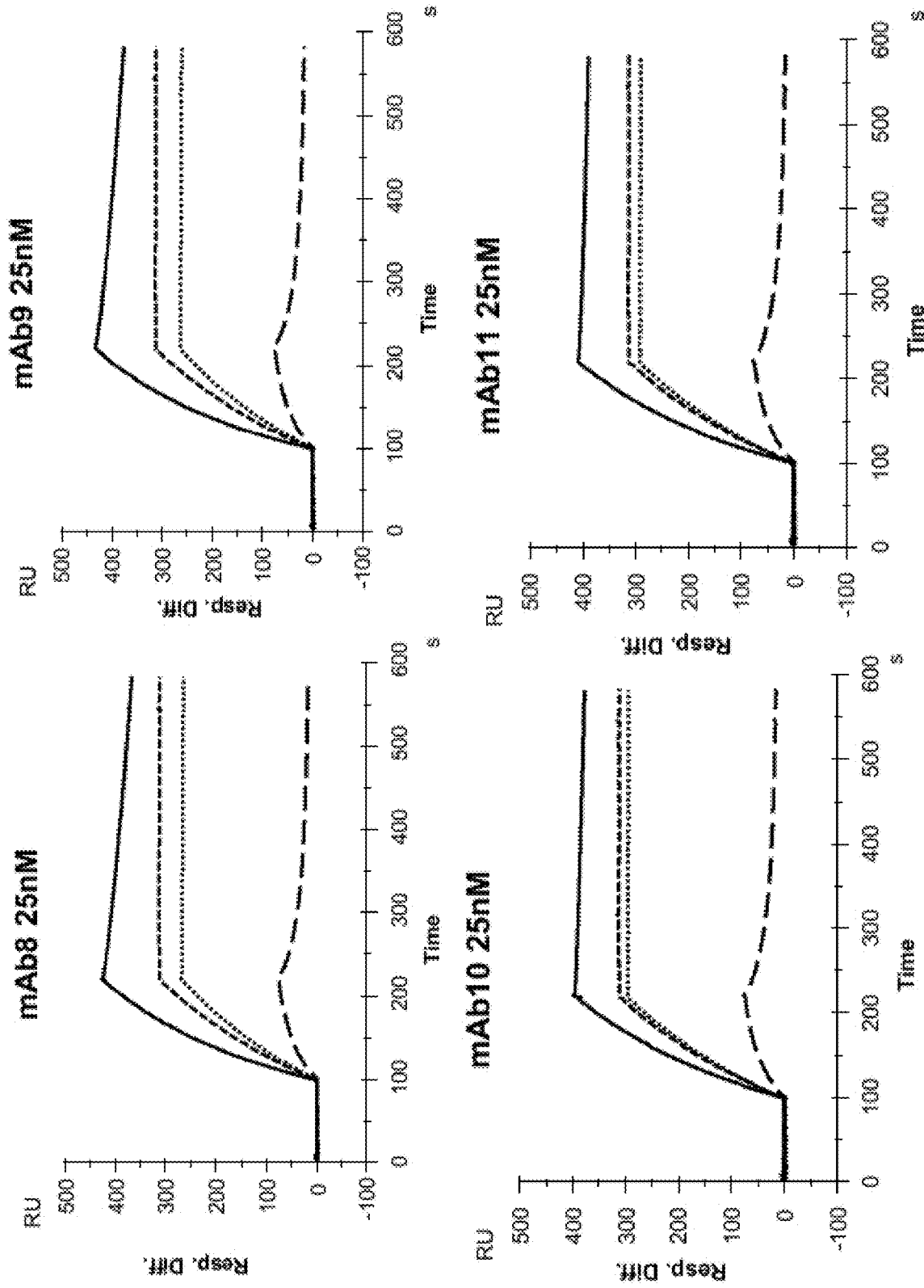
Figure 3D:
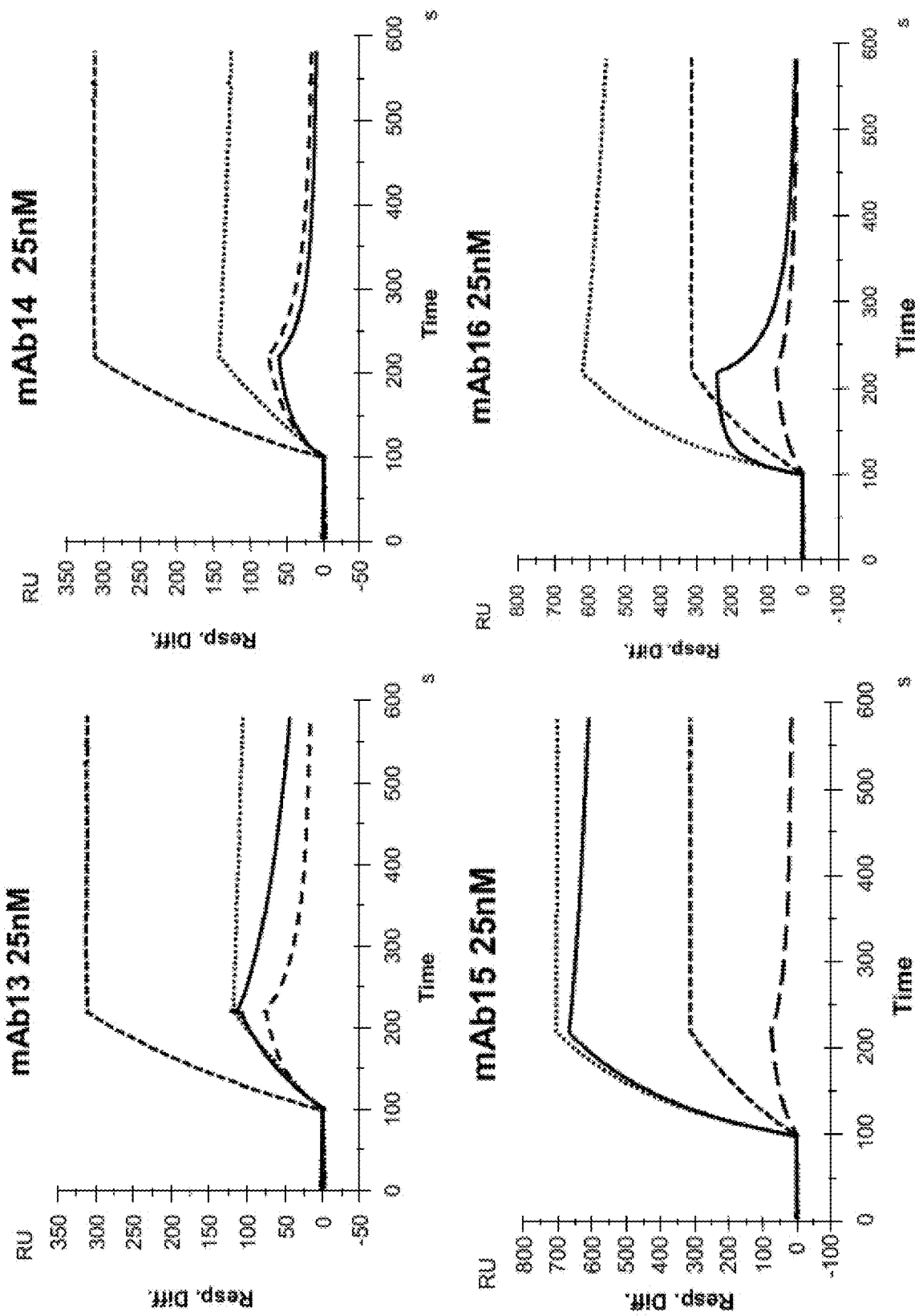
Figure 3E:
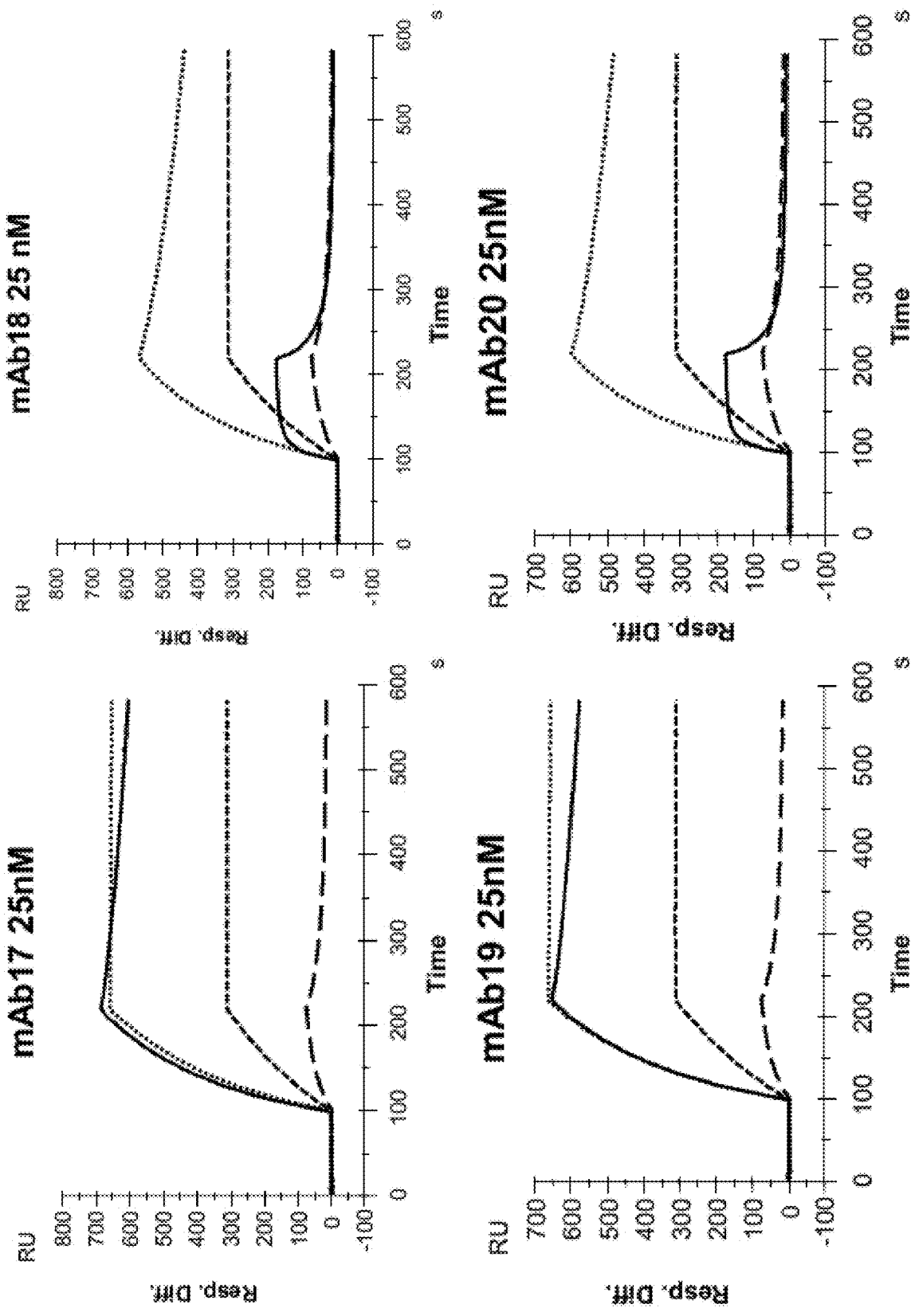
Figure 4A:
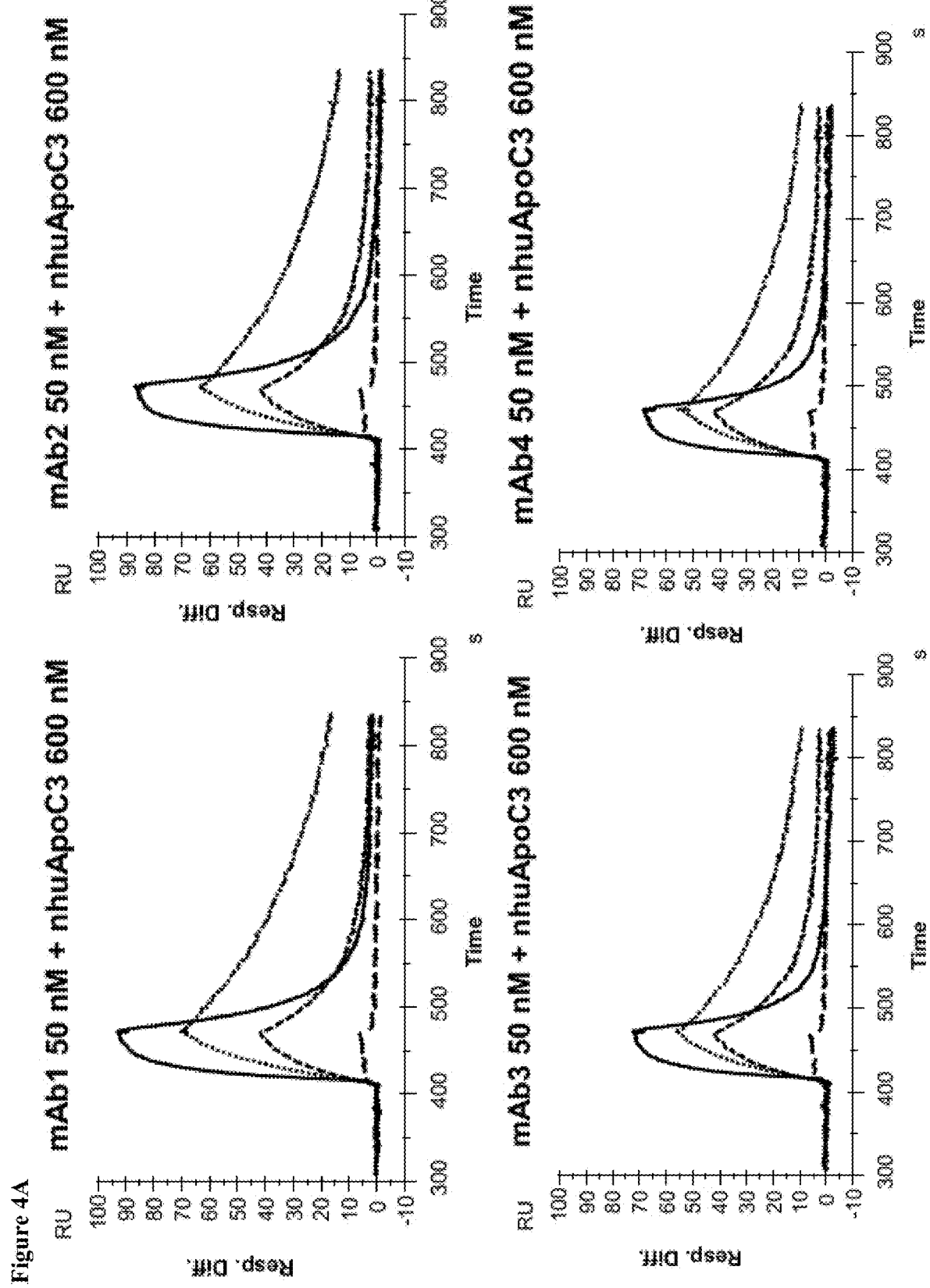
Figure 4B:
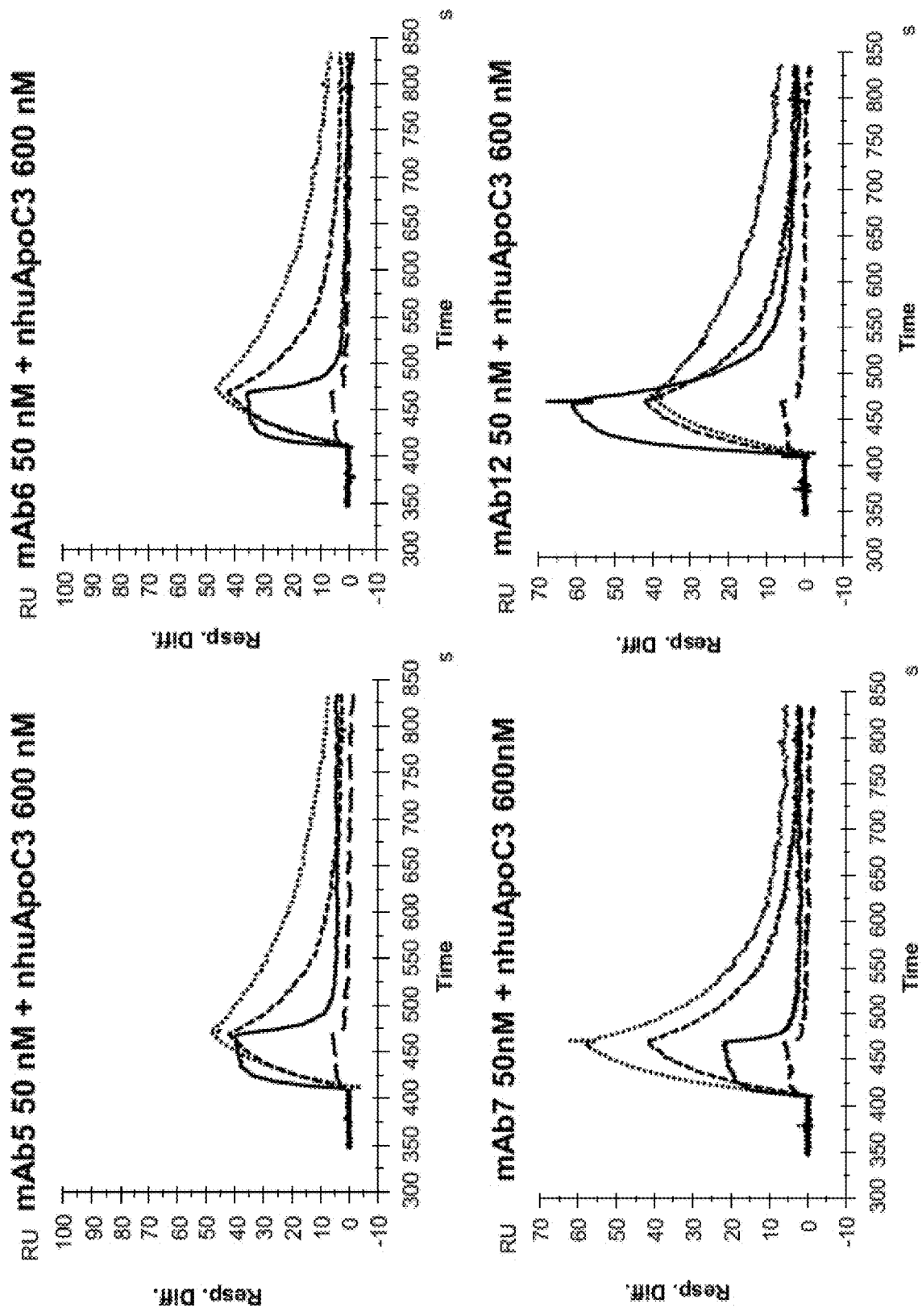
Figure 4C:
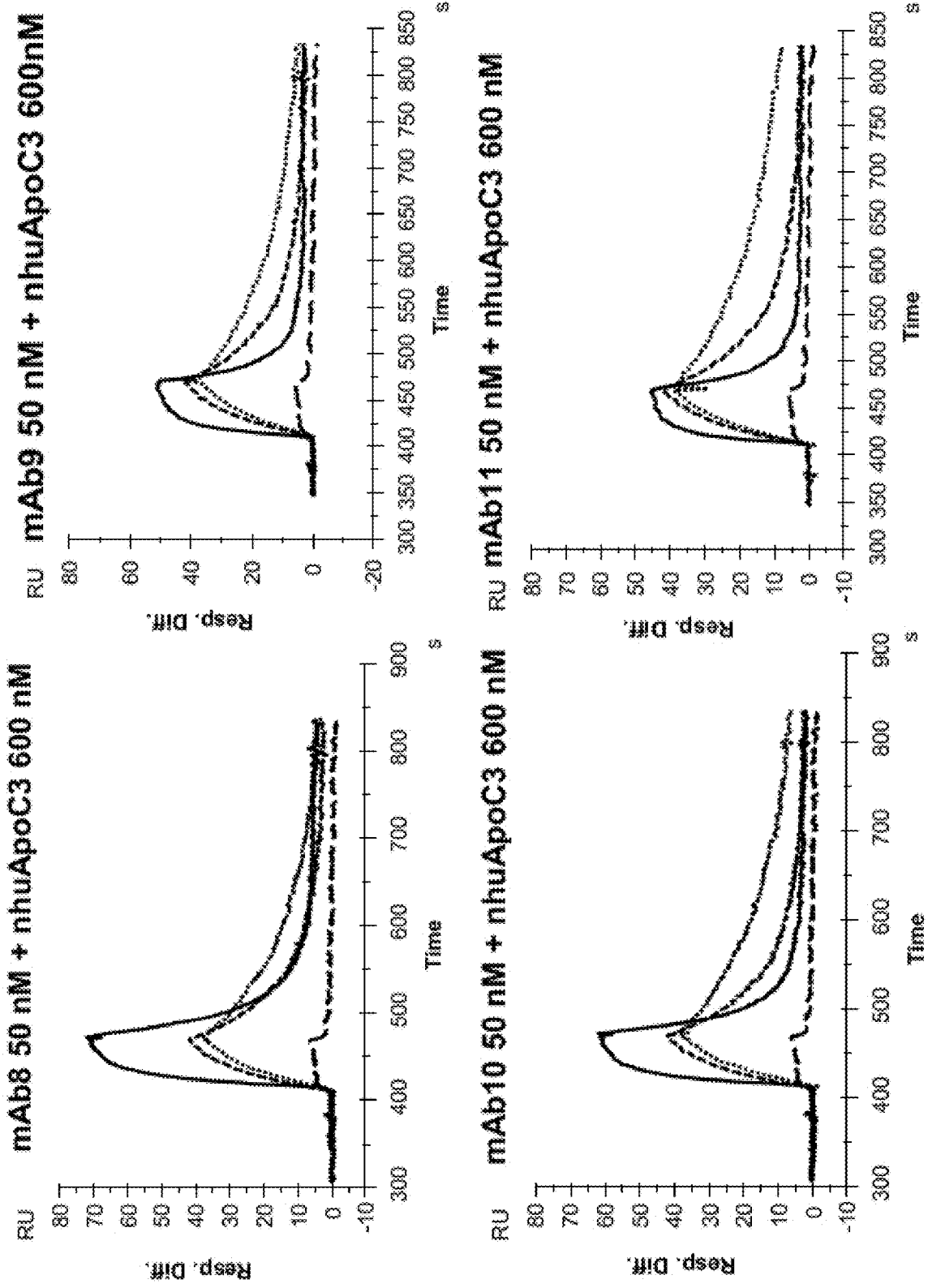
Figure 4D:
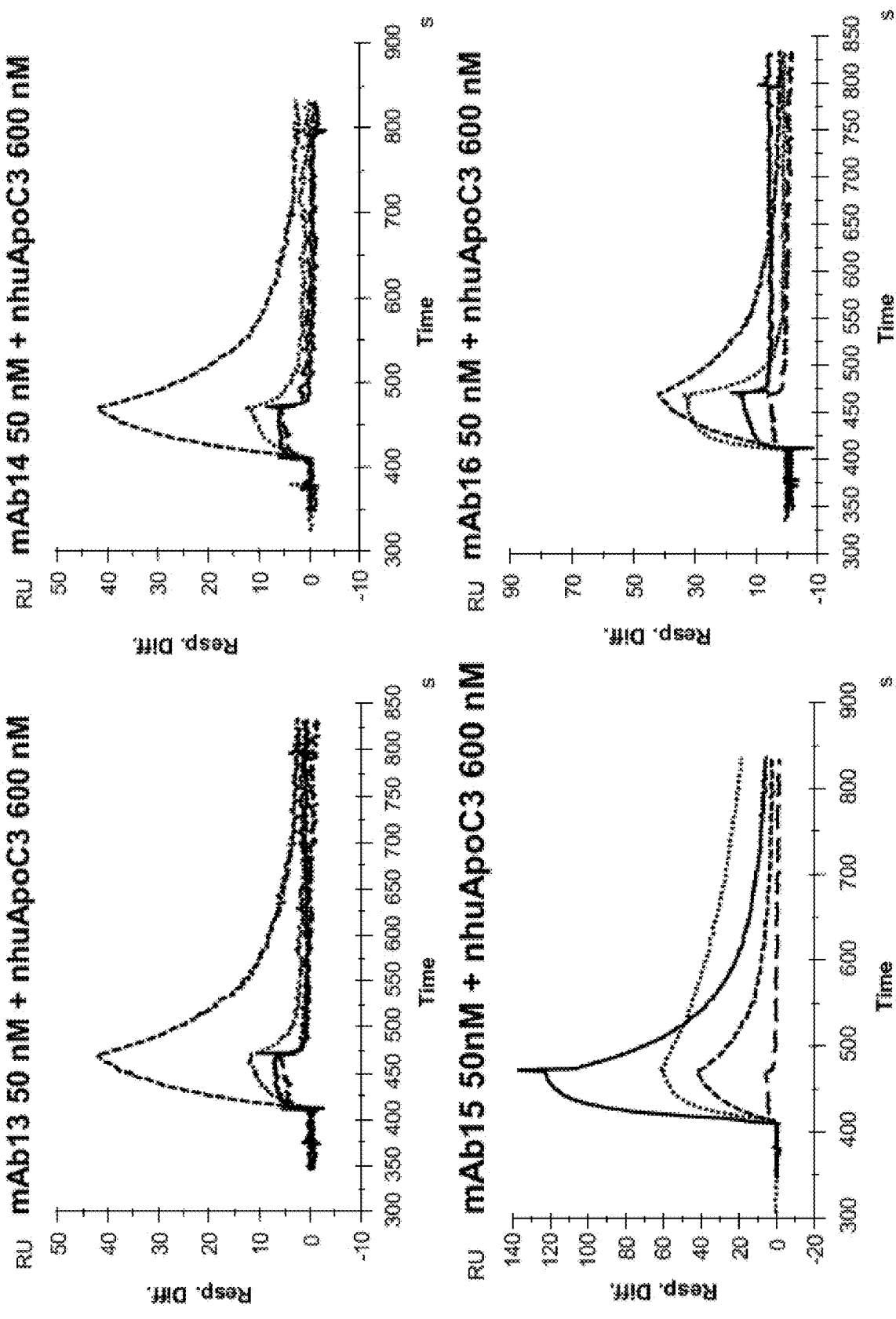
Figure 4E:
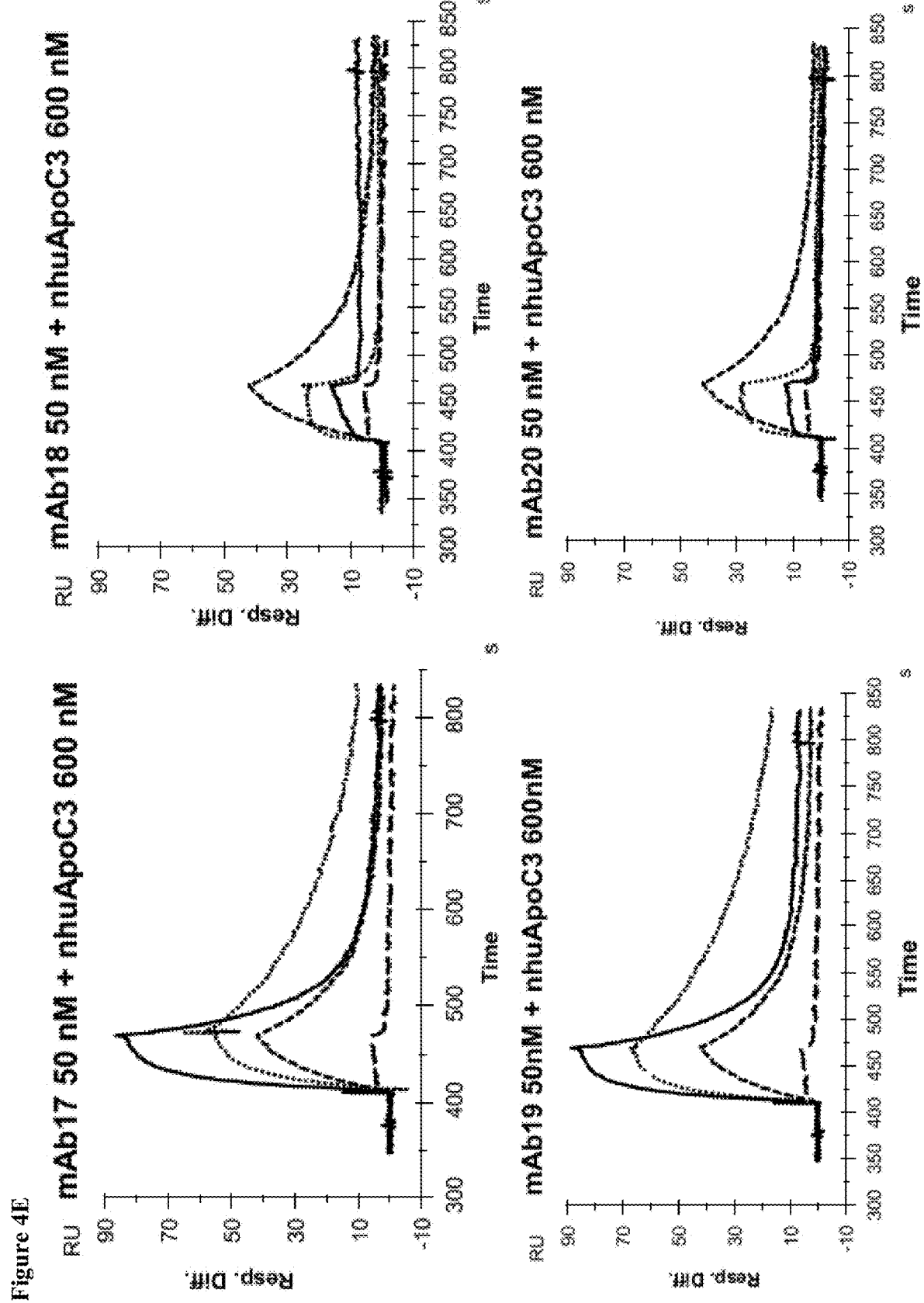

* assay at pH7.4 resulted in off-rate reading below the equipment's limit of detection
n.a. not applicable teristics in the screen. The sequences of mAb16, mAb18, and mAb20 antibodies were identical to mAb15, mAb17, and mAb19, respectively, except that the residue corresponding to H90 5E5VH5_VL8 was histidine. As shown in FIGS. 3D and 3E, mAb16, mAb18, and mAb20 showed clear pH-dependent target binding, due to the reduced affinity to the target at pH 5.5 and increased off-rate at pH 7.4.

5.2 SPR Analysis of ApoC3 Binding to Immobilized Humanized Anti-ApoC3 Antibodies An inverted SPR assay was designed in which a test antibody was captured on an SPR chip, human ApoC3 protein was injected, and binding of ApoC3 to the antibody was measured. Specifically, goat anti-human IgG Fcγ-specific antibody (Jackson ImmunoResearch, Cat. nr. 109-005-098) was immobilized on a CM5 chip surface (GE Healthcare, cat. nr. BR100012). The immobilization was performed in accordance with the method provided by Biacore/GE using the NHS/EDC kit (Biacore AB, Cat.nr. BR-1000-50): after activation of the chip, a solution of 30 μg/ml of anti-human Fcγ antibody in 10 mM acetate buffer with pH of 5.0 was prepared and injected until the surface density reached approximately 10000 RU. The analytical cycle comprised the following steps:

(1) antibody capture: injection of the antibody at a 50 nM concentration at pH7.4 or pH5.5 diluted in HBS-EP buffer (GE, cat. nr. BR-1008-26; 0.010 M HEPES, 0.150M NaCl, 3 mM EDTA, 0.05% (v/v) surfactant P20, pH 7.4) and allowing to be captured by the high affinity anti huFcγ antibody up to 800 RUs;

(2) baseline stabilization: injection of 100 μl of HBS-EP buffer at the 30 μl/ml flow rate;

(3) target binding: injection of 60 μl of target ApoC3 protein diluted in HBS-EP buffer at 400 nM, 200 nM, 100 nM and 50 nM concentrations;

(4) off-rate wash: injection of HBS-EP buffer at 30 μl/ml flow rate for 5 min for assessment of the dissociation phase;

(5) regeneration of the chip by injecting 20 μl of 10 mM glycine at pH1.5.

The resulting sensorgrams were analyzed using the BIAevaluation 4.1 software using Langmuir 1:1 binding model to derive binding kinetics. Data was zero adjusted, the reference cell sensorgrams were subtracted and the no analyte blank assay was used for double referencing the sensorgrams corresponding to the analyte injections. The dissociation and association phase sensorgrams were fitted separately for the 4 different concentration curves. Sensorgrams were excluded from the fitting if maximum RU values reached were below the detection limit of the equipment (<5 RU), Biacore 3000 (Biacore AB).

An overview of the calculated kinetic parameters is presented in Table 17 for the generated humanized antibodies. FIGS. 4A-E show the binding characteristics for the generated variants. The off-rate of every antibody was increased in this set-up, due to the different presentation of the target protein.

TABLE 17

SPR analysis of ApoC3 binding to immobilized, humanized anti-ApoC3 antibodies

| Antibody | HBS-EP | ka (1/Ms) | kd (1/s) | Rmax (RU) | Conc of target | KA (1/M) | KD (M) | KD (nM) | KD (nM) pH5.5/pH7.4 |
|---|---|---|---|---|---|---|---|---|---|
| 5E5VH5_VL8 | pH7.4 | 4.27E+04 | 1.27E−02 | 68.1 | 600-50 nM | 3.35E+06 | 2.98E−07 | 298 | n/a |
|  | pH5.5 | n/a | n/a | n/a | 600-50 nM | n/a | n/a | n/a |  |
| mAb1 | pH7.4 | 5.76E+04 | 4.26E−03 | 86.4 | 600-50 nM | 1.35E+07 | 7.39E−08 | 74 | 3.42 |
|  | pH5.5 | 1.01E+05 | 2.57E−02 | 129 | 600-50 nM | 3.95E+06 | 2.53E−07 | 253 |  |
| mAb2 | pH7.4 | 4.45E+04 | 4.60E−03 | 86.3 | 600-50 nM | 9.69E+06 | 1.03E−07 | 103 | 2.82 |
|  | pH5.5 | 9.66E+04 | 2.81E−02 | 124 | 600-50 nM | 3.44E+06 | 2.90E−07 | 290 |  |
| mAb3 | pH 7.4 | 3.34E+04 | 5.82E−03 | 90 | 600-50 nM | 5.75E+06 | 1.74E−07 | 174 | 1.86 |
|  | pH5.5 | 1.02E+05 | 3.30E−02 | 105 | 600-50 nM | 3.09E+06 | 3.23E−07 | 323 |  |
| mAb4 | pH 7.4 | 4.55E+04 | 5.65E−03 | 71.7 | 600-50 nM | 8.06E+06 | 1.24E−07 | 124 | 3.48 |
|  | pH5.5 | 8.31E+04 | 3.59E−02 | 117 | 600-50 nM | 2.32E+06 | 4.32E−07 | 432 |  |
| mAb5 | pH 7.4 | 3.51E+04 | 6.37E−03 | 75.3 | 600-50 nM | 5.51E+06 | 1.81E−07 | 181 | 2.25 |
|  | pH5.5 | 9.20E+04 | 3.76E−02 | 49.2 | 600-50 nM | 2.45E+06 | 4.08E−07 | 408 |  |
| mAb6 | pH 7.4 | 4.09E+04 | 6.72E−03 | 67.8 | 600-50 nM * | 6.08E+06 | 1.65E−07 | 165 | 5.22 |
|  | pH5.5 | 9.31E+04 | 8.02E−02 | 95.8 | 600-50 nM | 1.16E+06 | 8.61E−07 | 861 |  |
| mAb7 | pH 7.4 | 4.85E+04 | 1.20E−02 | 83.8 | 600-50 nM | 4.05E+06 | 2.47E−07 | 247 | 2.36 |
|  | pH5.5 | 1.11E+05 | 6.46E−02 | 36.0 | 600-50 nM | 1.71E+06 | 5.83E−07 | 583 |  |
| mAb8 | pH 7.4 | 3.21E+04 | 7.72E−03 | 62.4 | 600-50 nM | 4.15E+06 | 2.41E−07 | 241 | 1.00 |
|  | pH5.5 | 8.46E+04 | 2.05E−02 | 99 | 600-100 nM | 4.13E+06 | 2.42E−07 | 242 |  |
| mAb9 | pH 7.4 | 2.88E+04 | 6.69E−03 | 69.8 | 600-50 nM | 4.31E+06 | 2.32E−07 | 232 | 2.33 |
|  | pH5.5 | 8.63E+04 | 4.67E−02 | 96.4 | 600-50 nM | 1.85E+06 | 5.41E−07 | 541 |  |
| mAb10 | pH 7.4 | 3.19E+04 | 6.01E−03 | 64.1 | 600-50 nM ** | 5.30E+06 | 1.89E−07 | 189 | 1.77 |
|  | pH5.5 | 8.21E+04 | 2.74E−02 | 91.7 | 600-50 nM | 2.99E+06 | 3.34E−07 | 334 |  |
| mAb11 | pH 7.4 | 4.04E+04 | 5.23E−03 | 57.5 | 600-50 nM | 7.73E+06 | 1.29E−07 | 129 | 3.90 |
|  | pH5.5 | 8.05E+04 | 4.05E−02 | 82.6 | 600-50 nM | 1.99E+06 | 5.03E−07 | 503 |  |
| mAb12 | pH 7.4 | 2.04E+04 | 6.55E−03 | 90.8 | 600-50 nM ** | 3.12E+06 | 3.21E−07 | 321 | 1.07 |
|  | pH5.5 | 7.32E+04 | 2.51E−02 | 99 | 600-50 nM | 2.91E+06 | 3.43E−07 | 343 |  |
| mAb13 | pH 7.4 | 3.70E+04 | 3.70E−02 | 28.5 | 600-50 nM | 9.98E+05 | 1.00E−06 | 1000 |  |
|  | pH5.5 | n/a | n/a | n/a | 600 nM | n/a | n/a | n/a |  |
| mAb14 | pH 7.4 | 2.60E+04 | 4.58E−02 | 42.8 | 600-50 nM | 5.67E+05 | 1.76E−06 | 1760 | n/a |
|  | pH5.5 | n/a | n/a | n/a | 600 nM | n/a | n/a | n/a |  |
| mAb15 | pH 7.4 | 1.09E+05 | 3.78E−03 | 64.5 | 600-50 nM ** | 2.88E+07 | 3.47E−08 | 35 | 2.48 |
|  | pH5.5 | 1.34E+05 | 1.16E−02 | 122 | 600-50 nM | 1.16E+07 | 8.62E−08 | 86 |  |
| mAb16 | pH 7.4 | 7.81E+04 | 4.66E−02 | 70.5 | 600-100 nM | 1.68E+06 | 5.96E−07 | 596 | n/a |
|  | pH5.5 | n/a | n/a | n/a | 600 nM | n/a | n/a | n/a |  |
| mAb17 | pH 7.4 | 9.87E+04 | 6.16E−03 | 62.7 | 600-50 nM ** | 1.60E+07 | 6.24E−08 | 62 | 4.12 |
|  | pH5.5 | 8.45E+04 | 2.17E−02 | 118 | 600-50 nM | 3.89E+06 | 2.57E−07 | 257 |  |
| mAb18 | pH 7.4 | 1.06E+05 | 5.39E−02 | 38.4 | 600-50 nM | 1.97E+06 | 5.09E−07 | 509 | n/a |
|  | pH5.5 | n/a | n/a | n/a | 600 nM | n/a | n/a | n/a |  |

TABLE 17-continued

SPR analysis of ApoC3 binding to immobilized, humanized anti-ApoC3 antibodies

| Antibody | HBS-EP | ka (1/Ms) | kd (1/s) | Rmax (RU) | Conc of target | KA (1/M) | KD (M) | KD (nM) | KD (nM) pH5.5/pH7.4 |
|---|---|---|---|---|---|---|---|---|---|
| mAb19 | pH 7.4 | 1.30E+05 | 4.63E−03 | 70.3 | 600-50 nM | 2.82E+07 | 3.55E−08 | 36 | 4.42 |
|  | pH5.5 | 1.27E+05 | 1.98E−02 | 103 | 600-50 nM | 6.37E+06 | 1.57E−07 | 157 |  |
| mAb20 | pH 7.4 | 5.51E+04 | 7.37E−02 | 98.9 | 600-50 nM | 7.47E+05 | 1.34E−06 | 1340 | n/a |
|  | pH5.5 | n/a | n/a | n/a | 600 nM | n/a | n/a | n/a |  |

Sensorgrams were blank channel subtracted and double referenced to no-analyte blank assay
n/a not applicable
* with exception of the sensorgram of 400 nM
** with exception of the sensorgram of 200 nM As shown in FIGS. 4A-E, mAb1 to mAb6 showed improved apparent affinity to ApoC3 at pH7.4, and pH-dependent target binding was observed. The mAb7 antibody showed clear pH-dependent target binding, with high off-rate at both pH values. The Rmax value at pH 5.5 in the association phase was increased relative to 5E5VH5_VL8. The mAb8 to mAb12 antibodies demonstrated lower off-rates at pH 7.4 than 5E5VH5_VL8, higher Rmax levels at pH5.5 than at pH 7.4, higher off-rates at pH5.5 than that of 5E5VH5_VL8, and pH-dependent target binding. The mAb13 and mAb14 antibodies (generated by grafting the HCDR and LCDR sequences into the closest human germline framework sequences) showed loss of binding at both pH levels, and therefore, the affinity values at pH5.5 were not calculated. The mAb16, mAb18, and mAb20 antibodies showed clear pH-dependent target binding, due to the reduced affinity towards the target at pH 5.5, however, their off-rates at pH 7.4 were also increased.

In summary, the following binding profile groups were identified for the humanized antibodies according to the SPR assay results:

Group 1: mAbs 1, 2, 3, 4, 5, 6, 8, 9, 10, 11 and 12;
Group 2: mAbs 15, 17 and 19;
Group 3: mAbs 16, 18 and 20;
Group 4 contained mAb7; and
Group 5: mAbs 13 and 14.

Within each group, all variants showed similar SPR association and dissociation profile. Therefore, a representative antibody from each group was selected to assess their thermotolerance, as one of their developability parameter, based on the criteria of the highest human homology percentage.

5.3 Characterization of Thermotolerance of Selected Humanized Anti-ApoC3 Antibodies The thermotolerance of humanized antibodies was assessed after incubation at different temperatures in the range of 56 to 68° C. for 1 h. The activity of the antibodies was determined in an SPR assay in which 500 RU of native huApoC3 protein was immobilized on a CM5 chip (GE Healthcare, cat. nr. BR100012). The immobilization was performed in accordance with the method provided by Biacore using the NHS/EDC kit (Biacore AB): after activation of the chip, a solution of 60 µg/ml of human ApoC3 in 10 mM acetate buffer at pH 4.5 was prepared and injected until the surface density reached approximately 500 RU.

100 µL of test antibody at 10 nM diluted in HBS-EP buffer (GE, cat #BR-1008-26; 0.010 M HEPES, 0.150M NaCl, 3 mM EDTA, 0.05% (v/v) surfactant P20, pH 7.4) was injected and passed through the flow cells at a flow rate of 30 µl/min, followed by an off-rate wash with the HBS-EP buffer at pH7.4 for 10 min. After the dissociation, the flow cell surfaces were regenerated by injecting 10 µl of 10 mM NaOH/1 M NaCl and 10 µl of 10 mM glycine at pH1.5.

The association rate and the maximal RU value reached in the binding phase were measured as the readout parameter. The association rate (slope) was assessed in the initial binding phase up to 200 s and the RU maximal value (R0) was read at the beginning of the dissociation phase at 345 s. The percentage of functional antibodies was calculated based on the reference (sample incubated at 4° C.) set to 100%. The melting temperature of each antibody was determined as the inflection point at the activity vs temperature curves.

As shown in FIGS. 5A and 5B, and as listed in Table 18, most humanized antibodies tested showed significantly improved melting temperatures as compared to the parental clone 5E5VH5_VL8. However, mAb14 had a significant lower melting temperature than 5E5VH5_VL8.

TABLE 18

Melting temperatures of humanized anti-ApoC3 antibodies.

| Anti-ApoC3 antibody | Melting temperature, ° C. (EC50) |
|---|---|
| 5E5VH5_VL8 | 62.9 |
| mAb7 | 64.2 |
| mAb9 | 65.9 |
| mAb14 | 57.1 |
| mAb17 | 65.9 |
| mAb18 | 61.8 |

The thermotolerance of mAb13 was also assessed in the foregoing assay to determine if the observed thermotolerance change was related to the germline framework sequence that was used for the CDR grafting of variant 13 and 14. The assay was performed in an extended temperature range to cover the expected meting temperature of the humanized antibodies and of 5E5VH5_VL8 (assayed as control). As shown in FIG. 5C, mAb13 and mAb14 had similar thermotolerance curves, and exhibited melting temperatures of about 57° C., about 6° C. lower than that of 5E5VH5_VL8.

The invention is not to be limited in scope by the specific embodiments disclosed herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed is:

1. An isolated polynucleotide encoding a heavy chain variable region and/or a light chain variable region of an antibody that specifically binds to ApoC3, the antibody comprising a heavy chain variable region comprising complementarity determining regions CDRH1, CDRH2 and CDRH3, and a light chain variable region comprising complementarity determining regions CDRL1, CDRL2 and CDRL3, wherein:
    (a) CDRH1 comprises the amino acid sequence of TYSMR (SEQ ID NO: 3);
    (b) CDRH2 comprises the amino acid sequence of SIHTX$_1$X$_2$GGTAYRDSVKG, wherein X$_1$ is G, E, or D, and X$_2$ is G or A (SEQ ID NO: 87);
    (c) CDRH3 comprises the amino acid sequence of AGYSD (SEQ ID NO: 10);
    (d) CDRL1 comprises the amino acid sequence of KTSQGLVHSXGKTYFY, wherein X is D or G (SEQ ID NO: 88);
    (e) CDRL2 comprises the amino acid sequence of QVSNRAS (SEQ ID NO: 7); and
    (f) CDRL3 comprises the amino acid sequence of AXGTYYPHT, wherein X is Q or H (SEQ ID NO: 8), and
wherein the CDRH1, CDRH2, and CDRH3 of the antibody are not SEQ ID NOs: 3, 11, and 10, respectively.

2. The isolated polynucleotide of claim 1, wherein:
    (a) the CDRH2 comprises the amino acid sequence of SIHTGGGGTAYRDSVKG (SEQ ID NO: 36), SIHTEAGGTAYRDSVKG (SEQ ID NO: 37), SIHTDAGGTAYRDSVKG (SEQ ID NO: 38), or SIHTEGGGTAYRDSVKG (SEQ ID NO: 39);
    (b) the CDRL1 comprises the amino acid sequence of KTSQGLVHSDGKTYFY (SEQ ID NO: 6) or KTSQGLVHSGGKTYFY (SEQ ID NO: 40); and/or
    (c) the CDRL3 comprises the amino acid sequence of AHGTYYPHT (SEQ ID NO: 14) or AQGTYYPHT (SEQ ID NO: 13).

3. The isolated polynucleotide of claim 1, wherein the CDRH1, CDRH2, CDRH3, CDRL1, CDRL2, and CDRL3 comprise the amino acid sequences set forth in SEQ ID NOs: 3, 36, 10, 6, 7, and 14; 3, 37, 10, 40, 7, and 14; 3, 38, 10, 40, 7, and 14; 3, 38, 10, 6, 7, and 14; 3, 39, 10, 6, 7, and 14; or 3, 37, 10, 40, 7, and 13, respectively.

4. The isolated polynucleotide of claim 1, wherein the antibody is a humanized antibody.

5. The isolated polynucleotide of claim 1, wherein the polynucleotide encodes a human constant region, optionally wherein:
    (a) the constant region is a variant of a wild type human immunoglobulin heavy chain constant region, and wherein the variant human immunoglobulin heavy chain constant region has an increased affinity for human neonatal Fc receptor (FcRn) at pH 6 relative to the affinity of the corresponding wild type human immunoglobulin heavy chain constant region for human FcRn at pH 6;
    (b) the constant region is a human IgG, optionally a human IgG$_1$, IgG$_2$, or IgG$_4$;
    (c) the constant region comprises the amino acids K, F, and Y at EU positions 433, 434, and 436, respectively;
    (d) the constant region comprises the amino acids Y, T, and E at EU positions 252, 254, and 256, respectively;
    (e) the constant region comprises the amino acids L and S at EU positions 428 and 434, respectively; or
    (f) the constant region comprises an amino acid sequence selected from the group consisting of SEQ ID NOs: 22-24, 76-78, and 81-86.

6. The isolated polynucleotide of claim 1, wherein the ApoC3 is human ApoC3.

7. A pharmaceutical composition comprising the polynucleotide of claim 1 and a pharmaceutically acceptable carrier.

8. An expression vector comprising the polynucleotide of claim 1.

9. A host cell comprising the polynucleotide of claim 1.

10. An isolated polynucleotide encoding a heavy chain variable region comprising an amino acid sequence selected from the group consisting of SEQ ID NOs: 42-53.

11. The isolated polynucleotide of claim 10, wherein the polynucleotide encodes a heavy chain variable region and a light chain variable region, and wherein the heavy chain variable region and the light chain variable region, respectively, comprise the amino acid sequences set forth in SEQ ID NOs: 42 and 54, 43 and 55, 44 and 56, 45 and 57, 46 and 58, 46 and 54, 47 and 58, 47 and 54, 48 and 58, 48 and 54, 49 and 59, 49 and 60, 50 and 59, 50 and 60, 51 and 61, 52 and 62, 53 and 62, 43 and 63, 44 and 64, or 45 and 65.

12. The isolated polynucleotide of claim 11, wherein the polynucleotide encodes a heavy chain and a light chain, wherein the heavy chain and the light chain, respectively, comprise the amino acid sequences set forth in SEQ ID NOs: 66 and 74, 67 and 74, 68 and 74, 69 and 74, 70 and 74, 71 and 74, 72 and 74, or 73 and 74, respectively.

13. The isolated polynucleotide of claim 10, wherein the polynucleotide encodes an amino acid sequence selected from the group consisting of SEQ ID NOs: 66-73.

14. An isolated polynucleotide encoding a light chain variable region comprising an amino acid sequence selected from the group consisting of SEQ ID NOs: 54-65.

15. The isolated polynucleotide of claim 14, wherein the polynucleotide encodes the amino acid sequence set forth in SEQ ID NO: 74.

* * * * *

SEQUENCE LISTING

```
<160> NUMBER OF SEQ ID NOS: 93

<210> SEQ ID NO 1
<211> LENGTH: 79
<212> TYPE: PRT
<213> ORGANISM: Homo sapiens

<400> SEQUENCE: 1

Ser Glu Ala Glu Asp Ala Ser Leu Leu Ser Phe Met Gln Gly Tyr Met
1               5                   10                  15

Lys His Ala Thr Lys Thr Ala Lys Asp Ala Leu Ser Ser Val Gln Glu
            20                  25                  30

Ser Gln Val Ala Gln Gln Ala Arg Gly Trp Val Thr Asp Gly Phe Ser
        35                  40                  45

Ser Leu Lys Asp Tyr Trp Ser Thr Val Lys Asp Lys Phe Ser Glu Phe
    50                  55                  60

Trp Asp Leu Asp Pro Glu Val Arg Pro Thr Ser Ala Val Ala Ala
65                  70                  75

<210> SEQ ID NO 2
<211> LENGTH: 10
<212> TYPE: PRT
<213> ORGANISM: Homo sapiens

<400> SEQUENCE: 2

Phe Ser Glu Phe Trp Asp Leu Asp Pro Glu
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Tyr Ser Met Arg
1               5

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or H

<400> SEQUENCE: 4

Ser Ile Xaa Thr Asp Gly Gly Thr Ala Tyr Arg Asp Ser Val Lys
1               5                   10                  15

Gly

<210> SEQ ID NO 5
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A or H

<400> SEQUENCE: 5

Xaa Gly Tyr Ser Asp
1               5

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Thr Ser Gln Gly Leu Val His Ser Asp Gly Lys Thr Tyr Phe Tyr
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Val Ser Asn Arg Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Q or H

<400> SEQUENCE: 8

Ala Xaa Gly Thr Tyr Tyr Pro His Thr
1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ile Ser Thr Asp Gly Gly Gly Thr Ala Tyr Arg Asp Ser Val Lys
1               5                   10                  15

Gly

<210> SEQ ID NO 10
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Gly Tyr Ser Asp
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Ile His Thr Asp Gly Gly Thr Ala Tyr Arg Asp Ser Val Lys
1               5                   10                  15

Gly

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Gly Tyr Ser Asp
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Gln Gly Thr Tyr Tyr Pro His Thr
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala His Gly Thr Tyr Tyr Pro His Thr
1               5

<210> SEQ ID NO 15
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 15

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile Ser Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
                85                  90                  95

Val Ile Ala Gly Tyr Ser Asp Trp Gly Gln Gly Thr Gln Val Thr Val
            100                 105                 110

Ser Ser

<210> SEQ ID NO 16
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile His Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
                85                  90                  95

Val Ile Ala Gly Tyr Ser Asp Trp Gly Gln Gly Thr Gln Val Thr Val
            100                 105                 110

Ser Ser

<210> SEQ ID NO 17
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45
```

```
Ser Ser Ile Ser Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Asn Leu Lys Pro Glu Asp Thr Ala Ile Tyr Tyr Cys
                 85                  90                  95

Val Ile His Gly Tyr Ser Asp Trp Gly Gln Gly Thr Gln Val Thr Val
            100                 105                 110

Ser Ser

<210> SEQ ID NO 18
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Leu Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile His Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
 65                  70                  75                  80

Leu Gln Met Asn Asn Leu Lys Pro Glu Asp Thr Ala Ile Tyr Tyr Cys
                 85                  90                  95

Val Ile His Gly Tyr Ser Asp Trp Gly Gln Gly Thr Gln Val Thr Val
            100                 105                 110

Ser Ser

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Thr Met Leu Thr Gln Ser Pro Gly Ser Leu Ser Val Val Pro Gly
 1               5                  10                  15

Glu Ser Ala Ser Ile Ser Cys Lys Thr Ser Gln Gly Leu Val His Ser
            20                  25                  30

Asp Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
    50                  55                  60

Asp Arg Phe Thr Gly Ser Gly Ser Gly Thr Asp Phe Thr Leu Lys Ile
 65                  70                  75                  80

Ser Gly Val Lys Ala Glu Asp Ala Gly Val Tyr Tyr Cys Ala Gln Gly
                 85                  90                  95

Thr Tyr Tyr Pro His Thr Phe Gly Ser Gly Thr Arg Leu Glu Ile Lys
            100                 105                 110
```

<210> SEQ ID NO 20
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Thr Met Leu Thr Gln Ser Pro Gly Ser Leu Ser Val Val Pro Gly
1               5                   10                  15

Glu Ser Ala Ser Ile Ser Cys Lys Thr Ser Gln Gly Leu Val His Ser
            20                  25                  30

Asp Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala His Gly
                85                  90                  95

Thr Tyr Tyr Pro His Thr Phe Gly Ser Gly Thr Arg Leu Glu Ile Lys
            100                 105                 110

<210> SEQ ID NO 21
<211> LENGTH: 330
<212> TYPE: PRT
<213> ORGANISM: Homo sapiens

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 22
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu

```
            225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu Lys Phe His Tyr Thr
305                 310                 315                 320

Gln Lys Ser Leu Ser Leu Ser Pro Gly Lys
            325                 330

<210> SEQ ID NO 24
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
            325                 330

<210> SEQ ID NO 25
<211> LENGTH: 107
<212> TYPE: PRT
<213> ORGANISM: Homo sapiens

<400> SEQUENCE: 25

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 26
<211> LENGTH: 106
<212> TYPE: PRT
<213> ORGANISM: Homo sapiens

<400> SEQUENCE: 26

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 27
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
            35                  40                  45

Ser Ser Ile His Thr Asp Gly Gly Thr Ala Tyr Arg Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
            85                  90                  95

Val Ile Ala Gly Tyr Ser Asp Trp Gly Gln Gly Thr Gln Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
            165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His

```
                    420                 425                 430
Tyr Thr Gln Lys Ser Leu Ser Leu Ser Pro Gly Lys
            435                 440

<210> SEQ ID NO 28
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile His Thr Asp Gly Gly Thr Ala Tyr Arg Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
                85                  90                  95

Val Ile Ala Gly Tyr Ser Asp Trp Gly Gln Gly Thr Gln Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Tyr Ile Thr Arg Glu Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335
```

```
Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
            435                 440
```

<210> SEQ ID NO 29
<211> LENGTH: 444
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile His Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
                85                  90                  95

Val Ile Ala Gly Tyr Ser Asp Trp Gly Gln Gly Thr Gln Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255
```

-continued

```
Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu Lys Phe His
            420                 425                 430

Tyr Thr Gln Lys Ser Leu Ser Leu Ser Pro Gly Lys
            435                 440

<210> SEQ ID NO 30
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
            35                  40                  45

Ser Ser Ile His Thr Asp Gly Gly Thr Ala Tyr Arg Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
            85                  90                  95

Val Ile Ala Gly Tyr Ser Asp Trp Gly Gln Gly Thr Gln Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
            130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
```

```
                   165                 170                 175
Tyr Ser Leu Ser Ser Val Val Thr Val Pro Ser Ser Leu Gly Thr
                180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Thr Cys Pro
        210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
                260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Leu His Glu Ala Leu His Ser His
            420                 425                 430

Tyr Thr Gln Lys Ser Leu Ser Leu Ser Pro Gly Lys
        435                 440

<210> SEQ ID NO 31
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile Ser Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
65                  70                  75                  80
```

Leu Gln Met Asn Asn Leu Lys Pro Glu Asp Thr Ala Ile Tyr Tyr Cys
                 85                  90                  95

Val Ile His Gly Tyr Ser Asp Trp Gly Gln Gly Thr Gln Val Thr Val
            100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
        130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 32
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile Ser Thr Asp Gly Gly Thr Ala Tyr Arg Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
                85                  90                  95

Val Ile His Gly Tyr Ser Asp Trp Gly Gln Gly Thr Gln Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Tyr Ile Thr Arg Glu Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415
```

```
Gly Asn Val Phe Ser Cys Ser Val Met His Glu Ala Leu His Asn His
                420                 425                 430

Tyr Thr Gln Lys Ser Leu Ser Leu Ser Pro Gly Lys
        435                 440

<210> SEQ ID NO 33
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile Ser Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
                85                  90                  95

Val Ile His Gly Tyr Ser Asp Trp Gly Gln Gly Thr Gln Val Thr Val
                100                 105                 110

Ser Ser Ala Ser Thr Lys Gly Pro Ser Val Phe Pro Leu Ala Pro Ser
            115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335
```

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu Lys Phe His
            420                 425                 430

Tyr Thr Gln Lys Ser Leu Ser Leu Ser Pro Gly Lys
            435                 440

<210> SEQ ID NO 34
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Thr Tyr
            20                  25                  30

Ser Met Arg Trp Val Arg Gln Val Pro Arg Lys Ala Leu Glu Trp Val
        35                  40                  45

Ser Ser Ile Ser Thr Asp Gly Gly Thr Ala Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Asn Leu Lys Pro Glu Asp Thr Ala Ile Tyr Tyr Cys
                85                  90                  95

Val Ile His Gly Tyr Ser Asp Trp Gly Gln Gly Thr Gln Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val

```
            245                 250                 255
Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
            275                 280                 285

Arg Glu Glu Gln Tyr Asn Ser Thr Tyr Arg Val Val Ser Val Leu Thr
            290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
            325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Leu His Glu Ala Leu His Ser His
            420                 425                 430

Tyr Thr Gln Lys Ser Leu Ser Leu Ser Pro Gly Lys
            435                 440

<210> SEQ ID NO 35
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Thr Met Leu Thr Gln Ser Pro Gly Ser Leu Ser Val Val Pro Gly
1               5                   10                  15

Glu Ser Ala Ser Ile Ser Cys Lys Thr Ser Gln Gly Leu Val His Ser
            20                  25                  30

Asp Gly Lys Thr Tyr Phe Tyr Trp Phe Leu Gln Lys Pro Gly Gln Ser
            35                  40                  45

Pro Gln Gln Leu Ile Tyr Gln Val Ser Asn Arg Ala Ser Gly Val Pro
        50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala His Gly
            85                  90                  95

Thr Tyr Tyr Pro His Thr Phe Gly Ser Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Ile His Thr Gly Gly Gly Thr Ala Tyr Arg Asp Ser Val Lys
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Ile His Thr Glu Ala Gly Gly Thr Ala Tyr Arg Asp Ser Val Lys
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ile His Thr Asp Ala Gly Gly Thr Ala Tyr Arg Asp Ser Val Lys
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Ile His Thr Glu Gly Gly Gly Thr Ala Tyr Arg Asp Ser Val Lys
1               5                   10                  15

Gly

<210> SEQ ID NO 40
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Thr Ser Gln Gly Leu Val His Ser Gly Gly Lys Thr Tyr Phe Tyr
1               5                   10                  15

<210> SEQ ID NO 41

<400> SEQUENCE: 41

000

<210> SEQ ID NO 42
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
        35                  40                  45

Ile His Thr Gly Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Ile Tyr Tyr Cys Val Ile
                85                  90                  95

Ala Gly Tyr Ser Asp Trp Gly Gln Gly Thr Leu Val Thr Val Ser Ser
            100                 105                 110

<210> SEQ ID NO 43
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Gly Thr Tyr Ser Met
            20                  25                  30

Arg Trp Val Arg Gln Ala Pro Gly Lys Gly Leu Glu Trp Val Ser Ser
        35                  40                  45

Ile His Thr Glu Ala Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Lys Ala Glu Asp Thr Ala Ile Tyr Tyr Cys Val Ile
                85                  90                  95
```

```
Ala Gly Tyr Ser Asp Trp Gly Gln Gly Thr Gln Val Thr Val Ser Ser
            100                 105                 110
```

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
            35                  40                  45

Ile His Thr Glu Ala Gly Gly Thr Ala Tyr Arg Asp Ser Val Lys Gly
        50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Val Tyr Tyr Cys Val Ile
                85                  90                  95

Ala Gly Tyr Ser Asp Trp Gly Gln Gly Thr Leu Val Thr Val Ser Ser
            100                 105                 110
```

<210> SEQ ID NO 45
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
            35                  40                  45

Ile His Thr Asp Ala Gly Gly Thr Ala Tyr Arg Asp Ser Val Lys Gly
        50                  55                  60

Arg Phe Thr Ile Ser Arg Asp Asn Ala Lys Asn Thr Leu Tyr Leu Gln
65                  70                  75                  80

Met Asn Asn Leu Arg Pro Glu Asp Thr Ala Val Tyr Tyr Cys Val Ile
                85                  90                  95

Ala Gly Tyr Ser Asp Trp Gly Gln Gly Thr Leu Val Thr Val Ser Ser
            100                 105                 110
```

<210> SEQ ID NO 46
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gln Leu Val Glu Ser Gly Gly Gly Leu Val Gln Pro Gly Gly Ser Leu
```

```
              1               5                  10                 15
Arg Leu Ser Cys Ala Ala Ser Gly Phe Thr Phe Gly Thr Tyr Ser Met
                  20                 25                 30
Arg Trp Val Arg Gln Val Pro Gly Lys Gly Leu Glu Trp Val Ser Ser
              35                 40                 45
Ile His Thr Glu Gly Gly Gly Thr Ala Tyr Arg Asp Ser Val Lys Gly
          50                 55                 60
Arg Phe Thr Ile Ser Arg Asp Asn Ala Lys Asn Thr Leu Tyr Leu Gln
65                 70                 75                 80
Met Asn Ser Leu Arg Ala Glu Asp Thr Ala Ile Tyr Tyr Cys Val Ile
                  85                 90                 95
Ala Gly Tyr Ser Asp Trp Gly Gln Gly Thr Leu Val Thr Val Ser Ser
                  100                105                110

<210> SEQ ID NO 47
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Leu Val Glu Ser Gly Gly Gly Leu Val Gln Pro Gly Gly Ser Leu
1               5                  10                 15
Arg Leu Ser Cys Ala Ala Ser Gly Phe Thr Phe Gly Thr Tyr Ser Met
                  20                 25                 30
Arg Trp Val Arg Gln Ala Pro Gly Lys Gly Leu Glu Trp Val Ser Ser
              35                 40                 45
Ile His Thr Glu Gly Gly Gly Thr Ala Tyr Arg Asp Ser Val Lys Gly
          50                 55                 60
Arg Phe Thr Ile Ser Arg Asp Asn Ala Lys Asn Thr Leu Tyr Leu Gln
65                 70                 75                 80
Met Asn Ser Leu Arg Ala Glu Asp Thr Ala Ile Tyr Tyr Cys Val Ile
                  85                 90                 95
Ala Gly Tyr Ser Asp Trp Gly Gln Gly Thr Leu Val Thr Val Ser Ser
                  100                105                110

<210> SEQ ID NO 48
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Leu Val Glu Ser Gly Gly Gly Leu Val Gln Pro Gly Gly Ser Leu
1               5                  10                 15
Arg Leu Ser Cys Ala Ala Ser Gly Phe Thr Phe Gly Thr Tyr Ser Met
                  20                 25                 30
Arg Trp Val Arg Gln Ala Pro Gly Lys Gly Leu Glu Trp Val Ser Ser
              35                 40                 45
Ile His Thr Glu Gly Gly Gly Thr Ala Tyr Arg Asp Ser Val Lys Gly
          50                 55                 60
Arg Phe Thr Ile Ser Arg Asp Asn Ala Lys Asn Thr Leu Tyr Leu Gln
65                 70                 75                 80
Met Asn Ser Leu Arg Ala Glu Asp Thr Ala Val Tyr Tyr Cys Val Ile
```

```
                    85                  90                  95

Ala Gly Tyr Ser Asp Trp Gly Gln Gly Thr Leu Val Thr Val Ser Ser
                100                 105                 110

<210> SEQ ID NO 49
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
        35                  40                  45

Ile His Thr Asp Ala Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Val Tyr Tyr Cys Val Ile
                85                  90                  95

Ala Gly Tyr Ser Asp Trp Gly Gln Gly Thr Leu Val Thr Val Ser Ser
                100                 105                 110

<210> SEQ ID NO 50
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Val Pro Gly Lys Gly Leu Glu Trp Val Ser Ser
        35                  40                  45

Ile His Thr Glu Gly Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Val Tyr Tyr Cys Val Ile
                85                  90                  95

Ala Gly Tyr Ser Asp Trp Gly Gln Gly Thr Leu Val Thr Val Ser Ser
                100                 105                 110

<210> SEQ ID NO 51
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51
```

```
Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Val Pro Gly Lys Gly Leu Glu Trp Val Ser Ser
        35                  40                  45

Ile His Thr Asp Ala Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Ser Leu Arg Pro Glu Asp Thr Ala Ile Tyr Tyr Cys Val Ile
                85                  90                  95

Ala Gly Tyr Ser Asp Trp Gly Gln Gly Thr Leu Val Thr Val Ser Ser
            100                 105                 110
```

<210> SEQ ID NO 52
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Val Pro Gly Lys Gly Leu Glu Trp Val Ser Ser
        35                  40                  45

Ile His Thr Glu Gly Gly Gly Thr Ala Tyr Arg Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Val Ile
                85                  90                  95

Ala Gly Tyr Ser Asp Trp Gly Gln Gly Thr Leu Val Thr Val Ser Ser
            100                 105                 110
```

<210> SEQ ID NO 53
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Gln Leu Leu Glu Ser Gly Gly Gly Leu Val Gln Pro Gly Gly Ser Leu
1               5                   10                  15

Arg Leu Ser Cys Ala Ala Ser Gly Phe Thr Phe Gly Thr Tyr Ser Met
            20                  25                  30

Arg Trp Val Arg Gln Val Pro Gly Lys Gly Leu Glu Trp Val Ser Ser
        35                  40                  45

Ile His Thr Glu Gly Gly Gly Thr Ala Tyr Arg Asp Ser Val Lys Gly
    50                  55                  60

Arg Phe Thr Ile Ser Arg Asp Asn Ser Lys Asn Thr Leu Tyr Leu Gln
65                  70                  75                  80
```

```
Met Asn Ser Leu Arg Ala Glu Asp Thr Ala Val Tyr Cys Val Ile
                85                  90                  95

Ala Gly Tyr Ser Asp Trp Gly Gln Gly Thr Leu Val Thr Val Ser Ser
            100                 105                 110

<210> SEQ ID NO 54
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Met Thr Gln Ser Pro Leu Ser Leu Pro Val Thr Pro Gly
1               5                   10                  15

Glu Ser Ala Ser Ile Ser Cys Lys Thr Ser Gln Gly Leu Val His Ser
            20                  25                  30

Asp Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Lys Ala Glu Asp Ala Gly Val Tyr Tyr Cys Ala His Gly
                85                  90                  95

Thr Tyr Tyr Pro His Thr Phe Gly Gln Gly Thr Arg Leu Glu Ile Lys
            100                 105                 110

<210> SEQ ID NO 55
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Val Met Thr Gln Ser Pro Leu Ser Leu Pro Val Thr Pro Gly
1               5                   10                  15

Glu Ser Ala Ser Ile Ser Cys Lys Thr Ser Gln Gly Leu Val His Ser
            20                  25                  30

Gly Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
50                  55                  60

Asp Arg Phe Thr Gly Ser Gly Ser Gly Thr Asp Phe Thr Leu Lys Ile
65                  70                  75                  80

Ser Arg Val Glu Ala Glu Asp Ala Gly Val Tyr Tyr Cys Ala His Gly
                85                  90                  95

Thr Tyr Tyr Pro His Thr Phe Gly Ser Gly Thr Arg Leu Glu Ile Lys
            100                 105                 110

<210> SEQ ID NO 56
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 56

Asp Ile Val Met Thr Gln Ser Pro Leu Ser Leu Pro Val Thr Pro Gly
1               5                   10                  15

Glu Pro Ala Ser Ile Ser Cys Lys Thr Ser Gln Gly Leu Val His Ser
            20                  25                  30

Gly Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Ala Gly Val Tyr Tyr Cys Ala His Gly
                85                  90                  95

Thr Tyr Tyr Pro His Thr Phe Gly Gln Gly Thr Arg Leu Glu Ile Lys
                100                 105                 110

<210> SEQ ID NO 57
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Val Met Thr Gln Ser Pro Gly Ser Leu Ser Val Thr Pro Gly
1               5                   10                  15

Glu Pro Ala Ser Ile Ser Cys Lys Thr Ser Gln Gly Leu Val His Ser
            20                  25                  30

Gly Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Glu Ala Glu Asp Ala Gly Val Tyr Tyr Cys Ala His Gly
                85                  90                  95

Thr Tyr Tyr Pro His Thr Phe Gly Gln Gly Thr Arg Leu Glu Ile Lys
                100                 105                 110

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Thr Gln Ser Pro Leu Ser Leu Pro Val Thr Pro Gly
1               5                   10                  15

Glu Ser Ala Ser Ile Ser Cys Lys Thr Ser Gln Gly Leu Val His Ser
            20                  25                  30

Asp Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
    50                  55                  60

-continued

Asp Arg Phe Thr Gly Ser Gly Ser Gly Thr Asp Phe Thr Leu Lys Ile
65                  70                  75                  80

Ser Arg Val Lys Ala Glu Asp Ala Gly Val Tyr Tyr Cys Ala His Gly
                85                  90                  95

Thr Tyr Tyr Pro His Thr Phe Gly Gln Gly Thr Arg Leu Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Val Met Thr Gln Ser Pro Leu Ser Leu Ser Val Val Pro Gly
1               5                   10                  15

Glu Pro Ala Ser Ile Ser Cys Lys Thr Ser Gln Gly Leu Val His Ser
                20                  25                  30

Asp Gly Lys Thr Tyr Phe Tyr Trp Phe Leu Gln Lys Pro Gly Gln Ser
            35                  40                  45

Pro Gln Gln Leu Ile Tyr Gln Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Gly
                85                  90                  95

Thr Tyr Tyr Pro His Thr Phe Gly Gln Gly Thr Arg Leu Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Val Met Thr Gln Ser Pro Leu Ser Leu Ser Val Thr Pro Gly
1               5                   10                  15

Glu Pro Ala Ser Ile Ser Cys Lys Thr Ser Gln Gly Leu Val His Ser
                20                  25                  30

Asp Gly Lys Thr Tyr Phe Tyr Trp Phe Leu Gln Lys Pro Gly Gln Ser
            35                  40                  45

Pro Gln Gln Leu Ile Tyr Gln Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Gly
                85                  90                  95

Thr Tyr Tyr Pro His Thr Phe Gly Gln Gly Thr Arg Leu Glu Ile Lys
            100                 105                 110

<210> SEQ ID NO 61
<211> LENGTH: 112
<212> TYPE: PRT
<213> ORGANISM: Artificial Sequence
<220> FEATURE:

<223> OTHER INFORMATION: Description of Artificial Sequence: Synthetic
     polypeptide

<400> SEQUENCE: 61

Asp Ile Val Met Thr Gln Ser Pro Leu Ser Leu Ser Val Thr Pro Gly
1               5                   10                  15

Glu Pro Ala Ser Ile Ser Cys Lys Thr Ser Gln Gly Leu Val His Ser
            20                  25                  30

Asp Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Lys Ala Glu Asp Val Gly Val Tyr Tyr Cys Ala His Gly
                85                  90                  95

Thr Tyr Tyr Pro His Thr Phe Gly Gln Gly Thr Arg Leu Glu Ile Lys
            100                 105                 110

<210> SEQ ID NO 62
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Lys Thr Ser Gln Gly Leu Val His Ser
            20                  25                  30

Asp Gly Lys Thr Tyr Phe Tyr Trp Tyr Leu Gln Lys Pro Gly Gln Ser
        35                  40                  45

Pro Gln Leu Leu Ile Tyr Gln Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Gly
                85                  90                  95

Thr Tyr Tyr Pro His Thr Phe Gly Gln Gly Thr Arg Leu Glu Ile Lys
            100                 105                 110

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 63

Asp Ile Val Met Thr Gln Ser Pro Leu Ser Leu Pro Val Thr Pro Gly
1               5                   10                  15

Glu Ser Ala Ser Ile Ser Cys Lys Thr Ser Gln Gly Leu Val His Ser
            20                  25                  30

Gly Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro

```
                50                  55                  60
Asp Arg Phe Thr Gly Ser Gly Ser Gly Thr Asp Phe Thr Leu Lys Ile
 65                  70                  75                  80

Ser Arg Val Glu Ala Glu Asp Ala Gly Val Tyr Tyr Cys Ala Gln Gly
                 85                  90                  95

Thr Tyr Tyr Pro His Thr Phe Gly Ser Gly Thr Arg Leu Glu Ile Lys
                100                 105                 110

<210> SEQ ID NO 64
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Val Met Thr Gln Ser Pro Leu Ser Leu Pro Val Thr Pro Gly
 1               5                  10                  15

Glu Pro Ala Ser Ile Ser Cys Lys Thr Ser Gln Gly Leu Val His Ser
                 20                  25                  30

Gly Gly Lys Thr Tyr Phe Tyr Trp Phe Leu Gln Lys Pro Gly Gln Ser
             35                  40                  45

Pro Gln Gln Leu Ile Tyr Gln Val Ser Asn Arg Ala Ser Gly Val Pro
         50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Ala Gly Val Tyr Tyr Cys Ala Gln Gly
                 85                  90                  95

Thr Tyr Tyr Pro His Thr Phe Gly Gln Gly Thr Arg Leu Glu Ile Lys
                100                 105                 110

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ile Val Met Thr Gln Ser Pro Gly Ser Leu Ser Val Thr Pro Gly
 1               5                  10                  15

Glu Pro Ala Ser Ile Ser Cys Lys Thr Ser Gln Gly Leu Val His Ser
                 20                  25                  30

Gly Gly Lys Thr Tyr Phe Tyr Trp Phe Leu Gln Lys Pro Gly Gln Ser
             35                  40                  45

Pro Gln Gln Leu Ile Tyr Gln Val Ser Asn Arg Ala Ser Gly Val Pro
         50                  55                  60

Asp Arg Phe Thr Gly Ser Gly Ser Gly Thr Asp Phe Thr Leu Lys Ile
 65                  70                  75                  80

Ser Gly Val Glu Ala Glu Asp Ala Gly Val Tyr Tyr Cys Ala Gln Gly
                 85                  90                  95

Thr Tyr Tyr Pro His Thr Phe Gly Gln Gly Thr Arg Leu Glu Ile Lys
                100                 105                 110

<210> SEQ ID NO 66
<211> LENGTH: 441
<212> TYPE: PRT
```

-continued

<213> ORGANISM: Artificial Sequence
<220> FEATURE:
<223> OTHER INFORMATION: Description of Artificial Sequence: Synthetic
      polypeptide

<400> SEQUENCE: 66

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
        35                  40                  45

Ile His Thr Gly Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Ile Tyr Tyr Cys Val Ile
                85                  90                  95

Ala Gly Tyr Ser Asp Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

```
Asn Tyr Lys Thr Thr Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 67
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
        35                  40                  45

Ile His Thr Gly Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Ile Tyr Tyr Cys Val Ile
                85                  90                  95

Ala Gly Tyr Ser Asp Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300
```

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
            325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Leu His Glu Ala Leu His Ser His Tyr Thr
            420                 425                 430

Gln Lys Ser Leu Ser Leu Ser Pro Gly
            435                 440

<210> SEQ ID NO 68
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
        35                  40                  45

Ile His Thr Gly Gly Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Ile Tyr Tyr Cys Val Ile
                85                  90                  95

Ala Gly Tyr Ser Asp Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys

```
                    210                 215                 220
Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu Lys Phe His Tyr Thr
            420                 425                 430

Gln Lys Ser Leu Ser Leu Ser Pro Gly
        435                 440

<210> SEQ ID NO 69
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
                20                  25                  30

Arg Trp Val Arg Gln Ala Pro Gly Lys Gly Leu Glu Trp Val Ser Ser
            35                  40                  45

Ile His Thr Gly Gly Gly Thr Ala Tyr Arg Asp Ser Val Lys Gly
        50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Ile Tyr Tyr Cys Val Ile
                85                  90                  95

Ala Gly Tyr Ser Asp Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125
```

-continued

Ser Thr Ser Gly Gly Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Tyr Ile Thr Arg Glu Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly
        435                 440

<210> SEQ ID NO 70
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
        35                  40                  45

```
Ile His Thr Gly Gly Gly Thr Ala Tyr Arg Asp Ser Val Lys Gly
 50                  55                  60

Arg Phe Thr Ile Ser Arg Asp Asn Ala Lys Asn Thr Leu Tyr Leu Gln
 65                  70                  75                  80

Met Asn Asn Leu Arg Ala Glu Asp Thr Ala Ile Tyr Tyr Cys Val Ile
                 85                  90                  95

Ala Gly Tyr Ser Asp Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
    290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Met Thr Lys
            340                 345                 350

Asn Gln Val Ser Leu Thr Cys Leu Val Lys Gly Phe Tyr Pro Ser Asp
        355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu His Asn His Tyr Thr Gln Lys Ser
            420                 425                 430

Leu Ser Leu Ser Leu Gly
        435

<210> SEQ ID NO 71
<211> LENGTH: 438
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
                20                  25                  30

Arg Trp Val Arg Gln Ala Pro Gly Lys Gly Leu Glu Trp Val Ser Ser
                35                  40                  45

Ile His Thr Gly Gly Gly Thr Ala Tyr Arg Asp Ser Val Lys Gly
            50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Ile Tyr Tyr Cys Val Ile
                85                  90                  95

Ala Gly Tyr Ser Asp Trp Gly Gln Gly Thr Leu Val Thr Val Ser Ser
                100                 105                 110

Ala Ser Thr Lys Gly Pro Ser Val Phe Pro Leu Ala Pro Cys Ser Arg
                115                 120                 125

Ser Thr Ser Glu Ser Thr Ala Ala Leu Gly Cys Leu Val Lys Asp Tyr
                130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
                180                 185                 190

Tyr Thr Cys Asn Val Asp His Lys Pro Ser Asn Thr Lys Val Asp Lys
                195                 200                 205

Arg Val Glu Ser Lys Tyr Gly Pro Pro Cys Pro Pro Cys Pro Ala Pro
                210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
                260                 265                 270

Gly Val Glu Val His Asn Ala Lys Thr Lys Pro Arg Glu Glu Gln Phe
                275                 280                 285

Asn Ser Thr Tyr Arg Val Val Ser Val Leu Thr Val Leu His Gln Asp
                290                 295                 300

Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
                340                 345                 350

Asn Gln Val Ser Leu Thr Cys Leu Val Lys Gly Phe Tyr Pro Ser Asp
                355                 360                 365

Ile Ala Val Glu Trp Glu Ser Asn Gly Gln Pro Glu Asn Asn Tyr Lys
                370                 375                 380
```

-continued

```
Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
            405                 410                 415

Cys Ser Val Leu His Glu Ala Leu His Ser His Tyr Thr Gln Lys Ser
            420                 425                 430

Leu Ser Leu Ser Leu Gly
            435

<210> SEQ ID NO 72
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
        35                  40                  45

Ile His Thr Gly Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Ile Tyr Tyr Cys Val Ile
                85                  90                  95

Ala Gly Tyr Ser Asp Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205

Arg Val Glu Ser Lys Tyr Gly Pro Pro Cys Pro Pro Cys Pro Ala Pro
    210                 215                 220

Glu Phe Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Glu Asp Pro Glu Val Gln Phe Asn Trp Tyr Val Asp
            260                 265                 270

Gly Val Glu Val His Asn Ala Lys Thr Lys Pro Arg Glu Glu Gln Phe
        275                 280                 285

Asn Ser Thr Tyr Arg Val Val Ser Val Leu Thr Val Leu His Gln Asp
```

```
                  290                 295                 300
Trp Leu Asn Gly Lys Glu Tyr Lys Cys Lys Val Ser Asn Lys Gly Leu
305                 310                 315                 320

Pro Ser Ser Ile Glu Lys Thr Ile Ser Lys Ala Lys Gly Gln Pro Arg
                325                 330                 335

Glu Pro Gln Val Tyr Thr Leu Pro Pro Ser Gln Glu Glu Met Thr Lys
            340                 345                 350

Asn Gln Val Ser Leu Thr Cys Leu Val Lys Gly Phe Tyr Pro Ser Asp
            355                 360                 365

Ile Ala Val Glu Trp Glu Ser Asn Gly Gln Pro Glu Asn Asn Tyr Lys
        370                 375                 380

Thr Thr Pro Pro Val Leu Asp Ser Asp Gly Ser Phe Phe Leu Tyr Ser
385                 390                 395                 400

Arg Leu Thr Val Asp Lys Ser Arg Trp Gln Glu Gly Asn Val Phe Ser
                405                 410                 415

Cys Ser Val Met His Glu Ala Leu Lys Phe His Tyr Thr Gln Lys Ser
            420                 425                 430

Leu Ser Leu Ser Leu Gly
        435

<210> SEQ ID NO 73
<211> LENGTH: 438
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Ser Thr Tyr Ser Met
            20                  25                  30

Arg Trp Val Arg Gln Ala Pro Gly Lys Gly Leu Glu Trp Val Ser Ser
        35                  40                  45

Ile His Thr Gly Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Asn Leu Arg Ala Glu Asp Thr Ala Ile Tyr Tyr Cys Val Ile
                85                  90                  95

Ala Gly Tyr Ser Asp Trp Gly Gln Gly Thr Leu Val Thr Val Ser Ser
            100                 105                 110

Ala Ser Thr Lys Gly Pro Ser Val Phe Pro Leu Ala Pro Cys Ser Arg
        115                 120                 125

Ser Thr Ser Glu Ser Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Lys Thr
            180                 185                 190

Tyr Thr Cys Asn Val Asp His Lys Pro Ser Asn Thr Lys Val Asp Lys
        195                 200                 205
```

```
Arg Val Glu Ser Lys Tyr Gly Pro Pro Cys Pro Pro Cys Pro Ala Pro
    210                 215                 220
Glu Phe Leu Gly Gly Pro Ser Val Phe Leu Phe Pro Pro Lys Pro Lys
225                 230                 235                 240
Asp Thr Leu Tyr Ile Thr Arg Glu Pro Glu Val Thr Cys Val Val Val
                245                 250                 255
Asp Val Ser Gln Glu Asp Pro Glu Val Gln Phe Asn Trp Tyr Val Asp
            260                 265                 270
Gly Val Glu Val His Asn Ala Lys Thr Lys Pro Arg Glu Glu Gln Phe
        275                 280                 285
Asn Ser Thr Tyr Arg Val Val Ser Val Leu Thr Val Leu His Gln Asp
    290                 295                 300
Trp Leu Asn Gly Lys Glu Tyr Lys Cys Lys Val Ser Asn Lys Gly Leu
305                 310                 315                 320
Pro Ser Ser Ile Glu Lys Thr Ile Ser Lys Ala Lys Gly Gln Pro Arg
                325                 330                 335
Glu Pro Gln Val Tyr Thr Leu Pro Pro Ser Gln Glu Glu Met Thr Lys
            340                 345                 350
Asn Gln Val Ser Leu Thr Cys Leu Val Lys Gly Phe Tyr Pro Ser Asp
        355                 360                 365
Ile Ala Val Glu Trp Glu Ser Asn Gly Gln Pro Glu Asn Asn Tyr Lys
    370                 375                 380
Thr Thr Pro Pro Val Leu Asp Ser Asp Gly Ser Phe Phe Leu Tyr Ser
385                 390                 395                 400
Arg Leu Thr Val Asp Lys Ser Arg Trp Gln Glu Gly Asn Val Phe Ser
                405                 410                 415
Cys Ser Val Met His Glu Ala Leu His Asn His Tyr Thr Gln Lys Ser
            420                 425                 430
Leu Ser Leu Ser Leu Gly
        435

<210> SEQ ID NO 74
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Val Met Thr Gln Ser Pro Leu Ser Leu Pro Val Thr Pro Gly
1               5                   10                  15
Glu Ser Ala Ser Ile Ser Cys Lys Thr Ser Gln Gly Leu Val His Ser
            20                  25                  30
Asp Gly Lys Thr Tyr Phe Tyr Trp Phe Leu Gln Lys Pro Gly Gln Ser
        35                  40                  45
Pro Gln Gln Leu Ile Tyr Gln Val Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Lys Ala Glu Asp Ala Gly Val Tyr Tyr Cys Ala His Gly
                85                  90                  95
Thr Tyr Tyr Pro His Thr Phe Gly Gln Gly Thr Arg Leu Glu Ile Lys
            100                 105                 110
Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 75
<211> LENGTH: 329
<212> TYPE: PRT
<213> ORGANISM: Homo sapiens

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
            275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 76
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 77
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu Lys Phe His Tyr Thr
305                 310                 315                 320

Gln Lys Ser Leu Ser Leu Ser Pro Gly
                325
```

```
<210> SEQ ID NO 78
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly
                325

<210> SEQ ID NO 79
<211> LENGTH: 327
<212> TYPE: PRT
```

<213> ORGANISM: Homo sapiens

<400> SEQUENCE: 79

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 80
<211> LENGTH: 326
<212> TYPE: PRT
<213> ORGANISM: Homo sapiens

<400> SEQUENCE: 80

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 81
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Ala Ser Thr Lys Gly Pro Ser Val Phe Pro Leu Ala Pro Cys Ser Arg
 1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

```
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Lys Thr
 65                  70                  75                  80
Tyr Thr Cys Asn Val Asp His Lys Pro Ser Asn Thr Lys Val Asp Lys
                 85                  90                  95
Arg Val Glu Ser Lys Tyr Gly Pro Pro Cys Pro Pro Cys Pro Ala Pro
                100                 105                 110
Glu Phe Leu Gly Gly Pro Ser Val Phe Leu Phe Pro Pro Lys Pro Lys
                115                 120                 125
Asp Thr Leu Tyr Ile Thr Arg Glu Pro Glu Val Thr Cys Val Val Val
130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
                195                 200                 205
Pro Ser Ser Ile Glu Lys Thr Ile Ser Lys Ala Lys Gly Gln Pro Arg
210                 215                 220
Glu Pro Gln Val Tyr Thr Leu Pro Pro Ser Gln Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
                260                 265                 270
Thr Thr Pro Pro Val Leu Asp Ser Asp Gly Ser Phe Phe Leu Tyr Ser
                275                 280                 285
Arg Leu Thr Val Asp Lys Ser Arg Trp Gln Glu Gly Asn Val Phe Ser
                290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 82
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Ser Thr Lys Gly Pro Ser Val Phe Pro Leu Ala Pro Cys Ser Arg
 1               5                  10                  15
Ser Thr Ser Glu Ser Thr Ala Ala Leu Gly Cys Leu Val Lys Asp Tyr
                 20                  25                  30
Phe Pro Glu Pro Val Thr Val Ser Trp Asn Ser Gly Ala Leu Thr Ser
                 35                  40                  45
Gly Val His Thr Phe Pro Ala Val Leu Gln Ser Ser Gly Leu Tyr Ser
                 50                  55                  60
Leu Ser Ser Val Val Thr Val Pro Ser Ser Ser Leu Gly Thr Lys Thr
 65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 83
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

```
            100                 105                 110
Glu Phe Leu Gly Gly Pro Ser Val Phe Leu Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu Lys Phe His Tyr Thr Gln Lys Ser
305                 310                 315                 320

Leu Ser Leu Ser Leu Gly Lys
                325

<210> SEQ ID NO 84
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125
```

```
Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu Lys Phe His Tyr Thr Gln Lys Ser
305                 310                 315                 320

Leu Ser Leu Ser Leu Gly
                325

<210> SEQ ID NO 85
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Leu His Glu Ala Leu His Ser His Tyr Thr Gln Lys Ser
305                 310                 315                 320

Leu Ser Leu Ser Leu Gly Lys
                325

<210> SEQ ID NO 86
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180
```

```
                180                 185                 190
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Leu His Glu Ala Leu His Ser His Tyr Thr Gln Lys Ser
305                 310                 315                 320

Leu Ser Leu Ser Leu Gly
                325

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: G, E or D
<220> FEATURE:
<221> NAME/KEY: MOD_RES
<222> LOCATION: (6)..(6)
<223> OTHER INFORMATION: G or A

<400> SEQUENCE: 87

Ser Ile His Thr Xaa Xaa Gly Gly Thr Ala Tyr Arg Asp Ser Val Lys
1               5                   10                  15

Gly

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: D or G

<400> SEQUENCE: 88

Lys Thr Ser Gln Gly Leu Val His Ser Xaa Gly Lys Thr Tyr Phe Tyr
1               5                   10                  15

<210> SEQ ID NO 89
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<221> NAME/KEY: MOD_RES
<222> LOCATION: (3)..(3)
<223> OTHER INFORMATION: V or L
<220> FEATURE:
<221> NAME/KEY: MOD_RES
<222> LOCATION: (28)..(28)
<223> OTHER INFORMATION: G or S
<220> FEATURE:
<221> NAME/KEY: MOD_RES
<222> LOCATION: (38)..(38)
<223> OTHER INFORMATION: V or A
<220> FEATURE:
<221> NAME/KEY: MOD_RES
<222> LOCATION: (52)..(52)
<223> OTHER INFORMATION: G, E or D
<220> FEATURE:
<221> NAME/KEY: MOD_RES
<222> LOCATION: (53)..(53)
<223> OTHER INFORMATION: G or A
<220> FEATURE:
<221> NAME/KEY: MOD_RES
<222> LOCATION: (73)..(73)
<223> OTHER INFORMATION: A or S
<220> FEATURE:
<221> NAME/KEY: MOD_RES
<222> LOCATION: (83)..(83)
<223> OTHER INFORMATION: S or N
<220> FEATURE:
<221> NAME/KEY: MOD_RES
<222> LOCATION: (85)..(85)
<223> OTHER INFORMATION: R or K
<220> FEATURE:
<221> NAME/KEY: MOD_RES
<222> LOCATION: (86)..(86)
<223> OTHER INFORMATION: A or P
<220> FEATURE:
<221> NAME/KEY: MOD_RES
<222> LOCATION: (91)..(91)
<223> OTHER INFORMATION: I or V
<220> FEATURE:
<221> NAME/KEY: MOD_RES
<222> LOCATION: (107)..(107)
<223> OTHER INFORMATION: L or Q

<400> SEQUENCE: 89

Gln Leu Xaa Glu Ser Gly Gly Gly Leu Val Gln Pro Gly Gly Ser Leu
1               5                   10                  15

Arg Leu Ser Cys Ala Ala Ser Gly Phe Thr Phe Xaa Thr Tyr Ser Met
            20                  25                  30

Arg Trp Val Arg Gln Xaa Pro Gly Lys Gly Leu Glu Trp Val Ser Ser
        35                  40                  45

Ile His Thr Xaa Xaa Gly Gly Thr Ala Tyr Arg Asp Ser Val Lys Gly
    50                  55                  60

Arg Phe Thr Ile Ser Arg Asp Asn Xaa Lys Asn Thr Leu Tyr Leu Gln
65                  70                  75                  80

Met Asn Xaa Leu Xaa Xaa Glu Asp Thr Ala Xaa Tyr Tyr Cys Val Ile
                85                  90                  95

Ala Gly Tyr Ser Asp Trp Gly Gln Gly Thr Xaa Val Thr Val Ser Ser
            100                 105                 110

<210> SEQ ID NO 90
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)

```
<223> OTHER INFORMATION: G or S
<220> FEATURE:
<221> NAME/KEY: MOD_RES
<222> LOCATION: (38)..(38)
<223> OTHER INFORMATION: V or A
<220> FEATURE:
<221> NAME/KEY: MOD_RES
<222> LOCATION: (52)..(52)
<223> OTHER INFORMATION: G, E or D
<220> FEATURE:
<221> NAME/KEY: MOD_RES
<222> LOCATION: (53)..(53)
<223> OTHER INFORMATION: G or A
<220> FEATURE:
<221> NAME/KEY: MOD_RES
<222> LOCATION: (83)..(83)
<223> OTHER INFORMATION: S or N
<220> FEATURE:
<221> NAME/KEY: MOD_RES
<222> LOCATION: (85)..(85)
<223> OTHER INFORMATION: R or K
<220> FEATURE:
<221> NAME/KEY: MOD_RES
<222> LOCATION: (86)..(86)
<223> OTHER INFORMATION: A or P
<220> FEATURE:
<221> NAME/KEY: MOD_RES
<222> LOCATION: (91)..(91)
<223> OTHER INFORMATION: I or V
<220> FEATURE:
<221> NAME/KEY: MOD_RES
<222> LOCATION: (107)..(107)
<223> OTHER INFORMATION: L or Q

<400> SEQUENCE: 90

Gln Leu Val Glu Ser Gly Gly Gly Leu Val Gln Pro Gly Gly Ser Leu
1               5                   10                  15

Arg Leu Ser Cys Ala Ala Ser Gly Phe Thr Phe Xaa Thr Tyr Ser Met
                20                  25                  30

Arg Trp Val Arg Gln Xaa Pro Gly Lys Gly Leu Glu Trp Val Ser Ser
            35                  40                  45

Ile His Thr Xaa Xaa Gly Gly Thr Ala Tyr Arg Asp Ser Val Lys Gly
    50                  55                  60

Arg Phe Thr Ile Ser Arg Asp Asn Ala Lys Asn Thr Leu Tyr Leu Gln
65                  70                  75                  80

Met Asn Xaa Leu Xaa Xaa Glu Asp Thr Ala Xaa Tyr Tyr Cys Val Ile
                85                  90                  95

Ala Gly Tyr Ser Asp Trp Gly Gln Gly Thr Xaa Val Thr Val Ser Ser
            100                 105                 110

<210> SEQ ID NO 91
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: L or G
<220> FEATURE:
<221> NAME/KEY: MOD_RES
<222> LOCATION: (12)..(12)
<223> OTHER INFORMATION: P or S
<220> FEATURE:
<221> NAME/KEY: MOD_RES
<222> LOCATION: (14)..(14)
<223> OTHER INFORMATION: T or V
<220> FEATURE:
<221> NAME/KEY: MOD_RES
```

```
<222> LOCATION: (33)..(33)
<223> OTHER INFORMATION: D or G
<220> FEATURE:
<221> NAME/KEY: MOD_RES
<222> LOCATION: (51)..(51)
<223> OTHER INFORMATION: Q or L
<220> FEATURE:
<221> NAME/KEY: MOD_RES
<222> LOCATION: (68)..(68)
<223> OTHER INFORMATION: S or T
<220> FEATURE:
<221> NAME/KEY: MOD_RES
<222> LOCATION: (82)..(82)
<223> OTHER INFORMATION: R or G
<220> FEATURE:
<221> NAME/KEY: MOD_RES
<222> LOCATION: (84)..(84)
<223> OTHER INFORMATION: K or E
<220> FEATURE:
<221> NAME/KEY: MOD_RES
<222> LOCATION: (88)..(88)
<223> OTHER INFORMATION: A or V
<220> FEATURE:
<221> NAME/KEY: MOD_RES
<222> LOCATION: (95)..(95)
<223> OTHER INFORMATION: H or Q
<220> FEATURE:
<221> NAME/KEY: MOD_RES
<222> LOCATION: (105)..(105)
<223> OTHER INFORMATION: Q or S

<400> SEQUENCE: 91

Asp Ile Val Met Thr Gln Ser Pro Xaa Ser Leu Xaa Val Xaa Pro Gly
1               5                   10                  15

Glu Ser Ala Ser Ile Ser Cys Lys Thr Ser Gln Gly Leu Val His Ser
            20                  25                  30

Xaa Gly Lys Thr Tyr Phe Tyr Trp Phe Leu Gln Lys Pro Gly Gln Ser
        35                  40                  45

Pro Gln Xaa Leu Ile Tyr Gln Val Ser Asn Arg Ala Ser Gly Val Pro
    50                  55                  60

Asp Arg Phe Xaa Gly Ser Gly Ser Gly Thr Asp Phe Thr Leu Lys Ile
65                  70                  75                  80

Ser Xaa Val Xaa Ala Glu Asp Xaa Gly Val Tyr Tyr Cys Ala Xaa Gly
            85                  90                  95

Thr Tyr Tyr Pro His Thr Phe Gly Xaa Gly Thr Arg Leu Glu Ile Lys
            100                 105                 110

<210> SEQ ID NO 92
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: L or G
<220> FEATURE:
<221> NAME/KEY: MOD_RES
<222> LOCATION: (12)..(12)
<223> OTHER INFORMATION: P or S
<220> FEATURE:
<221> NAME/KEY: MOD_RES
<222> LOCATION: (14)..(14)
<223> OTHER INFORMATION: T or V
<220> FEATURE:
<221> NAME/KEY: MOD_RES
<222> LOCATION: (33)..(33)
<223> OTHER INFORMATION: D or G
<220> FEATURE:
```

```
<221> NAME/KEY: MOD_RES
<222> LOCATION: (68)..(68)
<223> OTHER INFORMATION: S or T
<220> FEATURE:
<221> NAME/KEY: MOD_RES
<222> LOCATION: (82)..(82)
<223> OTHER INFORMATION: R or G
<220> FEATURE:
<221> NAME/KEY: MOD_RES
<222> LOCATION: (84)..(84)
<223> OTHER INFORMATION: K or E
<220> FEATURE:
<221> NAME/KEY: MOD_RES
<222> LOCATION: (88)..(88)
<223> OTHER INFORMATION: A or V
<220> FEATURE:
<221> NAME/KEY: MOD_RES
<222> LOCATION: (95)..(95)
<223> OTHER INFORMATION: H or Q
<220> FEATURE:
<221> NAME/KEY: MOD_RES
<222> LOCATION: (105)..(105)
<223> OTHER INFORMATION: Q or S

<400> SEQUENCE: 92

Asp Ile Val Met Thr Gln Ser Pro Xaa Ser Leu Xaa Val Xaa Pro Gly
1               5                   10                  15

Glu Ser Ala Ser Ile Ser Cys Lys Thr Ser Gln Gly Leu Val His Ser
            20                  25                  30

Xaa Gly Lys Thr Tyr Phe Tyr Trp Phe Leu Gln Lys Pro Gly Gln Ser
        35                  40                  45

Pro Gln Gln Leu Ile Tyr Gln Val Ser Asn Arg Ala Ser Gly Val Pro
    50                  55                  60

Asp Arg Phe Xaa Gly Ser Gly Ser Gly Thr Asp Phe Thr Leu Lys Ile
65                  70                  75                  80

Ser Xaa Val Xaa Ala Glu Asp Xaa Gly Val Tyr Tyr Cys Ala Xaa Gly
                85                  90                  95

Thr Tyr Tyr Pro His Thr Phe Gly Xaa Gly Thr Arg Leu Glu Ile Lys
                100                 105                 110

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: S or H
<220> FEATURE:
<221> NAME/KEY: MOD_RES
<222> LOCATION: (5)..(5)
<223> OTHER INFORMATION: G, E or D
<220> FEATURE:
<221> NAME/KEY: MOD_RES
<222> LOCATION: (6)..(6)
<223> OTHER INFORMATION: G or A

<400> SEQUENCE: 93

Ser Ile Xaa Thr Xaa Xaa Gly Gly Thr Ala Tyr Arg Asp Ser Val Lys
1               5                   10                  15

Gly
```